(12) United States Patent
Rose

(10) Patent No.: US 9,760,853 B2
(45) Date of Patent: Sep. 12, 2017

(54) LOW-POWER WIRELESSLY-LINKED RFID TRACKING SYSTEM

(76) Inventor: Mark D. Rose, Albany, OR (US)

( * ) Notice: Subject to any disclaimer, the term of this patent is extended or adjusted under 35 U.S.C. 154(b) by 0 days.

(21) Appl. No.: 13/165,759

(22) Filed: Jun. 21, 2011

(65) Prior Publication Data

US 2011/0309931 A1 Dec. 22, 2011

Related U.S. Application Data

(60) Provisional application No. 61/357,047, filed on Jun. 21, 2010, provisional application No. 61/433,948, (Continued)

(51) Int. Cl.
*G08B 21/00* (2006.01)
*G06Q 10/08* (2012.01)
(Continued)

(52) U.S. Cl.
CPC ............. *G06Q 10/08* (2013.01); *E21F 17/18* (2013.01); *G01N 33/0075* (2013.01);
(Continued)

(58) Field of Classification Search
CPC ........ G08B 21/02; G08B 21/22; G08B 23/00; G08B 26/007; G06Q 10/0833
(Continued)

(56) References Cited

U.S. PATENT DOCUMENTS 8,149,109 B2 * 4/2012 Lontka .................... 340/539.11
8,253,555 B2 * 8/2012 Stevenson et al. ...... 340/539.12
(Continued)

FOREIGN PATENT DOCUMENTS

KR 20080095992 A 10/2008
KR 100955592 B1 4/2010

OTHER PUBLICATIONS

ISA Korea, International Search Report of PCT/US2011/041311, Jan. 13, 2012, WIPO, 3 pages.

*Primary Examiner* — Mark Rushing
*Assistant Examiner* — Munear Akki
(74) *Attorney, Agent, or Firm* — Alleman Hall McCoy Russell + Tuttle LLP

(57) ABSTRACT

A wirelessly-linked RFID tracking system is disclosed herein. The system includes low-power wirelessly-linked RFID readers in communication with a mine radio network to detect and transmit information received from a plurality of RFID tags. The RFID readers transmit tag information to a local server for providing notification and/or alarm information to system users as required under the Miner Act of 2006. The RFID readers may further include environmental sensors to sense and communicate environmental conditions wirelessly. In addition, the optional capability of hi-intensity warning LEDs mounted on the reader devices, may be deployed to alert personnel of an emergency condition even when hundreds of feet away from the device, irrespective of background noise prevalent in mining operations. The disclosed system communicatively links a plurality of wireless RFID readers to each other and/or to the mine radio network to create a data path from an underground environment to a surface environment. It should be appreciated that the system may be applied in a number of environments, including, but not limited to mines, oil platforms, industrial surface complexes, such as petroleum refineries, ships, etc.

22 Claims, 39 Drawing Sheets

Related U.S. Application Data filed on Jan. 18, 2011, provisional application No. 61/434,798, filed on Jan. 20, 2011.

(51) Int. Cl.
*E21F 17/18* (2006.01)
*G01S 5/00* (2006.01)
*G01S 5/02* (2010.01)
*G01N 33/00* (2006.01)
*G06K 17/00* (2006.01)

(52) U.S. Cl.
CPC ............. *G01S 5/0009* (2013.01); *G01S 5/02* (2013.01); *G06K 2017/0045* (2013.01)

(58) Field of Classification Search
USPC ................... 340/539.13, 571.1, 539.26, 10.1
See application file for complete search history.

(56) References Cited

U.S. PATENT DOCUMENTS

| | | | | |
|---|---|---|---|---|
| 8,428,511 B1* | 4/2013 | Gunasekara | ........... | H04B 13/02 340/12.32 |
| 8,501,103 B2* | 8/2013 | Bangera et al. | .............. | 422/117 |
| 2006/0022800 A1* | 2/2006 | Krishna et al. | .............. | 340/10.2 |
| 2006/0139168 A1* | 6/2006 | Pratt | ....................... | G08C 17/02 340/539.22 |
| 2006/0145855 A1* | 7/2006 | Diorio | ................ | G06K 19/0723 340/572.1 |
| 2006/0208888 A1* | 9/2006 | Patel et al. | .................. | 340/572.1 |
| 2007/0103303 A1* | 5/2007 | Shoarinejad | .................. | 340/572.1 |
| 2008/0061937 A1* | 3/2008 | Park | ....................... | G06K 7/0008 340/10.1 |
| 2008/0084314 A1* | 4/2008 | Dipiazza | ................ | G01S 13/74 340/573.1 |
| 2008/0129525 A1* | 6/2008 | Barrus | ................. | G08B 25/002 340/669 |
| 2008/0231449 A1* | 9/2008 | Moshfeghi | ............. | G01D 21/00 340/572.1 |
| 2008/0266106 A1* | 10/2008 | Lim et al. | .................. | 340/572.7 |
| 2008/0307435 A1* | 12/2008 | Rehman | .................. | G06F 9/542 719/318 |
| 2009/0140852 A1* | 6/2009 | Stolarczyk | ............... | H01Q 1/04 340/539.13 |
| 2009/0175615 A1* | 7/2009 | Kobayashi | ............. | G03B 17/24 396/310 |
| 2009/0273444 A1* | 11/2009 | Brown | ......................... | 340/10.1 |
| 2009/0309724 A1* | 12/2009 | Cecil | ...................... | G08B 13/24 340/552 |
| 2010/0141385 A1* | 6/2010 | Shiau | ................... | H04B 5/0062 340/10.1 |
| 2011/0037599 A1* | 2/2011 | Johnson, Jr. | ........... | H04W 4/043 340/632 |
| 2011/0205033 A1* | 8/2011 | Bandyopadhyay et al. | .......................... | 340/10.51 |
| 2013/0022350 A1* | 1/2013 | Kozischek et al. | .............. | 398/10 |

\* cited by examiner

LOW-POWER WIRELESSLY-LINKED RFID TRACKING SYSTEM

CROSS REFERENCE TO RELATED APPLICATION

This application claims priority to U.S. Provisional Application No. 61/357,047, filed Jun. 21, 2010, and titled LOW-POWER WIRELESSLY-LINKED RFID TRACKING SYSTEM, U.S. Provisional Application No. 61/433,948, filed Jan. 18, 2011, and titled LOW-POWER WIRELESSLY-LINKED RFID TRACKING SYSTEM, and U.S. Provisional Application No. 61/434,798, filed Jan. 20, 2011, and titled LOW-POWER WIRELESSLY-LINKED RFID TRACKING SYSTEM. The entirety of the above listed applications is incorporated herein by reference for all purposes.

BACKGROUND

Keeping track of people and equipment in underground areas can be complicated. Confined spaces and rock may interfere with communication signals. Workers in underground areas, such as mines or tunnels, face many environmental hazards, including potential cave-ins, gas leaks, and other harmful situations. Because underground tunnel networks may extend over a large area, rescuers searching for trapped workers may have difficulty locating trapped workers. Further, trapped workers may have difficulty finding self-rescue tools and supplies deployed throughout a tunnel network.

Some previous approaches to providing communication in underground areas include adding independent underground radio tracking networks in addition to existing underground radio communication networks. However, such approaches may not be easily extensible and may compete with other underground utilities for power, space, etc. Extending, upgrading, and maintaining underground utilities for such independent radio networks may further complicate existing underground communication systems.

SUMMARY

Accordingly, various embodiments are provided herein for a wirelessly-linked RFID tracking system configured for tracking a plurality of RFID tags. For example, self-contained, low-power wirelessly-linked RFID readers communicating with an existing mine radio network are provided to detect and transmit information received from a plurality of small size, easily carried RFID tags borne by underground workers or underground equipment. Such RFID tags may store information about the worker or the equipment bearing the RFID tag. The wirelessly-linked RFID readers may then transmit the tag information of various RFID tags to a local server, the local server providing notification and/or alarm information for the various RFID tags to system users. Further, various user interface modules are provided to permit such wirelessly-linked RFID tracking systems to be configured, monitored, and maintained by system users using local and/or remote servers.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
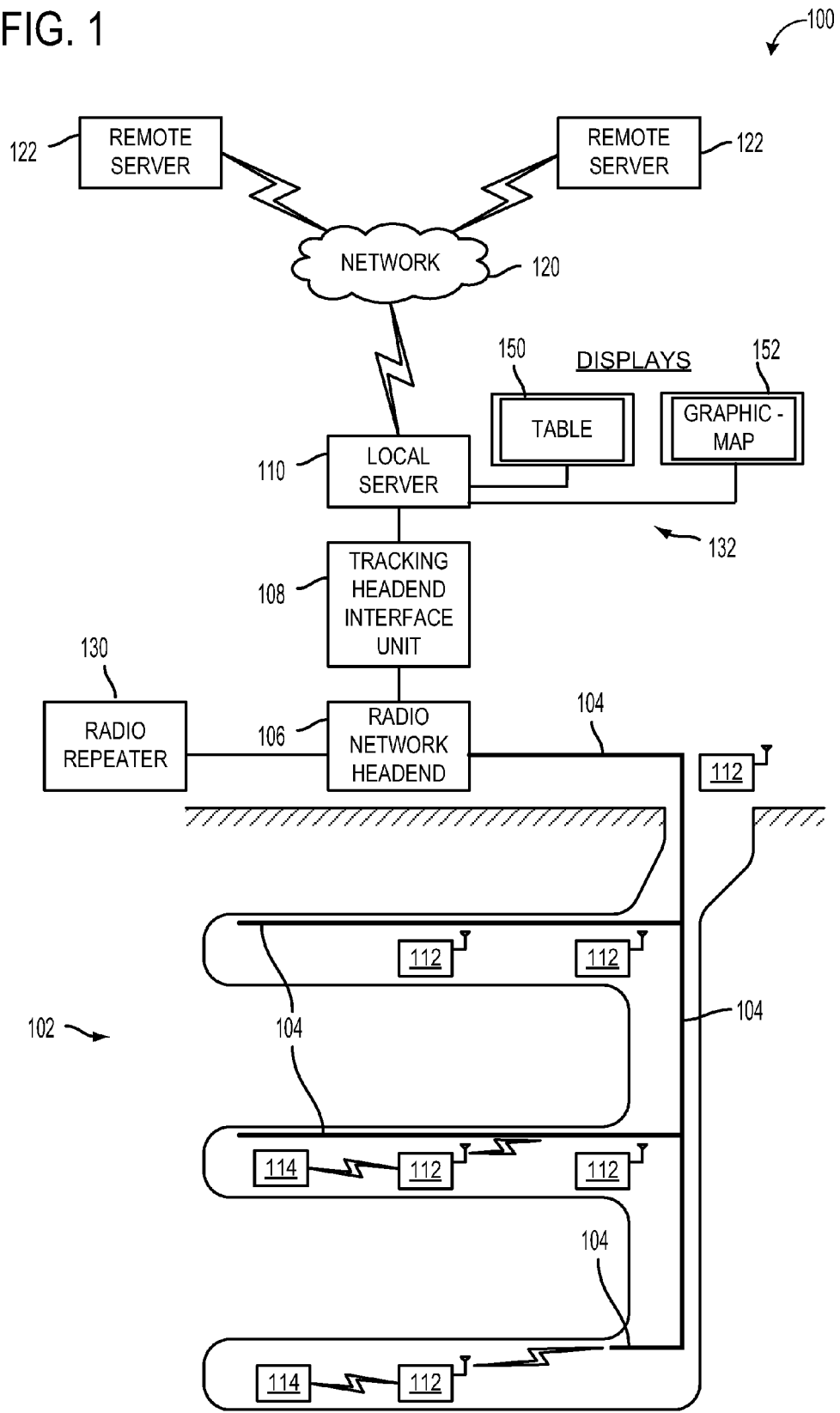
FIG. 1 schematically shows an example operating environment for a wirelessly-linked radio frequency identification (RFID) system in accordance with an embodiment of the present disclosure.

One approach to providing underground tracking and communication is with a wirelessly-linked radio frequency identification (RFID) system. For example, a wirelessly-linked RFID tracking system may include a wirelessly-linked RFID reader, which may have an all-wireless reader/radio capability. The wirelessly-linked RFID reader may collect tag information from a plurality of RFID tags as they pass within range of an RFID antenna or an RFID antenna system of the wirelessly-linked RFID reader.

The wirelessly-linked RFID reader may add time and location information to the tag information, and may store the tag information for wireless transmission to an existing mine radio network (which may be a two-way radio network). In this way, wirelessly-linked RFID readers are communicatively linked with the existing mine radio network so as to create a data path from an underground environment to a surface environment, for example. In some embodiments, tag information may be generated and/or transmitted in real time. In other example embodiments, tag information may be generated and/or transmitted in response to a polling command or via other bursting transmission methods. As an example, a tag reception timer may be integral with the reader unit. Further, it should be appreciated that the tag reception timer may be synchronized to the master computer clock on the surface for accuracy.

The wirelessly-linked RFID readers may be physically independent of the mine radio network. For example, some embodiments of the wirelessly-linked RFID readers may be self-contained, so that no hard-wired connections to the mine radio network are required. This configuration is referred to as multi-hop and is described in more detail herein. Further, in some embodiments, a wirelessly-linked RFID reader may be located hundreds of feet from the mine radio network while still providing wireless data connectivity. Further still, in some examples, a single wirelessly-linked RFID reader may have a plurality of RFID receivers (and reverse transmitters, if activated) (such as an RFID input port) to create a plurality of distinct RFID tag reception zones for receiving tag information from various RFID tags.

Tag information transmitted from the wirelessly-linked RFID readers may be received at one or more local servers for coordinating and operating the wirelessly-linked RFID tracking system. Such local servers may be used to program or update the wirelessly-linked RFID readers. In some embodiments, a tracking headend interface unit may facilitate an interface between the mine radio network and the local server. For example, in some embodiments, a connection between a Tracking Head Unit and the server computer may be accomplished via a serial or USB (universal serial port) where the server is local to the head unit. In some embodiments, such connections may be extended using Internet protocol (IP) to Serial interface converters, RS-232 to RS-485 converters, or other suitable wireless link schemes where the server is remotely located from the head unit. Other example embodiments are discussed in more detail below.

Some examples of the wirelessly-linked RFID tracking system may be configured to use one or more frequencies in a land mobile radio band which may have a frequency range of approximately 144-950 MHz, which may permit the wirelessly-linked RFID tracking system to operate using an existing or new commercial two-way underground mine radio network. This may provide ready deployment and extensibility of the wirelessly-linked RFID tracking system.

Aspects of this disclosure will now be described by example and with reference to the illustrated embodiments. Components and other elements that may be substantially the same in one or more embodiments are identified coordinately and are described with minimal repetition. It will be noted, however, that elements identified coordinately may also differ to some degree. Furthermore, the size, shape, and/or configurations of the various components of the wirelessly-linked RFID tracking system are provided to ease understanding and are not intended to be technically precise.

FIG. 1 schematically shows an example operating environment for a wirelessly-linked RFID tracking system 100. In one example, mine workers working in different areas of mine 102 may be tracked as they go about their work. Wirelessly-linked RFID tracking system 100 may track location information for the workers, time information for the workers, etc. during the course of a shift.

Figure 2:
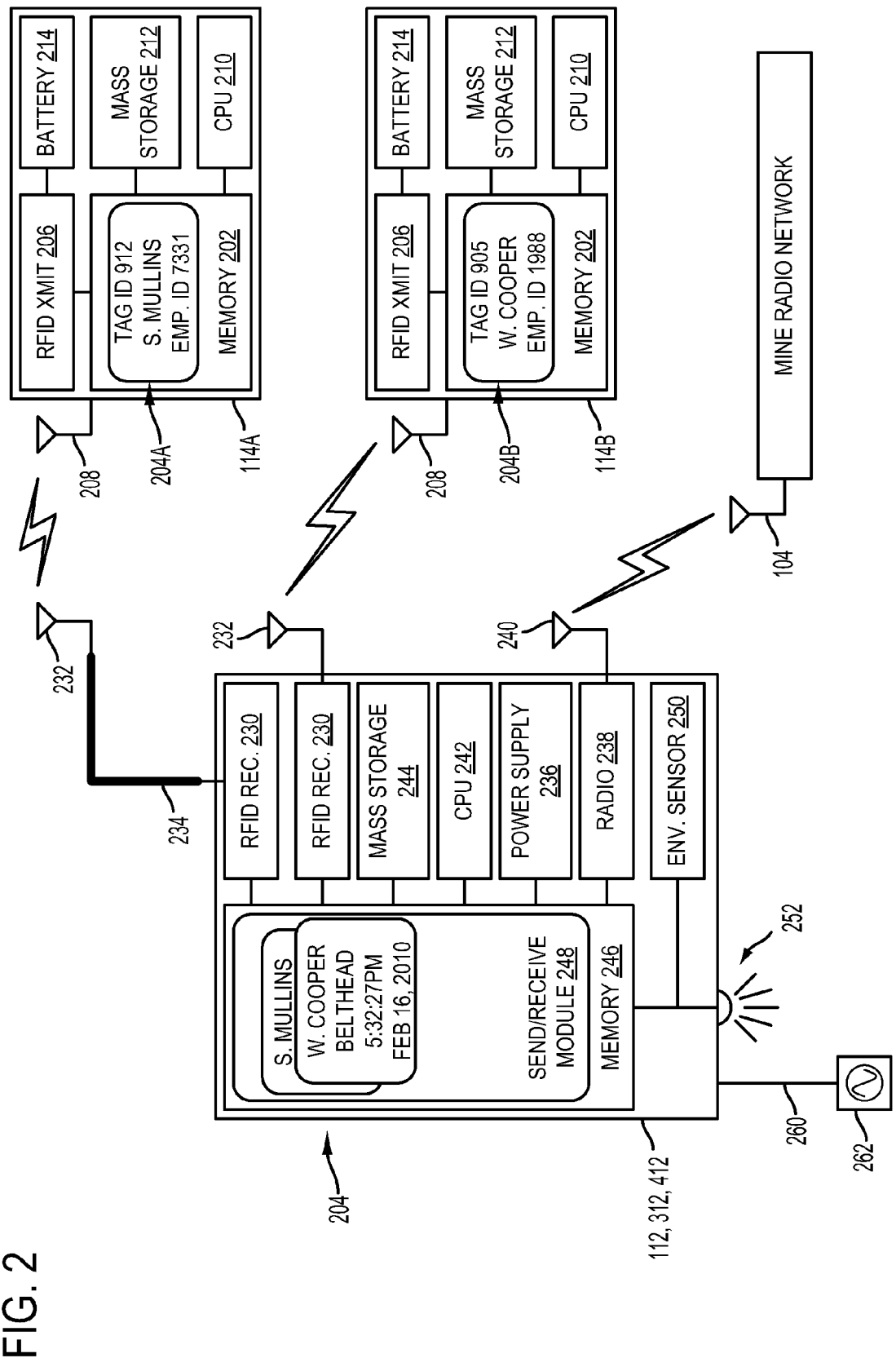
FIG. 2 schematically shows an example wireless RFID reader and example RFID transmitters in accordance with an embodiment of the present disclosure.
Figure 3:
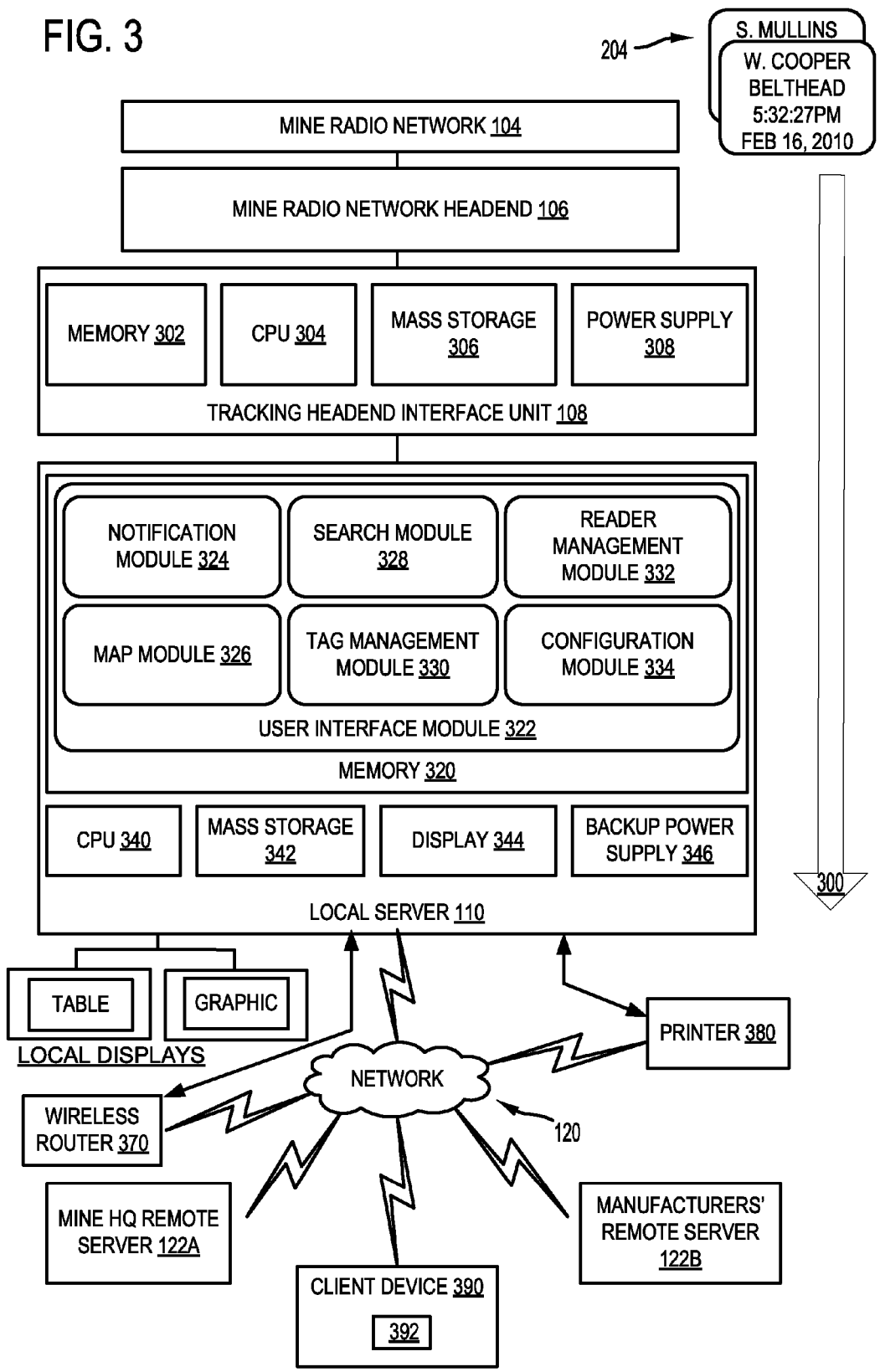
FIG. 3 schematically shows an example server computing device and radio network tracking headend interface unit in accordance with an embodiment of the present disclosure.
Figure 4:
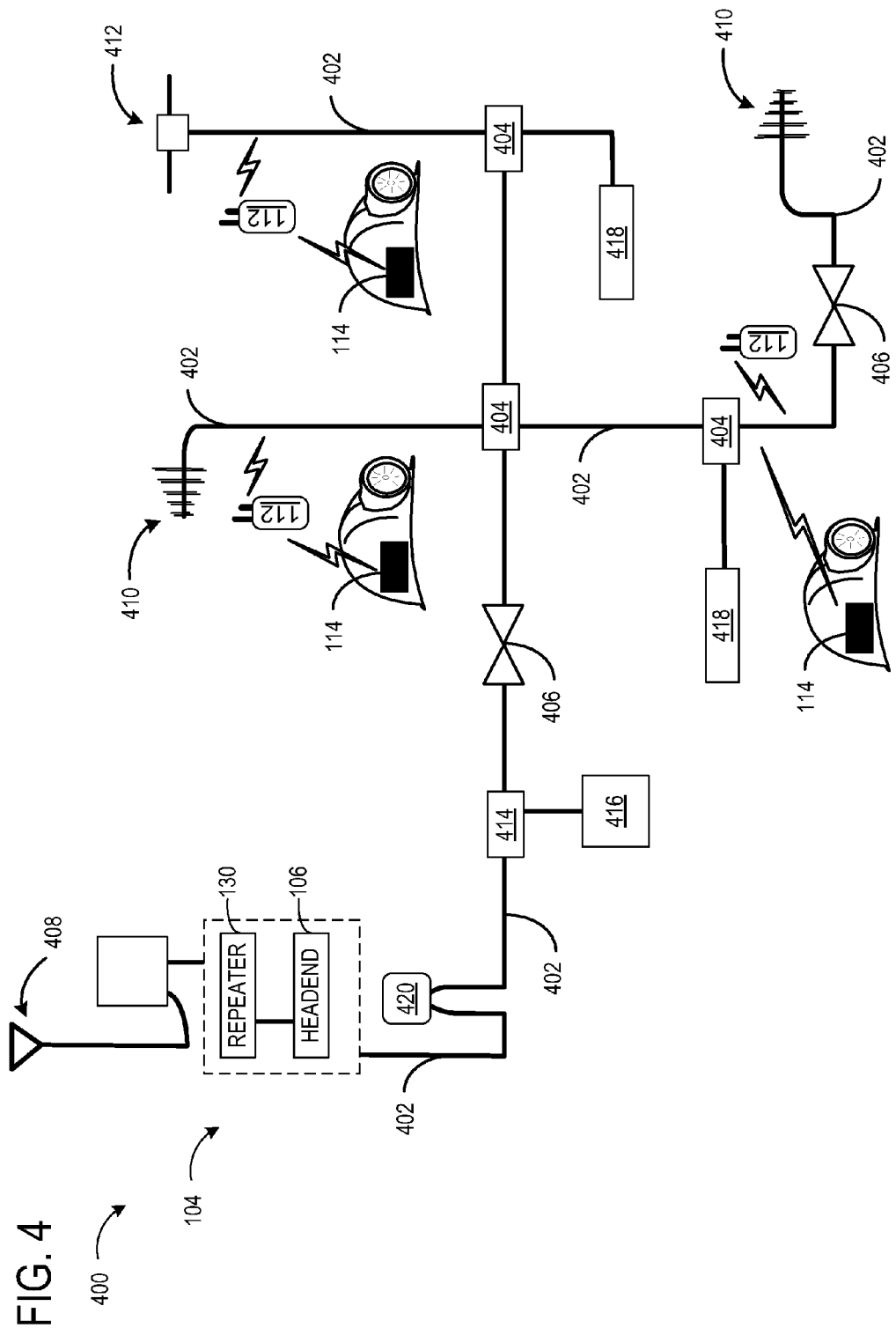
FIG. 4 schematically shows another example operating environment for a wirelessly-linked RFID system in accordance with an embodiment of the present disclosure.
Figure 5:
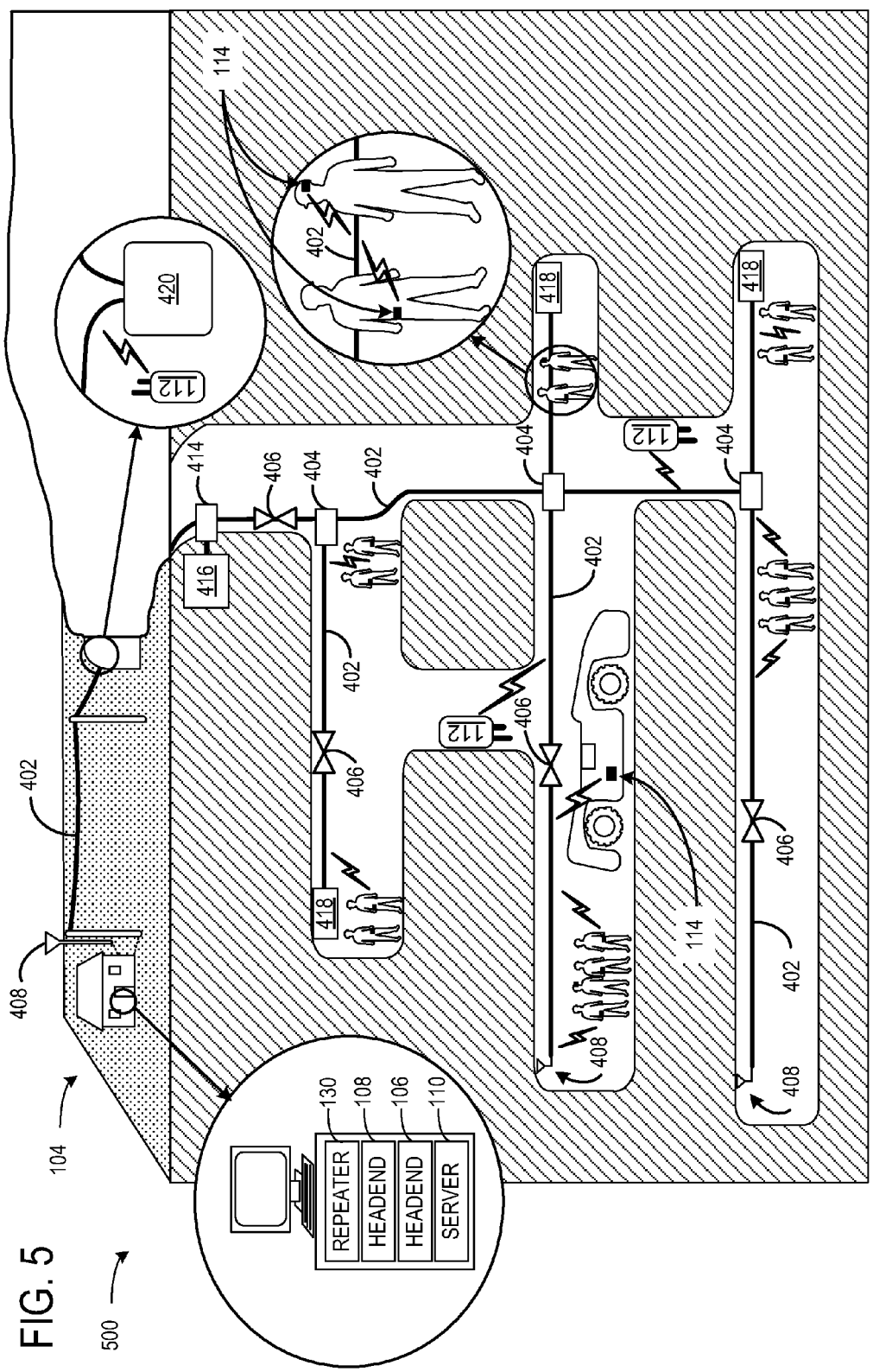
FIG. 5 schematically shows another example operating environment for a wirelessly-linked RFID system in accordance with an embodiment of the present disclosure.

The RFID tracking system is further illustrated in FIGS. 2-5 which should be referenced in combination with FIG. 1. In this regard, the FIG. 2 schematically shows an example wireless RFID reader and example RFID transmitters and FIG. 3 schematically shows an example server computing device and radio network tracking headend interface unit for use in the RFID tracking system. For further illustrative purposes, FIGS. 4-5 show example embodiments of wirelessly-linked RFID tracking systems in operation.

Figure 29:
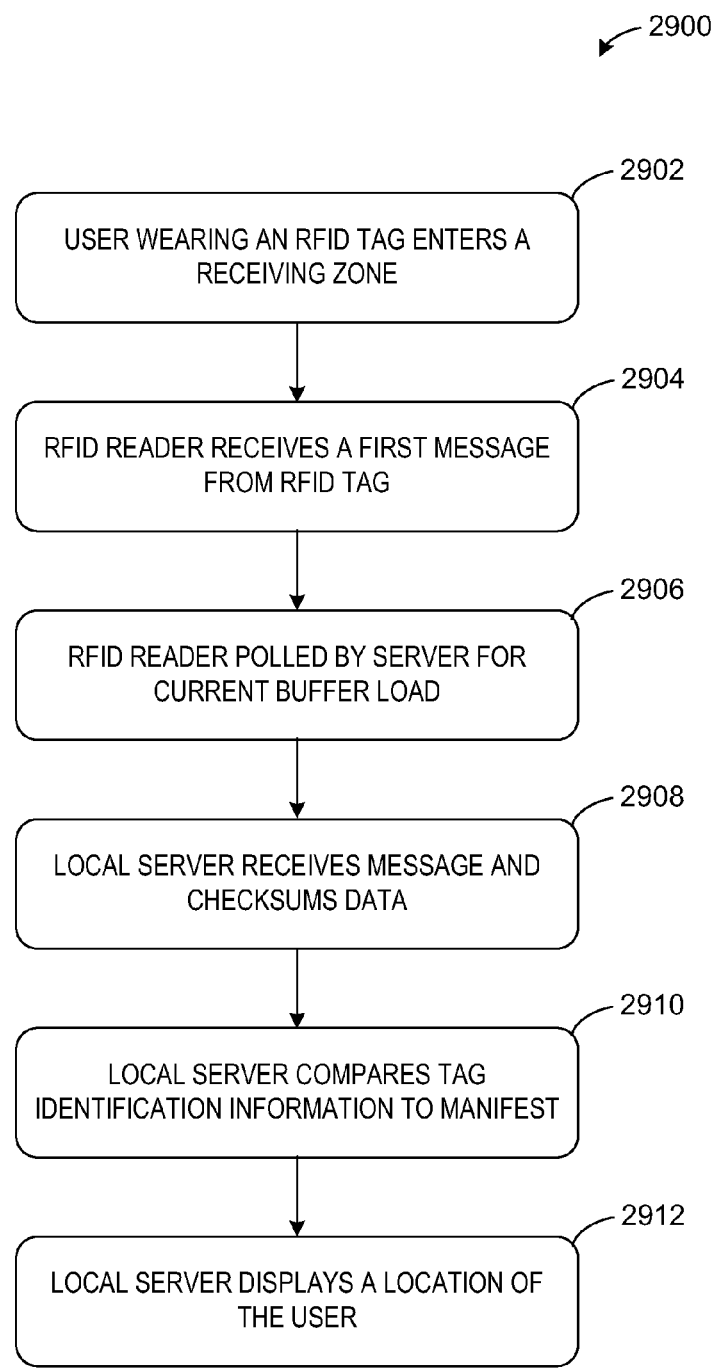
FIG. 29 shows an example flowchart for a method of tracking an RFID tag, polling the RFID reader and receiving tag data in accordance with an embodiment of the present disclosure.

To further appreciate system 100, attention is directed to FIG. 29 which shows an example flowchart for a method 2900 for use with the RFID tracking system. The method provides a flowchart of using the RFID tacking system for tracking personnel and/or equipment bearing an RFID tag using an embodiment of a wirelessly-linked RFID tracking system. Method 2900 may be employed after deploying a plurality of wirelessly-linked RFID readers in communication with a mine radio network, within an underground environment, for example. At 2902, a user (e.g., a miner) wearing an RFID tag enters a receiving zone of an RFID reader. At 2904, the RFID reader receives a first message from the RFID tag, the first message including data stored at the RFID tag, also referred to as tag data.

At 2906, the RFID reader is polled by the server for current buffer load. The reader is thus, in some examples, polled directly via the underground radio network, or optionally, indirectly via an adjacent wireless reader and requests a send from the polled unit. In this way, tag data may be sent as a message to the server.

For example, the polled reader may transmit a second message back to the local server via an existing mine radio network and/or an interconnecting reader. The second message may include at least a portion of the data received from the first message. The second message may include additional information. For example, the second message may include a time, and/or location corresponding to the receipt of the first message; however, it will be appreciated that the second message may include other information, e.g. atmospheric monitoring data. In this way, the tag may provide a unique identifier where time and location is appended to the tag ID in the reader. It is noted that in some systems the reader time is synchronized to computer time as part of the initial server boot up such that there is time accuracy. It should be appreciated that the above examples are provided as non-limiting examples. Further, in some examples, the tag data is checksummed to verify and check the validity of the data for security purposes. The reader data buffer may be cleared after the polling and checksum of the data.

At 2908, the local server receives the second message, and at 2910, the local server compares RFID tag identification information to a manifest. At 2912, the local server displays a location of the miner, either in tables, such as indicated at 150 in FIG. 1 and/or in a graphic view 152. The displays may include a mine map overlay, such that the graphic indicates in a map form the position and location of the RFID tag and thus the miner and/or equipment with the RFID tag. Time data may be also stored and displayed. The incoming data posts to a database in the server and may be queued to populate tables and/or graphics.

Referring against to FIG. 29, it will be appreciated that method 2900 is provided by way of example and may include additional or alternative steps than those shown in FIG. 29. Further, it is to be understood that an RFID reader may receive a plurality of first messages, each message from an individual RFID tag. In this way, the RFID reader may receive information pertaining to each RFID tag within the receiving zone and transmit a second message for each RFID tag to the local server. Further, the RFID reader may transmit a second message for each first message or the RFID reader may transmit a consolidated second message including at least a portion of the data received from each of the first messages, for example.

As described in more detail below, information stored in the reader(s) are securely transferred to the surface computer and head unit before the reader holding buffer(s) are cleared. Security methods, such as data checksum methodologies, may be employed to ensure the accuracy of the data from the readers. In such examples, the data is maintained in the holding buffer until the data is confirmed.

By using the systems and methods described herein, it will be appreciated that personnel and equipment location information may be tracked throughout a mine environment. Such a system and method may provide location information when other communication mechanisms are unavailable. For example, in the event of an emergency condition in mine 102, monitoring personnel on the surface may direct rescue efforts in the mine using the location and time information provided by the wirelessly-linked RFID tracking system. Thus, in an emergency scenario, rescuers may be able to evacuate miners from unstable conditions, rescue isolated miners, etc. While the discussion below is directed at embodiments used in underground mines, it will be appreciated that this disclosure is not so limited. For example, some embodiments may also be suitable for above ground, open air use and/or confined space use. As an example, the described systems and methods may be used on shipboard, offshore drill rigs, refineries, buildings or other shielded environments. Further such use of the system in environments such as oil platforms, industrial surface complexes, such as petroleum refineries, ships, etc. likewise provides a cost effective solution in contrast to systems where the use of a wired RFID reader connective would be more costly or prohibitive than wireless connectivity from the reader to the host computers.

Turning back to FIG. 1, by way of an overview, the example wirelessly-linked RFID tracking system 100 includes a local server 110 with displays, such as table display 150 and graphic display 152, a tracking headend interface unit 108, a mine radio network headend 106, a mine radio network 104, and a plurality of wirelessly-linked RFID readers 112 interfaced with mine radio network 104. Wirelessly-linked RFID tracking system 100 may span more than one environment, for example, some portions of system 100 may associate with a mine 102 environment and some portions of system 100 may associate with a surface 132 environment, which are provided as non-limiting examples. In some embodiments, each wireless RFID "reader" may have a unique identification number to create a reader zone with an identification relating to the reader ID number. This "ID" may be displayed as a configurable alias that is customizable and therefore may relate to nomenclature common to each facility. For example, an RFID reader ID may be configured as "SECTION 6 LEFT" in a coal mine, which may correlate to RFID reader unique ID "7106." It will be appreciated that any combination of alpha and/or numeric RFID reader aliases are possible without departing from the scope of this disclosure.

Wirelessly-linked RFID tracking system 100 also includes a plurality of RFID tags 114. Optionally, some embodiments of wirelessly-linked RFID tracking system 100 may include a network 120 for communicating with one or more remote servers 122. Each of these components will be discussed in detail below.

Mine radio network 104 is configured to provide radio communications throughout mine 102. Mine radio network 104 may include one or more suitable "radiating" and "non-radiating" coaxial cables, splitters, splice boxes, junction boxes, amplifiers or "signal boosters", antennas, power inserts, power supplies, cable termination units, surge protectors, etc. to provide suitable two-way radio communication within a mine, or other shielded environment, 102 and between mine 102 and surface 132. Such a network is defined as a Distributed Antenna System by the Federal Communications Commission (FCC) definition.

In addition to FIG. 1, for purposes of illustration, FIGS. 4-6 and 23 schematically show other example mine radio network configurations 400, 500, 600, and 2300 respectively. Each of the aforementioned configurations may include various distributed antenna system radio components selected from the group consisting of cables 402 (e.g., radiating coaxial cables, non-radiating coaxial cables, etc.), splitters 404, splice boxes 2302, amplifiers 406, antennas 408 (e.g., Yagi antennas 410, dipole antennas 412), power inserts 414, power suppliers 416, cable termination units 418, and surge protectors 420. In some embodiments, mine radio network 104 may be a "leaky feeder" communications system; in some other embodiments, mine radio network 104 may be a DAS communications system (Distributed Antenna System) in a shielded wireless environment such as an underground mine or other facility where radio signals are obstructed. In some applications, a DAS network may consist of a head unit, base radio and coaxial cable, such as small mines, ships, buildings and offshore drill rigs.

Again referring back to FIG. 1, mine radio network 104 is controlled by mine radio network headend 106, which facilitates communications over mine radio network 104. Radio communication via mine radio network 104 is conducted at one or more frequencies of a radio spectrum to provide mobile communication, such as a two-way radio communication network. For example, mine radio network 104 may be a land mobile radio band under Part 90 of FCC rules, which may have a frequency range of approximately 144-950 MHz. In some embodiments, mine radio network headend 106 may facilitate half-duplex mode communication, where different transmission and reception channels of mine radio network 104 are used to facilitate uplink and downlink of tag/reader information.

In one example, transmission to mine radio network 104 may occur at 450 MHz while reception from mine radio network 104 may occur at 470 MHz. Alternatively, as a non-limiting example, in the VHF band, the channels may be 150 Mhz and 170 Mhz or closer depending on the radio network locally installed used to carry the reader data. The subject RFID wireless network, both head unit and readers may be frequency programmable in simplex or ½ duplex mode across the radio band, and hence may be configured to operate as "stand alone" or be configured to operate compatible with an existing radio network in the facility requiring RFID capabilities, or both.

Additionally, in some embodiments, mine radio network headend 106 may facilitate full-duplex mode communication. It will be appreciated that other suitable methods of duplexing and/or multiplexing may be used by mine radio network headend 106 when controlling mine radio network 104. In most embodiments, a radio repeater 130 will be electrically connected to mine radio network headend 106. For example, radio repeater 130 may be connected to mine radio network headend 106 using transmit (Tx) and receive (Rx) ports connected by one or more coaxial cables.

Wirelessly-linked RFID readers 112 are in radio communication with the facility radio network 104 either directly and/or indirectly, so that information received from RFID tags 114 may be transmitted wirelessly to local server 110 via mine radio network 104. FIG. 2 schematically shows an example wirelessly-linked RFID reader 112 in communication with example RFID tags 114A and 114B.

Figure 6:
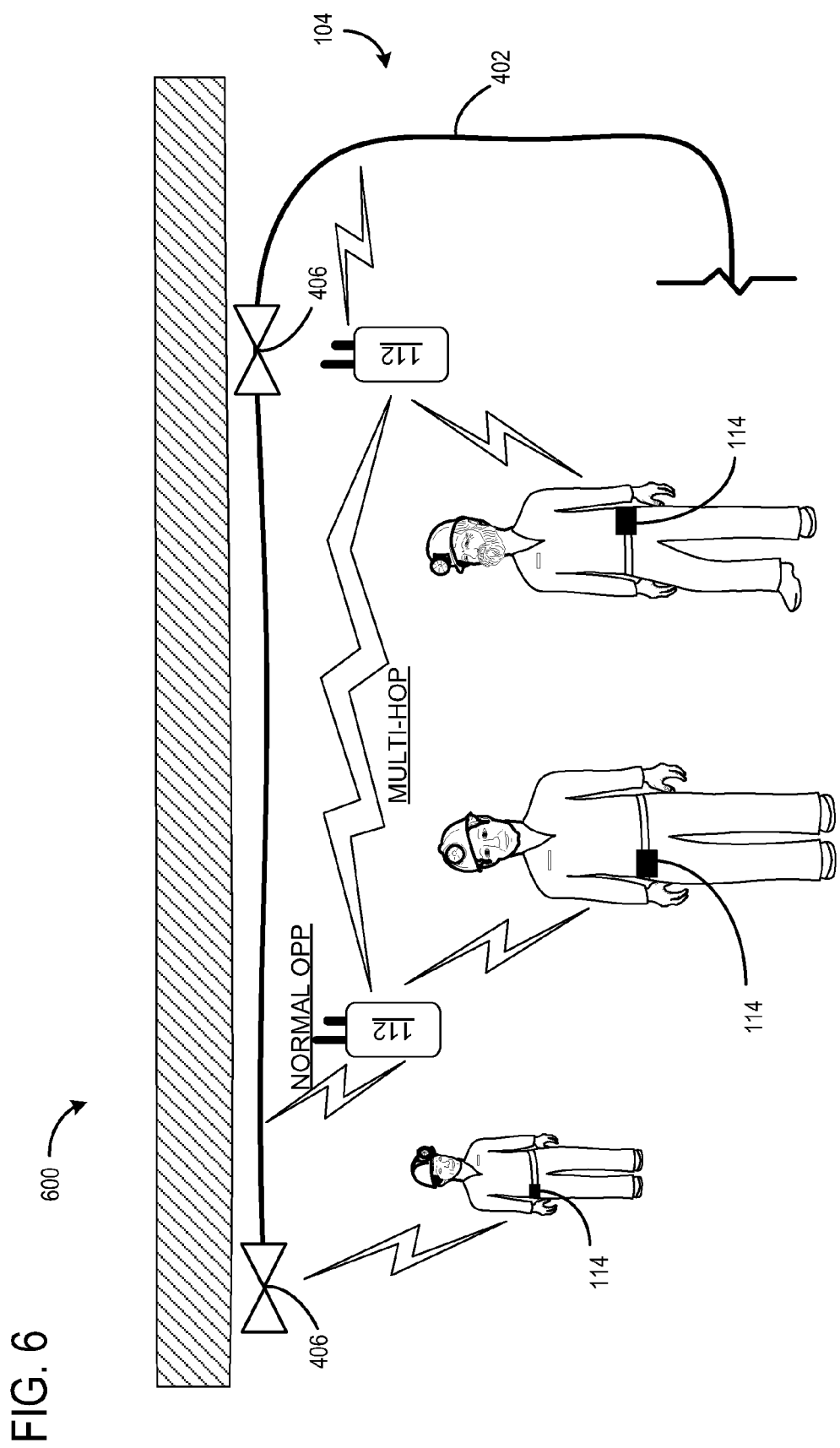
FIG. 6 schematically shows another example of a wireless RFID reader and example RFID transmitters in accordance with an embodiment of the present disclosure. In some examples, operation or reader to surface wireless data path uses mine underground radio network as the data highway. In other examples or in combination, alternate operation of wireless data connectivity from readers to surface is multi-hop mode, where one reader links to another out of the facility until connected to the server controller on the surface.
Figure 7:
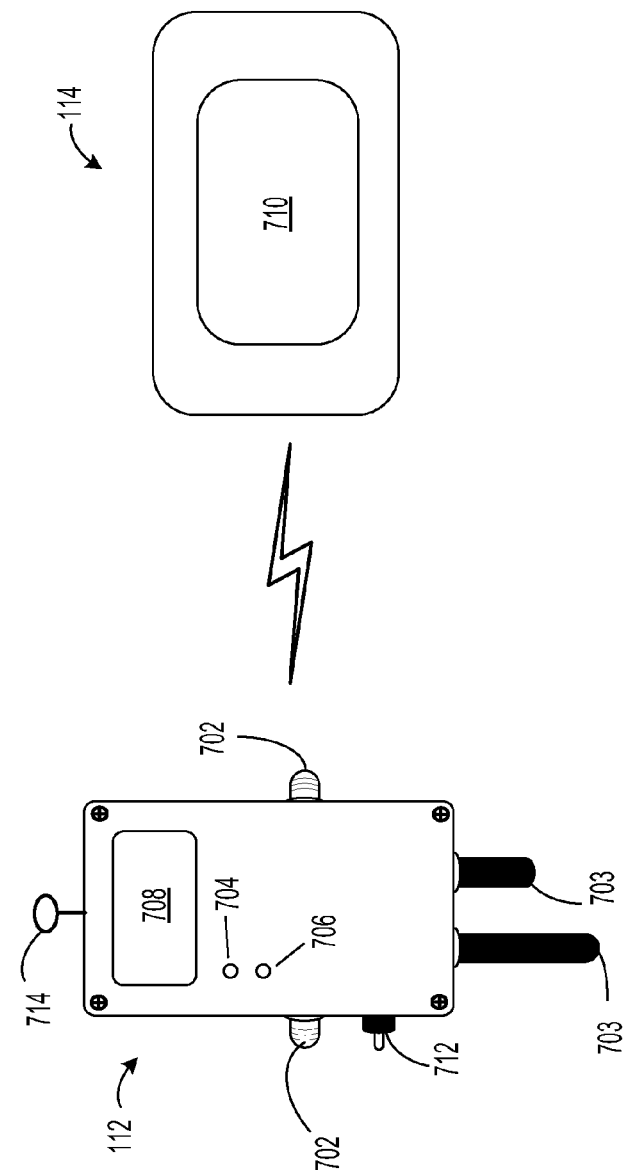
FIG. 7 shows another example of a wireless RFID reader and an example RFID transmitter in accordance with an embodiment of the present disclosure.

Further illustrations of the use of wirelessly-linked RFID readers are shown in FIGS. 6 and 7. Turning to FIG. 6, an example is illustrated where wirelessly-linked RFID readers 112 receive transmissions from personnel-mounted embodiments of RFID tags 114. It will be appreciated that while FIG. 6 shows RFID tags 114 mounted to a belt of each user, the RFID tags 114 may be attached or carried elsewhere. For example, an RFID tag may be attached to a user's helmet, which is provided as one non-limiting example. Further, in some examples, RFID tags may be attached or coupled to mine equipment.

As shown in FIG. 6, RFID readers may be connected to the mine underground radio network as the data highway (reader 112 connection to cable). Such operation is indicated as NORMAL OPP and provides operation of the reader to surface wireless data path using mine underground radio network as the data highway. Alternate operation of wireless data connectivity from readers to surface is indicated as MULTI-HOP (reader 112 connected to reader 112), where one reader links to another out of the facility until connected to the server controller on the surface. A combination of NORMAL OPP and MULTI-HOP may be used throughout the system.

As another example, FIG. 7 shows a further embodiment of each of wirelessly-linked RFID reader 112 and RFID tag 114. As shown, RFID reader 112 includes a plurality of ports 702 that may be configured to receive or otherwise communicatively couple the RFID reader 112 to one or more of an RFID receiver, an RF network antenna, a power source, and/or a plurality of environmental sensors, such as a methane sensor, and/or a carbon monoxide sensor in some uses. It will be appreciated that virtually any receiver/transceiver, power source, antenna, and sensor configured to communicate with the facility radio network 104 may be communicatively coupled to RFID reader 112 via a port 702. Further, it is noted that antennae or other communication links may be connected through ports, such as network communication ports 703. In addition to the ports 702 and 703, one or more cable entry inputs, such as 712, may be provided on reader 112.

Additionally, RFID reader 112 may include tag indicator 704 and/or communication indicator 706 which may illuminate to indicate a status of an RFID tag and/or a status of communication with the mine radio network. It will be appreciated that RFID reader may include additional or alternative indicators than those shown in FIG. 7. For example, the indicator may provide immediate feedback of a condition indicating breach of a sensor threshold, such as a high level of carbon monoxide or other gas. As another example, the indicator may provide visual information regarding the state of the RFID reader, such as power information, message receipt or sending information, etc. Although shown as a visual indicator, the indicator may also be an audible indicator, a vibrating indicator and/or a combination visual, audible and/or vibrating indicator. In addition to the inclusion of one or more indicators, RFID reader 112 and RFID tag 114 may include indicia 708 and indicia 710 respectively.

Further, in some embodiments, a hanger ring or other coupling or attachment devices, such as hang tag or hanger ring 714, may be provided to enable selective attachment of the reader. Although hanger ring 714 is shown on the top center of the reader, alternative positions and configurations may be used for attachment or coupling of the reader.

Figure 28:
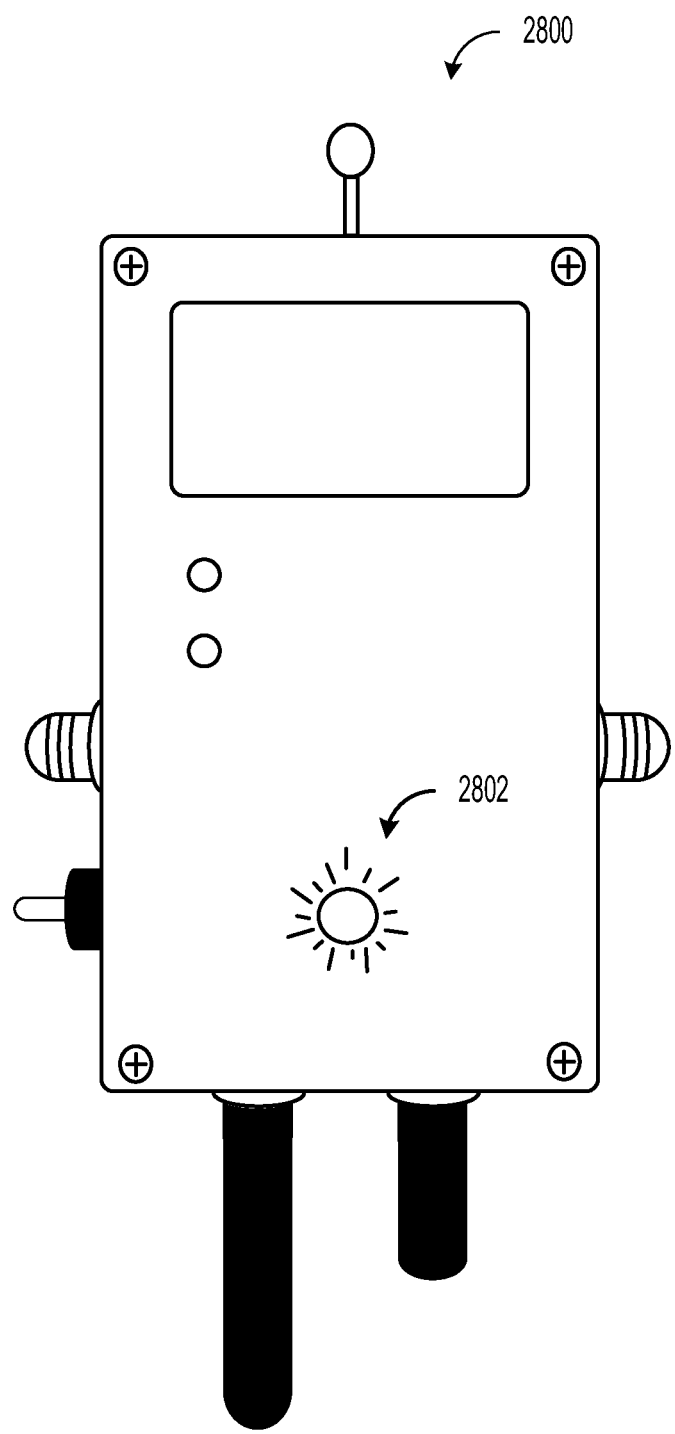
FIG. 28 shows an example wirelessly-linked RFID reader including an indicator light in accordance with an embodiment of the present disclosure.

Likewise, FIG. 28 shows another example wirelessly-linked RFID reader 2800 including an indicator light 2802, which is depicted in an illuminated state. As illustrated for example purposes, a cable entry (such as for DC power input) is located on the right hand side of the reader below the type "N" connector. Although shown with the cable entry on the right hand side, other positions of the cable entry and the connectors are within the scope of the disclosure. Further, the hanger ring for attachment to the mine roof or back may be alternatively positioned other than then the top center position shown.

Turning back to FIG. 2, RFID tags 114 may be self-contained, portable computing devices including memory 202 for storing tag information 204 and for holding instructions executable on processor 210. In some examples, the memory may be integrated within the RFID tag; however in other embodiments, a memory card or other device may be used with the RFID tag.

RFID tags 114 may be mounted to equipment or carried by a user. In some embodiments, RFID tags 114 may be suitably small so that an RFID tag 114 may be comfortably mounted on a user's belt, hat, arm, leg, etc. Further, in some embodiments, RFID tag 114 may be ruggedly constructed to withstand harsh operating conditions, such as underground conditions. As described briefly above, in some embodiments, RFID tags 114 may include one or more environmental sensors, to sense for example, one or more of a gas species (such as $CH_4$, CO, O2, SO2, No2, etc.) and/or concentration of a gas species, temperature, humidity, pressure, etc. at a particular location. Use of the RFID reader system enables information from the environmental sensors to be sent back to the local server and tracked and displayed, such as in a graphic map overview.

Tag information 204 may include any suitable information, such as an employee name, an employee ID number, a tag ID number, a supervisor's name, emergency contact information for the employee, and other personal information, such as the employee's age, Social Security identification number, gender, start date, etc. In the example shown in FIG. 2, RFID tag 114A includes tag information 204A. Specifically, tag information 204A indicates that employee S. Mullins, employee ID 7331, is wearing a tag having a tag ID number of 912. Similarly, RFID tag 114B includes tag information 204B for employee W. Cooper, employee ID 1988, bearing tag number 905. Tag information 204 may also include data about the associated RFID tag 114, such as low battery warning data, etc. As will be discussed in detail elsewhere in this disclosure, in some embodiments, tag information 204 may be configured by local server 110 and/or remote server 122.

Tag information 204 is transmitted from RFID tag 114 via RFID transmitter 206 and tag antenna 208 to one of the wirelessly-linked RFID readers 112. In some embodiments, RFID tag 114 may encrypt tag information 204 so that transmission to wirelessly-linked RFID reader 112 is a secured data transmission.

RFID transmitter 206 may be any suitable radio transmitter. In some embodiments, RFID transmitter 206 may transmit at one or more frequencies within a range of approximately 315 MHz-2.4 GHz. In some embodiments, RFID transmitter 206 may be configured to transmit tag information 204 in multiple bursts at regular intervals.

In the example shown in FIG. 2, RFID tag 114 also includes a battery 214. Additionally or alternatively, in some embodiments, another suitable power supply may be included in RFID tag 114. For example, an energy-harvesting device may be included in RFID tag 114.

In some embodiments, RFID tags 114 may include a mass storage device 212 for storing tag information 204 when RFID tag 114 is unpowered. Non-limiting specifications for an example RFID tag 114 are included below in Table 1.

TABLE 1

Example RFID Tag Specifications

| | |
|---|---|
| RFID Tag/MSHA certification | Tunnel Radio Model T1/MSHA 23-A080005-0 |
| RF Power | 0 dBm nominal (approx.) |
| Battery | 3 VDC Lithium (approx.) |

Wirelessly-linked RFID reader 112 is a computing device, including memory 246, processor 242, and mass storage 244. Wirelessly-linked RFID reader 112 may, in some embodiments, be of rugged construction to withstand harsh operating conditions, such as underground conditions. For example, in some embodiments, wirelessly-linked RFID reader 112 may be enclosed in an IP66 and UL-rated, impact resistant, dust- and water-proof aluminum enclosure.

Wirelessly-linked RFID reader 112 includes at least one RFID receiver 230 for receiving an RFID transmission from RFID tag 114, a remote antenna, a remote sensor, and/or receiving an RFID transmission from another RFID reader 112. RFID receiver 230 may be any suitable RFID receiver configured to receive transmission from RFID tag 114. In some embodiments, RFID receiver 230 may receive transmissions at one or more frequencies within a range of approximately 315 MHz-2.4 GHz. Operation of RFID receivers 230 in this range may provide lower power consumption and longer battery duty cycles and lifetime. In some embodiments, RFID receiver 230 may be configured as a high-isolation, long-range receiver to capture transmissions from distantly located RFID tags 114, to provide better transmission capture during two-way radio traffic, etc. One non-limiting RFID receiver may receive a transmission from an RFID tag located up to 400 feet away.

Each RFID receiver 230 may be in electrical communication with an RFID reader antenna 232. Any suitable RFID antenna 232 may be employed. In some embodiments, a hard-wired connection 234 may be provided to allow placement of RFID antenna 232 at a greater distance from wirelessly-linked RFID reader 112, which may provide different RFID capture zones with RFID transmission service by the same wirelessly-linked RFID reader 112. Use of hard-wired connection 234 may avoid signal degradation during transmission of the received radio signal from RFID antenna 232 to RFID receiver 230. For example, hard-wired connection 234 may be a coaxial cable linking RFID antenna 232 to RFID receiver 230.

In some embodiments, a plurality of RFID receivers 230 may be used. The use of a plurality of RFID readers may provide additional zones for receiving information from RFID tags 114 concurrently. The example shown in FIG. 2 illustrates two such receivers, but it will be appreciated that additional RFID receivers 230 may be incorporated according to a particular application. Non-limiting specifications for an example wirelessly-linked RFID reader 112 having three RFID receivers 230 are included below in Table 2.

TABLE 2

Example Wirelessly-linked RFID Reader Specifications

| | |
|---|---|
| VDC | 3-25 VDC |
| DC Current | 100 mA, typical |
| Network Connection | +10 dBm, adjustable 0-10 dBm |
| $P_{1dB}$, Transmit (120-1000 MHz) | |
| RFID Freq(s) | 315 MHz, 433 MHz, 915 MHz |
| Battery types | 3.6 VDC LiON Pack or 6 VDC 12 AH SLA |
| Antenna Ports | Type "N") 1-4 RFID inputs, 1 Link Radio |
| Modulation types | FSK, ASK, OOK |
| Dimensions (two sizes) | 255 × 250 × 121 MM or 160 × 260 × 91 MM |
| Rating | IP66, UL50 & 508 |
| Construction | Compression Fiberglass or Aluminum (waterproof and/or dustproof) |

Again referring to FIG. 2, wirelessly-linked RFID reader 112 may include a send/receive module 248 stored in mass storage 244 and loaded into memory 246 for execution on processor 242. Send/receive module 248 is configured to receive tag information 204 from RFID receiver 230, store tag information 204, and forward it to radio 238 for transmission over mine radio network 104.

In some embodiments, send/receive module 248 may be configured to add metadata to tag information 204. For example, in some embodiments, each wirelessly-linked RFID reader 112 may be associated with a reader identifier (such as, but not limited to, a unique RFID reader identification number) for identifying various wirelessly-linked RFID readers within wirelessly-linked RFID tracking system 100. Thus, in one scenario, reader identifier metadata may be added to tag information 204.

It will be appreciated that any suitable metadata may be appended to tag information 204; non-limiting examples include time, location, and environmental information (such as sensor information). In the example shown in FIG. 2, tag information 204B for W. Cooper has be updated with metadata indicating that W. Cooper's tag information was received at the belthead location at 5:32:27 PM on Feb. 16, 2010. In some embodiments, send/receive module 248 may be configured to encrypt tag information 204 for secure transmission over mine radio network 104.

Wirelessly-linked RFID reader 112 transmits tag information 204 over mine radio network 104 to local server 110 via radio 238 and radio antenna 240, which is in electrical communication with radio 238. It will be appreciated that any suitable transmission scheme may be employed. For example, transmission of tag information 204 may occur in real time, at predetermined intervals, and/or in response to polling commands received from local server 110 via mine radio network 104.

Radio 238 may be any suitable radio configured to facilitate transmission with mine radio network 104. This may allow wirelessly-linked RFID readers 112 to be deployed throughout mine 102 using an existing mine radio network 104 as a backbone for conveying tag information 204. Thus, the installation and maintenance of a separate underground radio communication network for transmitting RFID information may be avoided, which may potentially simplify maintenance of wirelessly-linked RFID tracking system 100, reduce start-up and overhead costs, etc. Further, in some embodiments, wirelessly-linked RFID readers 112 may have no physical connection to mine radio network 104, which may reduce installation and maintenance costs. In some embodiments, radio 238 may operate at one or more frequencies in the range of approximately 148-950 MHz in a half-duplex mode, a full duplex mode, etc. Thus, it will be appreciated that, in some embodiments, mine radio network 104 may be used to facilitate transmission of tag information 204 as well as two-way voice communication.

Continuing with FIG. 2, wirelessly-linked RFID reader 112 may include a power supply 236. In some embodiments, power supply 236 may be a battery. Alternatively or additionally, in some embodiments, wirelessly-linked RFID reader 112 may include a connection to an external DC power supply. For example, FIG. 2 shows wirelessly-linked RFID reader 112 connected to an externally-located power supply 262 by a power cord 260. In some embodiments, a single external power supply may provide power to two or more wirelessly-linked RFID readers 112. Thus, it will be appreciated that power supply 236 may include any suitable power supply, including, in some embodiments, any suitable backup power supply.

Figure 25:
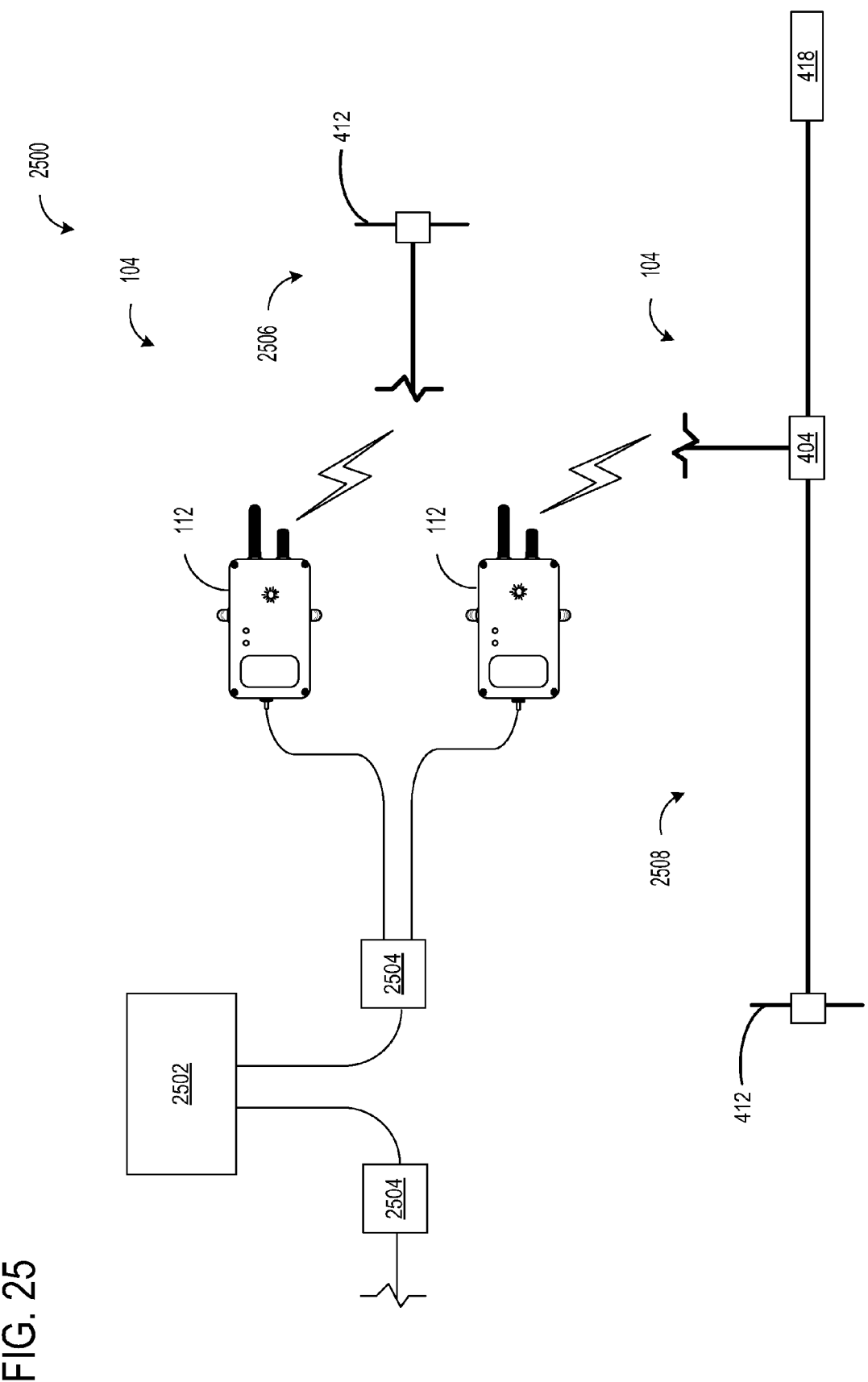
FIG. 25 schematically shows an example DC powered wirelessly-linked RFID reader in accordance with an embodiment of the present disclosure.

Turning briefly to FIG. 25, as an example FIG. 25 shows an embodiment of a DC powered wirelessly-linked RFID reader in an example operating environment 2500. As shown, DC power source 2502 may provide power to RFID readers 112. RFID readers 112 may be connected directly to power source 2502 via junction box 2504. In this way RFID readers 112 receive power to wirelessly communicate with mine radio network 104 in a single antenna system 2506 and/or a distributed antenna system 2508. Alternatively, RFID readers 112 may be in direct communication with single antenna system 2506 and/or distributed antenna system 2508 via a non-radiating cable, for example. It is to be understood that regardless of the antenna system configuration, that an antenna 412 may be configured to pick up RFID tag information and transmit the RFID tag information to RFID readers 112. Further, the antenna systems may be designed in an antenna array for ease of RFID tag pick up.

It is noted that in some embodiments, readers may incorporate an internal battery for backup in case of AC power outage to the AC to DC converter power supply. If the reader is equipped as a battery only unit, such as the example in FIG. 27 below, the user may need to replace the battery as required.

Figure 26:
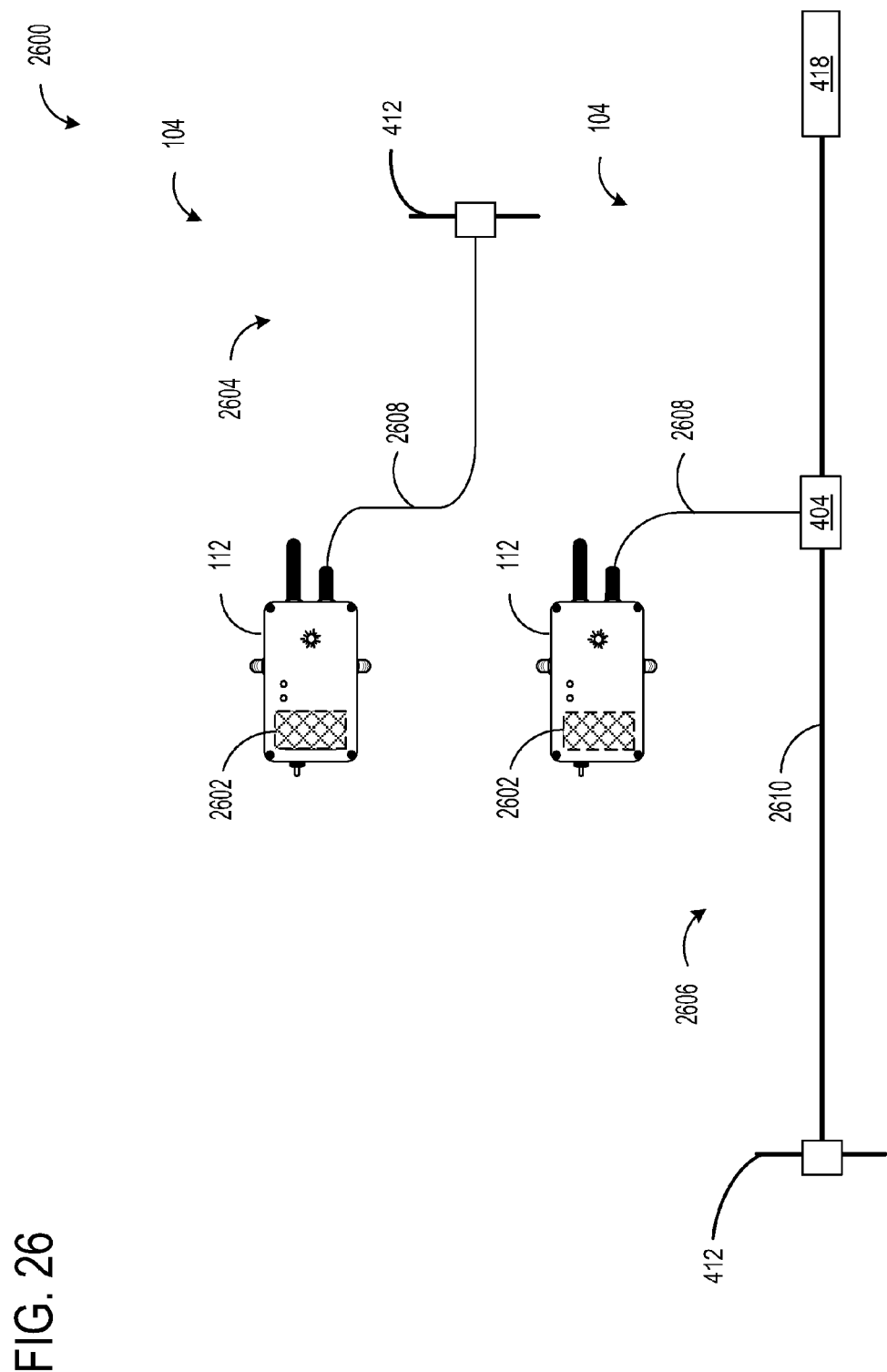
FIG. 26 schematically shows an example battery powered wirelessly-linked RFID reader in accordance with an embodiment of the present disclosure.

As another example, FIG. 26 shows an embodiment of battery powered wirelessly-linked RFID readers 112 in an example operating environment 2600. As shown, a battery 2602 powers each RFID reader 112. In this way, RFID readers 112 receive power to communicate with mine radio network 104. It will be appreciated that an RFID reader 112 may be in communication with a mine radio network 104 via a single antenna system 2604 and/or a distributed antenna system 2606, similar to FIG. 25. In the example shown, RFID readers 112 are communicatively coupled to single antenna system 2604 or distributed antenna system 2606 via non-radiating cable 2608. Further, as shown, distributed antenna system 2606 may include radiating cable 2610.

Figure 27:
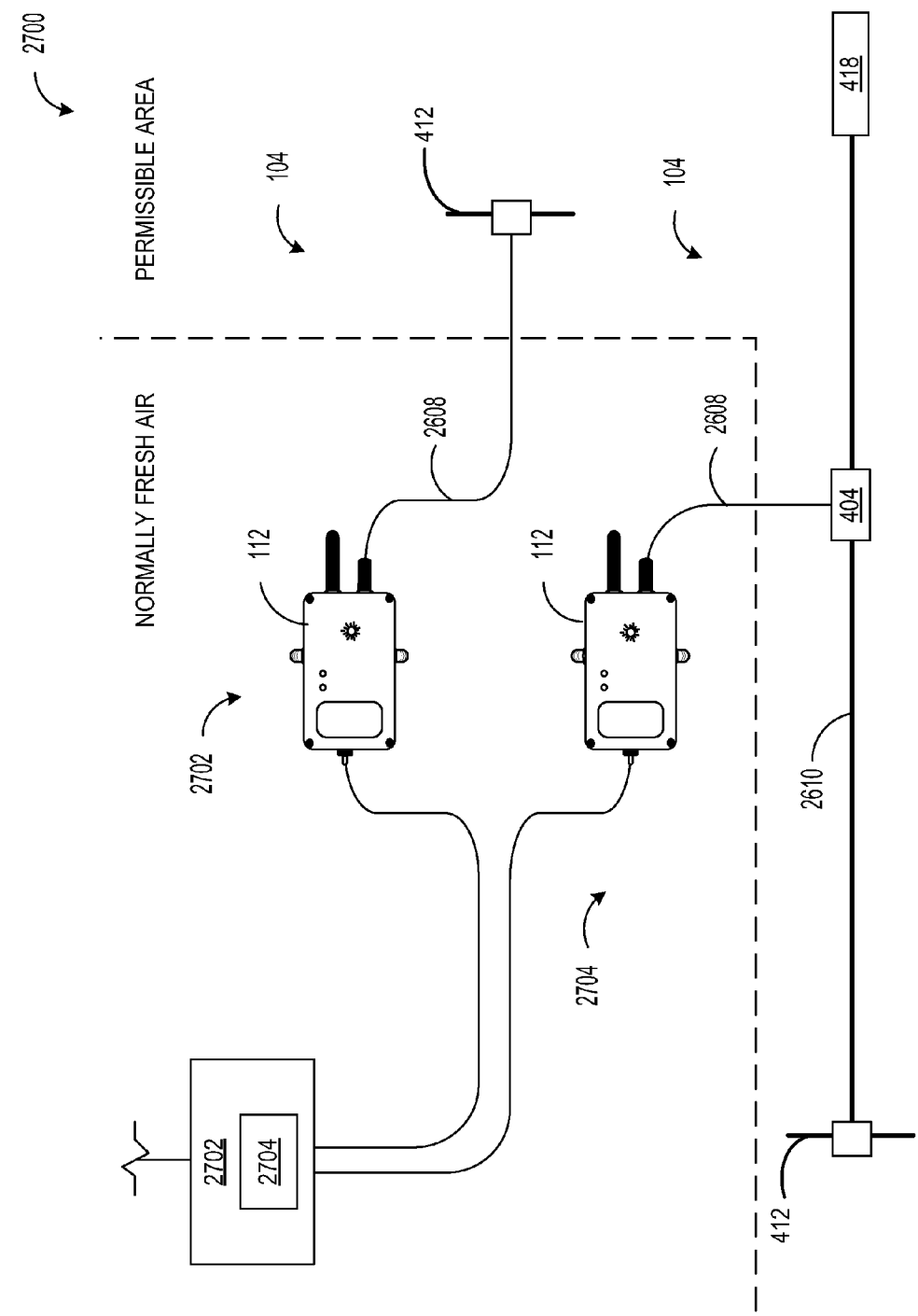
FIG. 27 schematically shows an example DC powered wirelessly-linked RFID reader including a battery backup in accordance with an embodiment of the present disclosure.

As a further example, FIG. 27 shows an embodiment of a DC powered wirelessly-linked RFID reader including a battery backup in an example operating environment 2700. As shown, DC power source 2702, including backup battery 2704, powers each RFID reader 112. In this way, RFID readers 112 receive power to communicate with mine radio network 104. In the example shown, DC power source 2702 and RFID readers 112 may be located within a portion of a mine with normally fresh air. Similar to FIGS. 25 and 26, RFID readers 112 may be in communication with mine radio network 104 via a single antenna system 2706 and/or a distributed antenna system 2708. As shown, single antenna system 2706 and distributed antenna system 2708 may be located within a permissible area of the mine.

It will be appreciated that the example operating environments provided in FIGS. 25-27 are non-limiting and may be used in combination or sub-combination with mine radio network 104. For example, a mine may include some AC/DC powered RFID readers, some battery powered RFID readers and/or some DC powered RFID readers. Further, regardless of the primary power source, each RFID reader may be coupled to a backup battery supply.

Further, it will be appreciated that the power source of the RFID reader may be configured so as to reduce power consumption. In other words, the RFID reader may be configured as a low-powered wirelessly-linked RFID reader. For example, a reduced power consumption configuration may prolong the battery life of an RFID reader, particularly when the RFID reader is operating one or more environmental sensors to sense the immediate environment. As described in more detail below, the one or more environmental sensors may detect methane and/or carbon monoxide or other gas concentrations within the mine.

The environmental sensors may be configured to identify gas conditions which are above or below a threshold level or which are outside a approved range. Further, changes form a stable gas condition may be detected through use of the sensors. It is noted that in some embodiments, wirelessly-linked RFID reader 112 may also include one or more solder-connected "fast blow" fuses providing thermal protection to power supply and/or control circuits. Such fuses may provide compatibility with applicable intrinsic safety (1S) protection techniques for the use of electrical equipment explosive environments.

Turning back to FIG. 2, it will be appreciated that in some embodiments, power supply 236 may share a housing with wirelessly-linked RFID reader 112. For example, the power supply may be a battery (e.g., battery 2602 of FIG. 26), and may therefore share a housing with RFID reader 112. Non-limiting specifications for an example power supply for wirelessly-linked RFID reader 112 are included below in Table 3.

TABLE 3

Example Power Supply Specifications

| | |
|---|---|
| MSHA Approval | Yes |
| Voltage/Amperage/Run Time | 120 VAC/8 VDC/1 Amp/24 hours |
| Battery Type/Voltage | SLA Type 6 VDC @ 12 AH |
| Mechanical | Metal 13" × 17" × 7.5" |
| Cables | MSHA Accepted SOOW - 16/2 or larger |

In some embodiments, and as mentioned above, wirelessly-linked RFID reader 112 may include one or more environmental sensors 250. For example, environmental sensor 250 may be configured to sense one or more of a gas species (such as $CH_4$, CO, O2, SO2 NO2) and/or concentration, temperature, humidity, ambient barometric pressure, etc. Sensed data from environmental sensor 250 may be transmitted as a separate message via mine radio network 104, or reader to reader in full Multi-hop mode. Examples of environmental sensors are discussed in greater detail below with respect to FIGS. 35-36B.

As described above, the RFID reader, may include a tag indicator and/or communication indicator which may illuminate to indicate a status. In some embodiments, wirelessly-linked RFID reader 112 may include one or more indicator lights 252 for providing a visual indication of an online/offline status of wirelessly-linked RFID reader 112, a hazard condition, an evacuation command, etc. For example, a red flashing light may be displayed to indicate a mine evacuation command. In some embodiments, indicator light 252 may be triggered remotely by local server 110 and/or remote server 122. Alternatively or additionally, in some embodiments, indicator light 252 may be triggered by environmental sensor 250 of the corresponding wirelessly-linked RFID reader 112 and/or another networked wirelessly-linked RFID reader 112.

It will be appreciated that one or more indicator lights 252 may be triggered without a triggering event and/or command from a radio dispatch, thereby minimizing a delay to prompt an evacuation. For example, indicator lights 252 may be triggered by an environmental sensor 250 before the environmental sensor metadata is transmitted to a network at surface 132. Such a triggering event may be associated with different indicator light modes and/or alarms depending on the severity of the environmental sensor reading, wherein the severity may be defined by one or more thresholds.

For example, indicator lights 252 may flash corresponding to a range of detected methane concentrations, wherein a lower concentration of methane surpassing one threshold may trigger indicator lights 252 to flash faster relative to a higher concentration of methane surpassing a second threshold greater than the first threshold.

Further, a triggering event may need to pass one or more checkpoints before indicator lights 252 are activated. For example, to minimize the likelihood of a false alarm, indicator lights 252 may be triggered after more than one environmental sensor 250 transmits environmental metadata that surpasses a threshold and/or more than one substance, variable and/or condition is sensed above a threshold. It will be appreciated that indicator lights 252 may operate in different modes, including flashing at different speeds, flashing different colors, sound and vibration combination indications, etc. For example, indicator lights 252 may indicate the severity of a situation by flashing at different frequencies and/or the number of indicator lights flashing may correspond to the severity of a situation.

Moving to FIG. 3, FIG. 3 schematically shows an example tracking headend interface unit 108 in communication with local server 110. In some embodiments, tracking headend interface unit 108 may communicate with local server 110 via a serial and/or universal serial bus (USB) connection. Additionally or alternatively, in some embodiments, tracking headend interface unit 108 may communicate with local server 110 via a wireless network connection and/or an Ethernet network connection. For example, in one scenario, an Internet Protocol (IP) to serial interface converter may be used for communication. In another scenario, an RS-232 to RS-485 converter may be used for communication. Thus, it will be appreciated that any suitable communication scheme may be used for communication between tracking headend interface unit 108 and local server 110 within the scope of the present disclosure.

Transmission of tag information 204 is routed through mine radio network headend 106 and received at tracking headend interface unit 108, indicated generally by arrow 300. Tracking headend interface unit 108 controls and coordinates communications between local server 110 and mine radio network headend 106. In some embodiments, tracking headend interface unit 108 is connected to mine radio network headend 106 using transmit (Tx) and receive (Rx) ports with one or more coaxial cables and to local server 110 with one or more RS232 cables.

Figure 24:
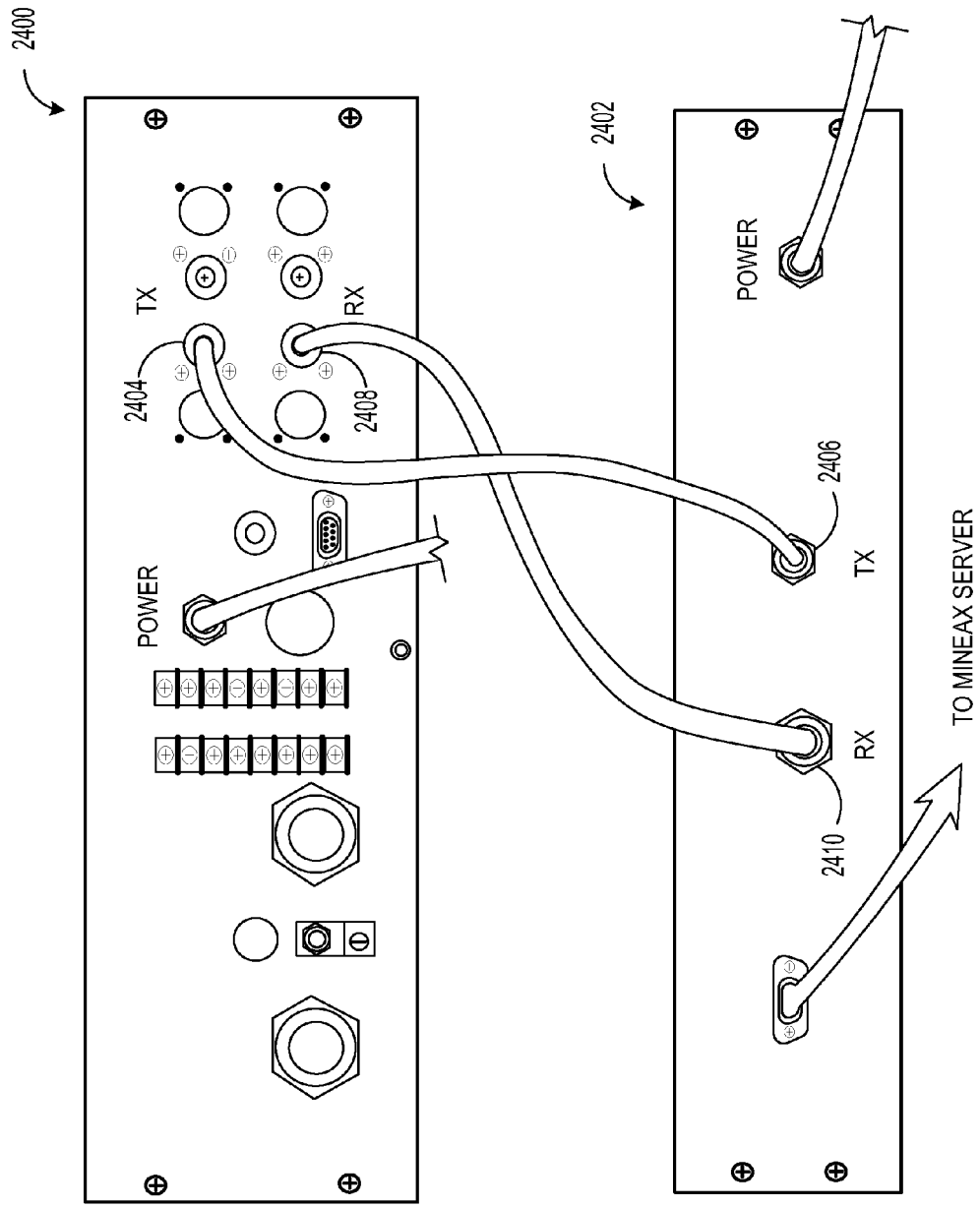
FIG. 24 schematically shows example connections between an example tracking headend interface unit and an example mine radio network headend in accordance with an embodiment of the present disclosure.

As an example, FIG. 24 schematically shows example connections between an example mine radio network headend 2400 and an example tracking headend interface unit 2402. As shown, Tx port 2404 of mine radio network headend 2400 may be coupled to Tx port 2406 of tracking headend interface unit 2402. Further, Rx port 2408 of mine radio network headend 2400 may be coupled to Rx port 2410 of tracking headend interface unit 2402. It will be appreciated that mine radio network headend 2400 and tracking headend interface unit 2402 may include additional ports for communicating with other devices. As such, it will be appreciated that FIG. 24 is provided by way of example and is not meant to be limiting.

Figure 8:
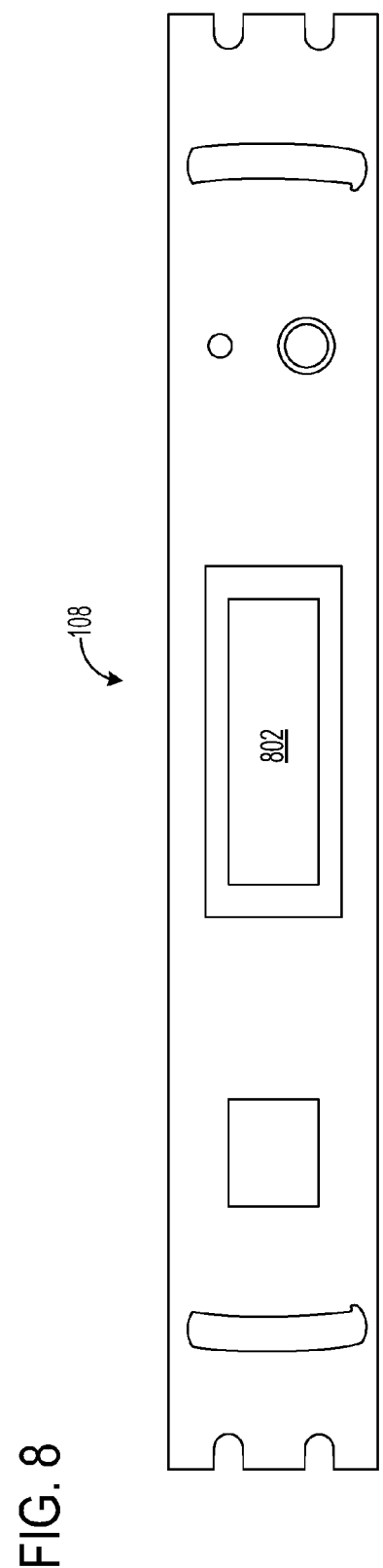
FIG. 8 shows an example of a tracking headend interface unit in accordance with an embodiment of the present disclosure.

Turning back to FIG. 3, tracking headend interface unit 108 is a computing device including a memory 302, a processor 304, and mass storage 306. In some embodiments, mass storage 306 may be a hard disk and/or a removable mass storage device, such as a USB flash drive. FIG. 8 shows another example of tracking headend interface unit 108 including display 802.

Again in reference to FIG. 3, in some embodiments, tracking headend interface unit 108 may include a backup power supply 308, which may permit continued operation of tracking headend interface unit 108 during a power failure condition. In some embodiments, backup power supply 308 may be a DC power supply. Non-limiting specifications for an example tracking headend interface unit 108 are included in Table 4 below.

TABLE 4

Example Tracking Headend Interface Unit Specifications

| | |
|---|---|
| Voltage | 120 VAC input to 12 VDC with Battery/fused |
| DC Current/RF Connections | 200 mA, typical/BNC to Mine Head Unit |
| Data Connections/Memory | RS-232/DB9/Internal USB with 4 GB BU |
| Display | LCD |
| Dimensions | 19" × 3.5" × 12" Rack unit |

Once transmitted from mine radio network 104 to tracking headend interface unit 108, tag information 204 is received at local server 110. Local server 110 facilitates local control and configuration of wirelessly-linked RFID tracking system 100 via user interface module 322, as described in more detail below. In some embodiments, local server 110 may regularly transmit a polling command to wirelessly-linked RFID readers 112 to instruct wirelessly-linked RFID readers 112 to transmit stored tag information 204. However, it will be appreciated that any suitable transmission scheme may be employed. For example, local server 110 may receive transmissions from wirelessly-linked RFID readers 112 in real time, at predetermined intervals, etc.

Local server 110 includes memory 320, a processor 340, and mass storage 342. In some embodiments, local server 110 may include a backup power supply 346, which may permit continued operation of local server 110 during a power failure condition. Further, in some embodiments, local server 110 may be operatively coupled to a printer 380 for printing output from wirelessly-linked RFID tracking system 100. Printer 380 may be coupled to local server 110 via a direct connection and/or via network 120.

In some embodiments, local server 110 may be operatively coupled to a wireless router 370. For example, wireless router 370 may be coupled to local server 110 by a local area network (LAN) port of local server 110. Wireless router 370 may provide input and output functionality for wirelessly-linked RFID tracking system 100 via a client device 390, which may include a client user interface 392. This may provide users with convenient mobile access to one or more features of wirelessly-linked RFID tracking system 100. For example, a mine dispatcher may have continuous access to miner location information via client device 390 without being constrained to a control room. In the embodiment depicted in FIG. 3, client device 390 communicates with wireless router 370 via network 120. In some embodiments, client device 390 may be a mobile computing device, such as a PDA, a tablet computer, or a wireless phone, though it will be appreciated that any suitable client device 390 may be employed within the scope of the present disclosure.

As mentioned above, local server 110 may include user interface module 322. User interface module may be stored in mass storage 342 and loaded into memory 320 for execution on processor 340. User interface module 322 may facilitate configuration and operation of wirelessly-linked RFID tracking system 100, including RFID tags 114 and wirelessly-linked RFID readers. User interface module 322 may include various modules for configuring, maintaining, and operating wirelessly-linked RFID tracking system 100.

As an example, user interface module 322 may include a graphical user interface. In some embodiments, the graphical user interface may be presented on display 344 of local server 110. Display 344 may be any suitable display device in electrical communication with local server 110. In some embodiments, display 344 may be a standalone display monitor, though display 344 is not limited to such embodiments.

Further, user interface module 322 may provide one or more graphical user interface elements, such as a soft-keys, drop-down menus, fields, etc. For example, activation of a soft-key may cause a radio signal to be transmitted via mine radio network 104 instructing one or more wirelessly-linked RFID readers 112 to illuminate and/or flash an indicator light (e.g. indicator light 252 of FIG. 2), which may provide a visual evacuation alarm.

Figure 9:
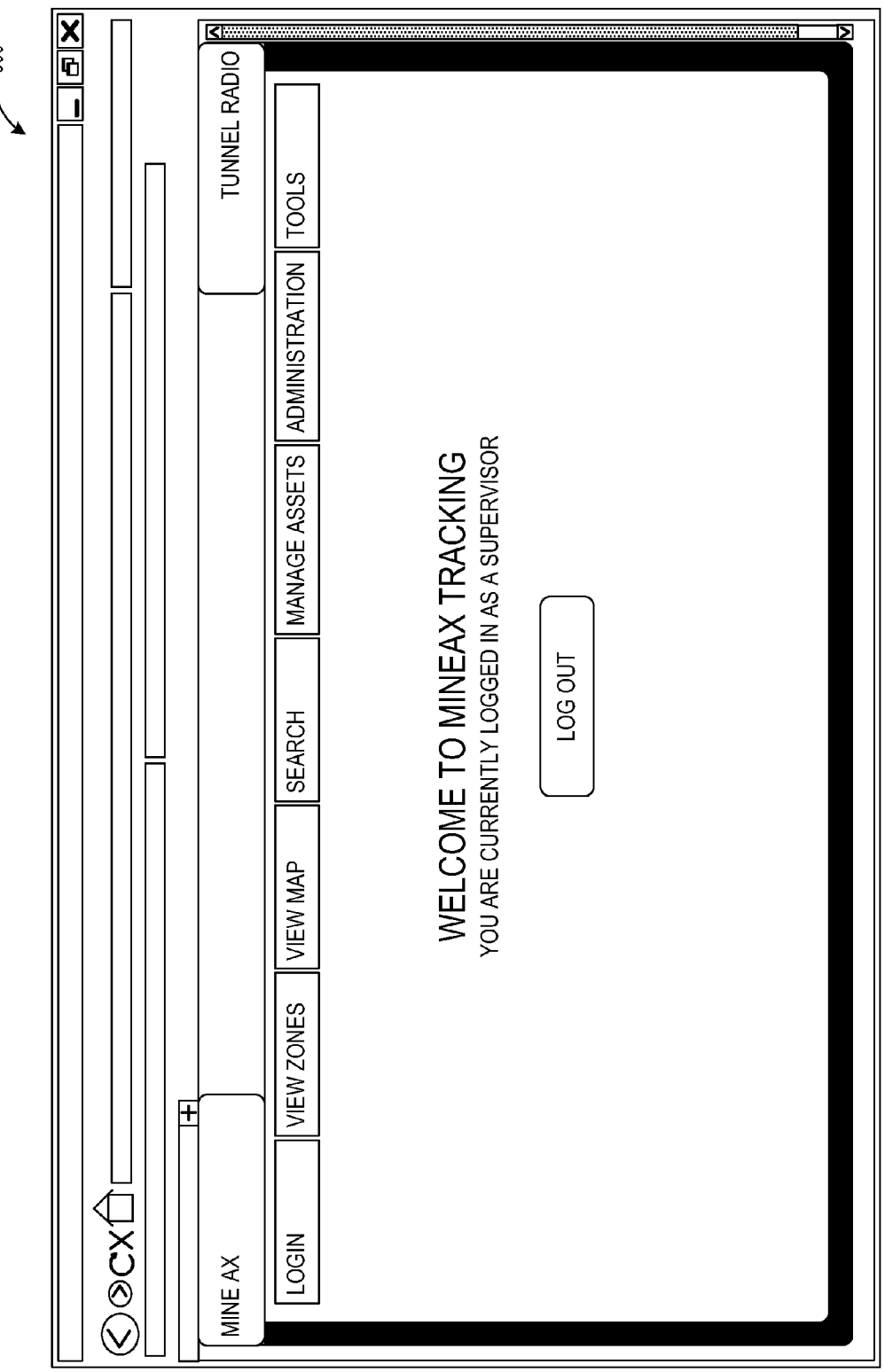
FIG. 9 shows an example login graphical user interface in accordance with an embodiment of the present disclosure.

FIGS. 9-22 show various example graphical user interfaces that user interface module 322 may be configured to output to a display. For example, FIG. 9 shows an example login graphical user interface 900 depicting a login screen of user interface module 322 and various tabs associated with other graphical user interface elements. In some embodiments, user access to the various modules of user interface module 322 may be granted or denied based on configurable permission settings. For example, a system administrator may grant various viewing and editing permissions to system users to maintain data security, system integrity, etc.

In some embodiments, user interface module 322 may include a notification module 324. Notification module 324 may notify a user of status information for various RFID tags 114 deployed in wirelessly-linked RFID tracking system 100. For example, notification module 324 may provide graphical and/or tabular information about location, time, and environmental information included in tag information 204 from various RFID tags 114 throughout mine 102.

Figure 10:
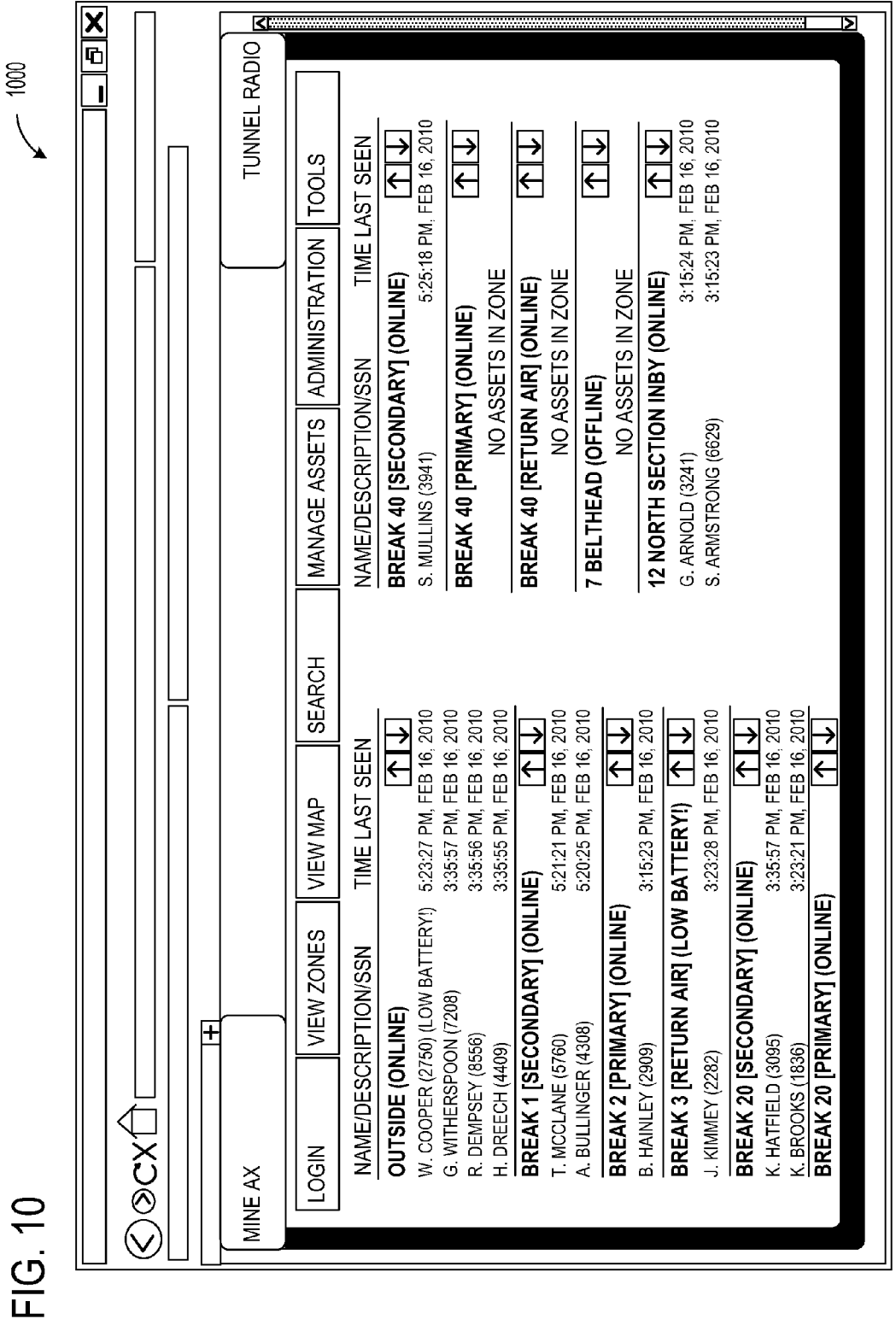
FIG. 10 shows an example display of location and time information in accordance with an embodiment of the present disclosure.

To illustrate, FIG. 10 shows an example display 1000 of location and time information for various users' RFID tags 114. In some embodiments, notification module 324 may present summary location status information via the graphical user interface. For example, the graphical user interface may display lists of which RFID tags have an "In Mine" (e.g., Break 1, Break 2, Break 3, Break 20, Break 40, 7 Belthead, and 12 North Section Inby may be RFID reader aliases that may indicate an "in mine" status for users with an RFID tag within a reception zone of the respective RFID reader) and/or an "Outside" location status. This may confirm a location of those personnel who have evacuated from a mine and those remaining in the mine during an emergency evacuation situation.

In some embodiments, a list of wirelessly-linked RFID readers 112 may be provided in a graphical and/or a tabular format, which may include an online/offline status information for each reader as well as a list of RFID tags 114 detected by the corresponding reader. In some embodiments, an online/offline status may be indicated by a color status identifier, e.g. a green status identifier may be used for online status and an offline status may be indicated by a red status identifier. For example, FIG. 10 shows an example display 1000 of online/offline status notifications for various wirelessly-linked RFID readers.

Figure 11:
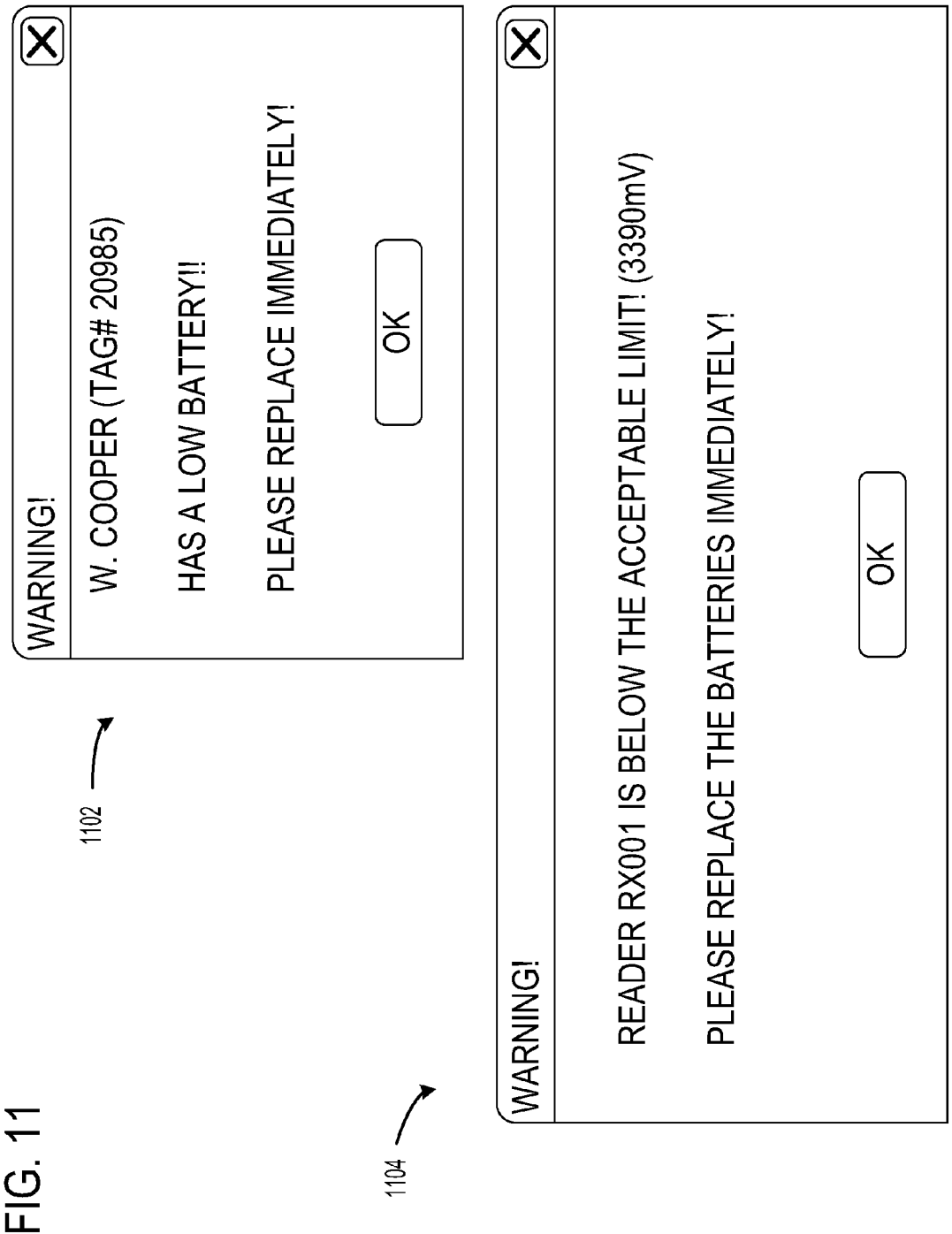
FIG. 11 shows an example tag alert display and an example reader alert display in accordance with an embodiment of the present disclosure.

In some embodiments, alert and/or warning information about individual RFID tags 114 may be provided by notification module 324. For example, a warning message may be displayed indicating that a specific RFID tag has a low battery. FIG. 11 shows an example tag alert display 1102 indicating that an RFID tag 114 has a low battery 214. Further, in some embodiments, notification module 324 may present alert and/or warning information about various wirelessly-linked RFID readers 112 deployed throughout mine 102. For example, a low battery warning may be displayed for a wirelessly-linked RFID reader nearing the end of a battery life of battery 214. FIG. 11 shows an embodiment of a reader alert display 1104 indicating that an RFID reader has a low battery.

Figure 12:
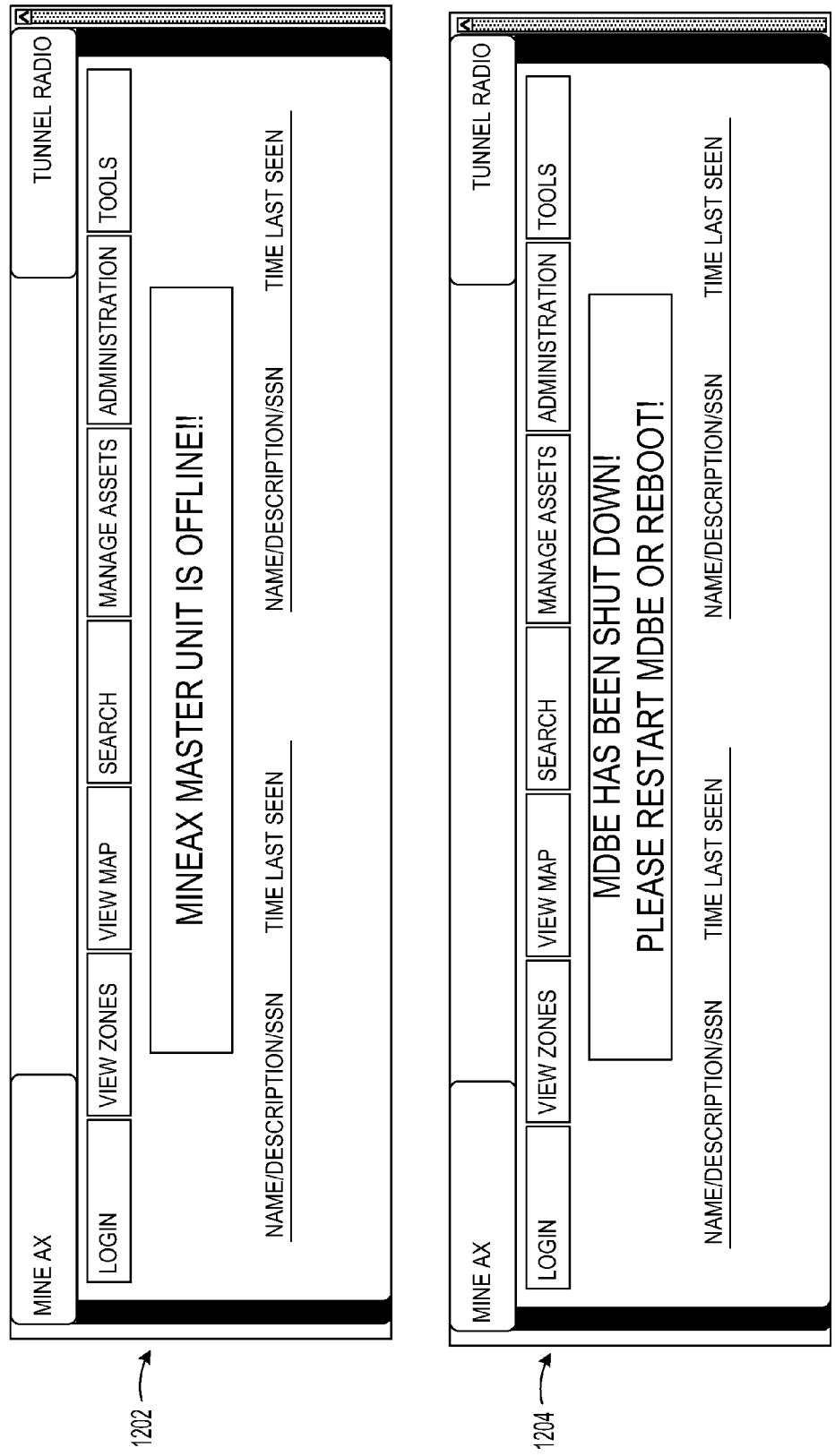
FIG. 12 shows an example communication alert display and an example data collection alert display in accordance with an embodiment of the present disclosure.

In some embodiments, notification module 324 may present one or more alert and/or warning messages regarding communication problems between local server 110 and tracking headend interface unit 108. For example, FIG. 12 shows an example communication alert display 1202 indicating a communication problem between local server 110 and tracking headend interface unit 108. Further, in some embodiments, notification module 324 may present one or more of an alert and/or a warning message regarding data collection errors associated with capturing and/or storing tag information 204. FIG. 12 further shows an example data collection alert display 1204 indicating a data collection problem.

In some embodiments, notification module 324 may send alerts and/or notifications to users via email, text message, voice message, etc. For example, if wirelessly-linked RFID reader 112 is in an offline state for a specified duration, notification module 324 may send an email message to a list of specified recipients. Such alerts may be sent from local server 110 via network 120, to remote server 122A, remote server 122B, client device 392, etc as shown in FIG. 3. It will be appreciated that any suitable scheme of sending such alerts may be employed.

Figure 13:
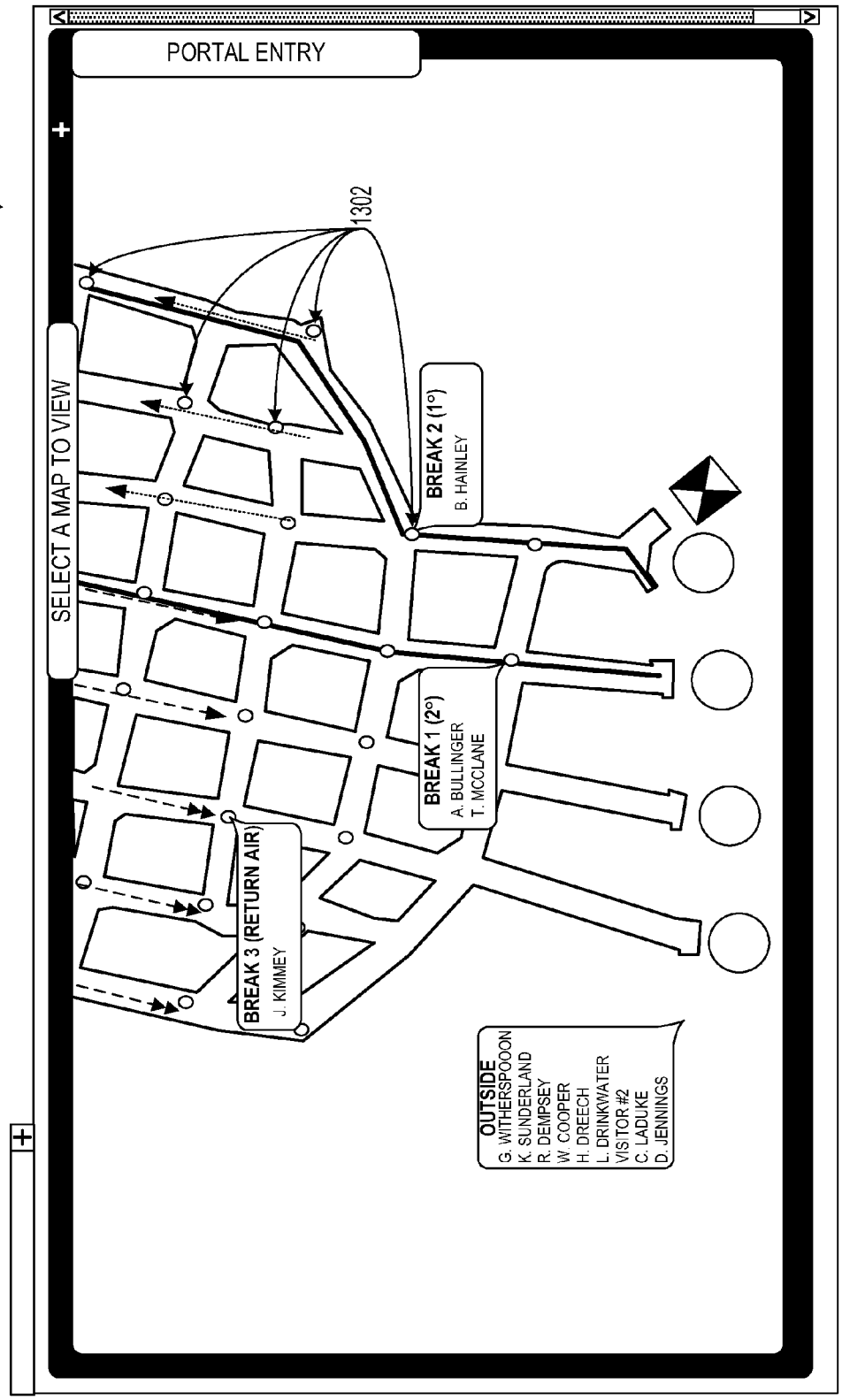
FIG. 13 shows an example graphical map view in accordance with an embodiment of the present disclosure.

In some embodiments, user interface module 322 may include a map module 326, as shown in FIG. 3. Map module 326 may present one or more graphical map views of various levels and/or sections of mine 102 via the graphical user interface. FIG. 13 shows an example graphical map view 1300, including location markers 1302 for various wirelessly-linked RFID readers 112 and various RFID tags 114 arranged about graphical map view 1300. In some embodiments, graphical map view 1300 may be generated from and/or overlaid on a user-supplied map. For example, in one scenario, graphical map view 1300 may be imported from a user-supplied map in a portable document format (PDF). In another scenario, a user-supplied map may be a computer-aided drafting (CAD) file such as a .DXF or a .DWG converted to a PDF or JPEG format.

In some embodiments, location markers 1302 may provide additional information about various RFID tags 114, such as a low battery status. Further, in some embodiments, the above-described alarm and/or notification information provided by notification module 324 may be presented on graphical map view 1300.

Figure 14:
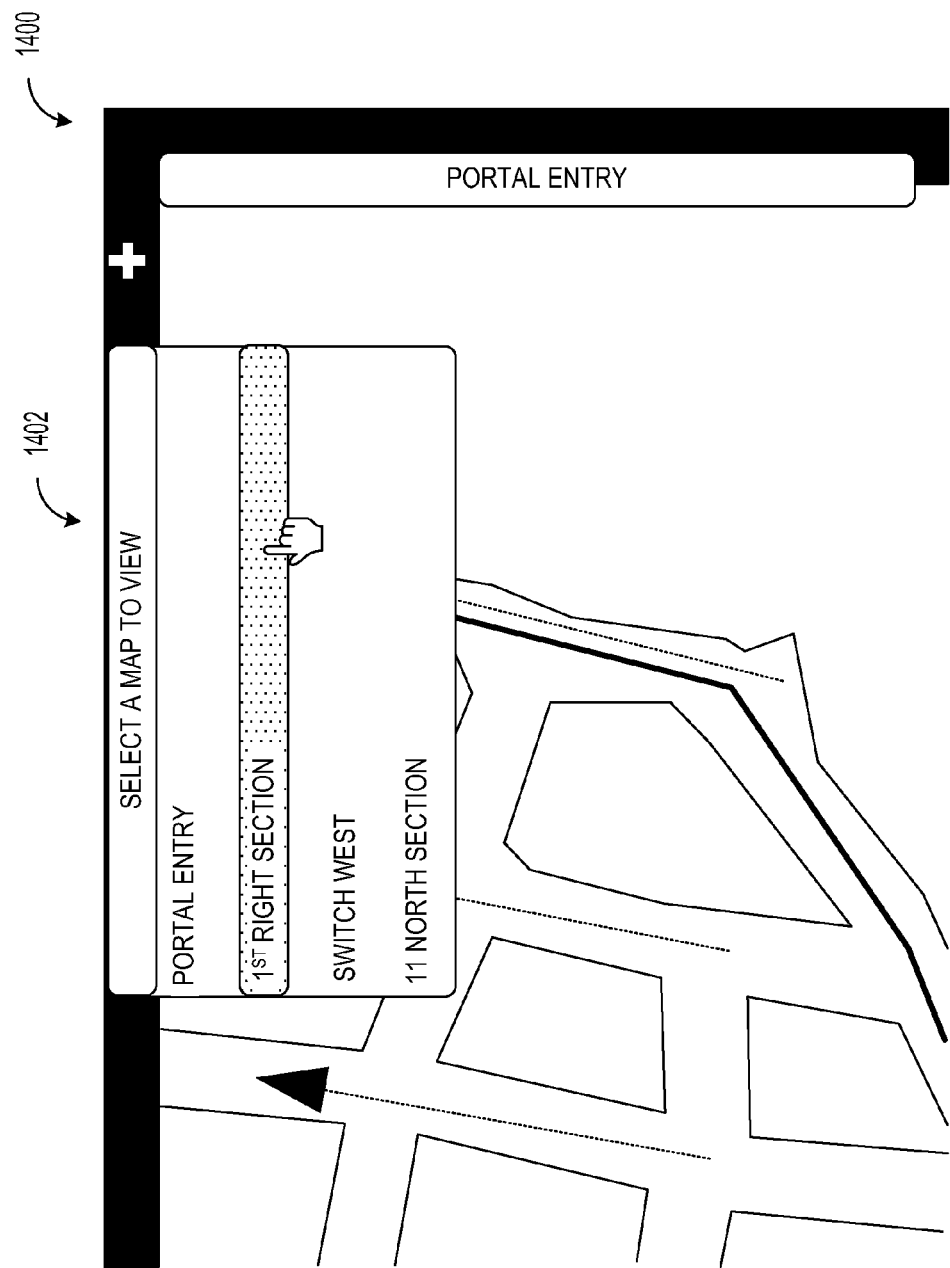
FIG. 14 shows another example graphical map view in accordance with an embodiment of the present disclosure.

In some embodiments, the graphical map view may include one or more graphical user interface elements configured to allow a user to expand, shrink, and/or select a portion of the graphical map view. For example, FIG. 14 shows an example graphical map view 1400 including a dropdown menu 1402 presenting such graphical user interface elements. As described above, in some embodiments, such mine or facility drawings or maps may be imported to the user software in PDF or CAD .DXF or .DWG files converted to PDF or in JPEG format. In some embodiments, the graphical user interface may include one or more graphical user interface elements for configuring the graphical map view. For example, a tool bar may be presented including graphical user interface elements for overlaying symbols and/or icons related to the wirelessly-linked RFID tracking system (e.g., wirelessly-linked RFID readers, RFID tags and/or tag information, etc.). This may allow symbols and icons relating to readers and/or radio network components to be overlaid onto said drawings for interactive use.

Additionally or alternatively, in some embodiments, other mine utilities or items may also be overlaid in a similar manner, such as electrical power centers, pumps, fans or other systems that may be useful to control or monitor using the RFID network and computer interface with suitable remote radio interface modules. Thus, it will be appreciated that any suitable symbols and/or icons may be included in the graphical map view in any suitable way within the scope of the present disclosure.

Figure 15:
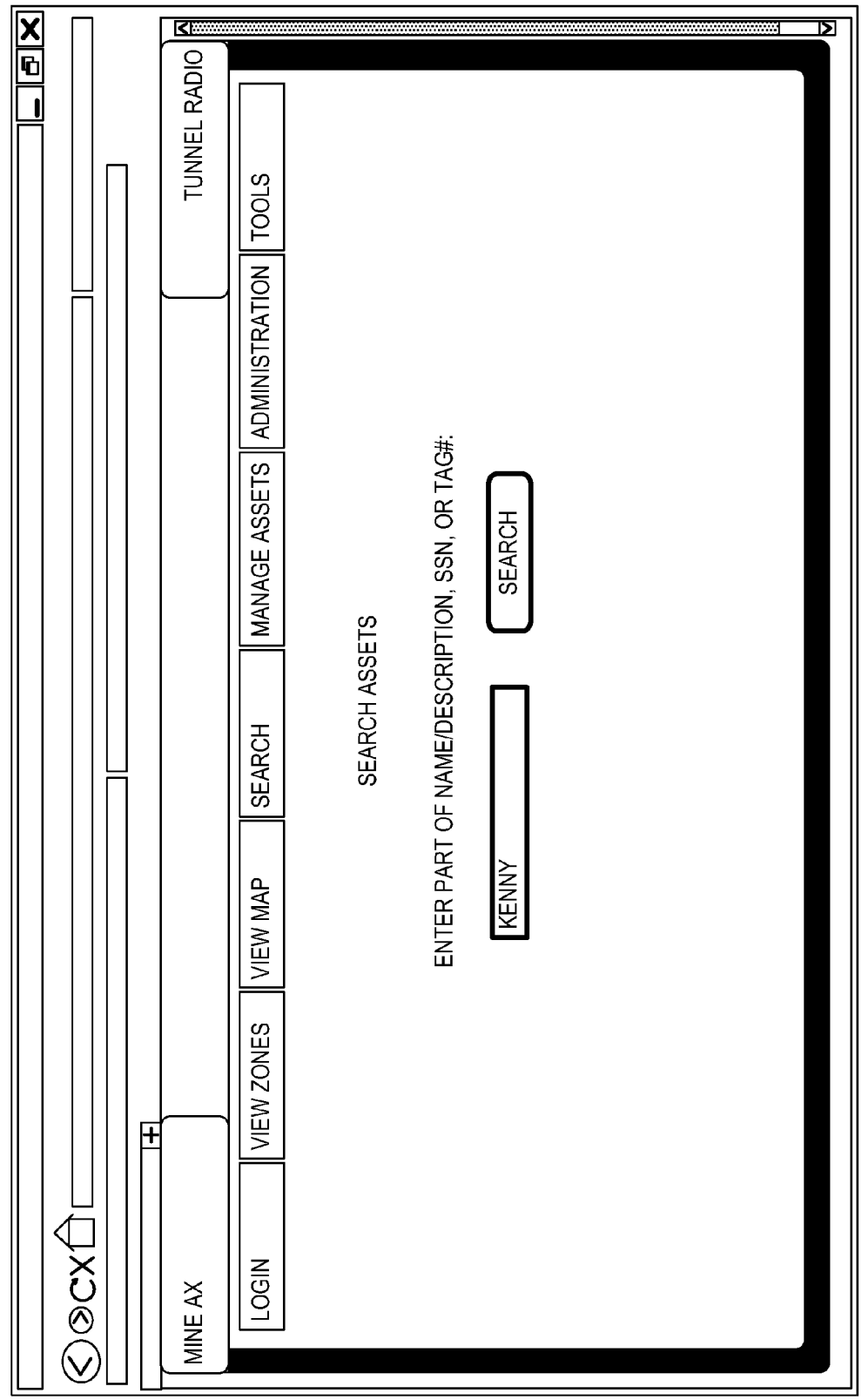
FIG. 15 shows an example search utility graphical user interface in accordance with an embodiment of the present disclosure.
Figure 16:
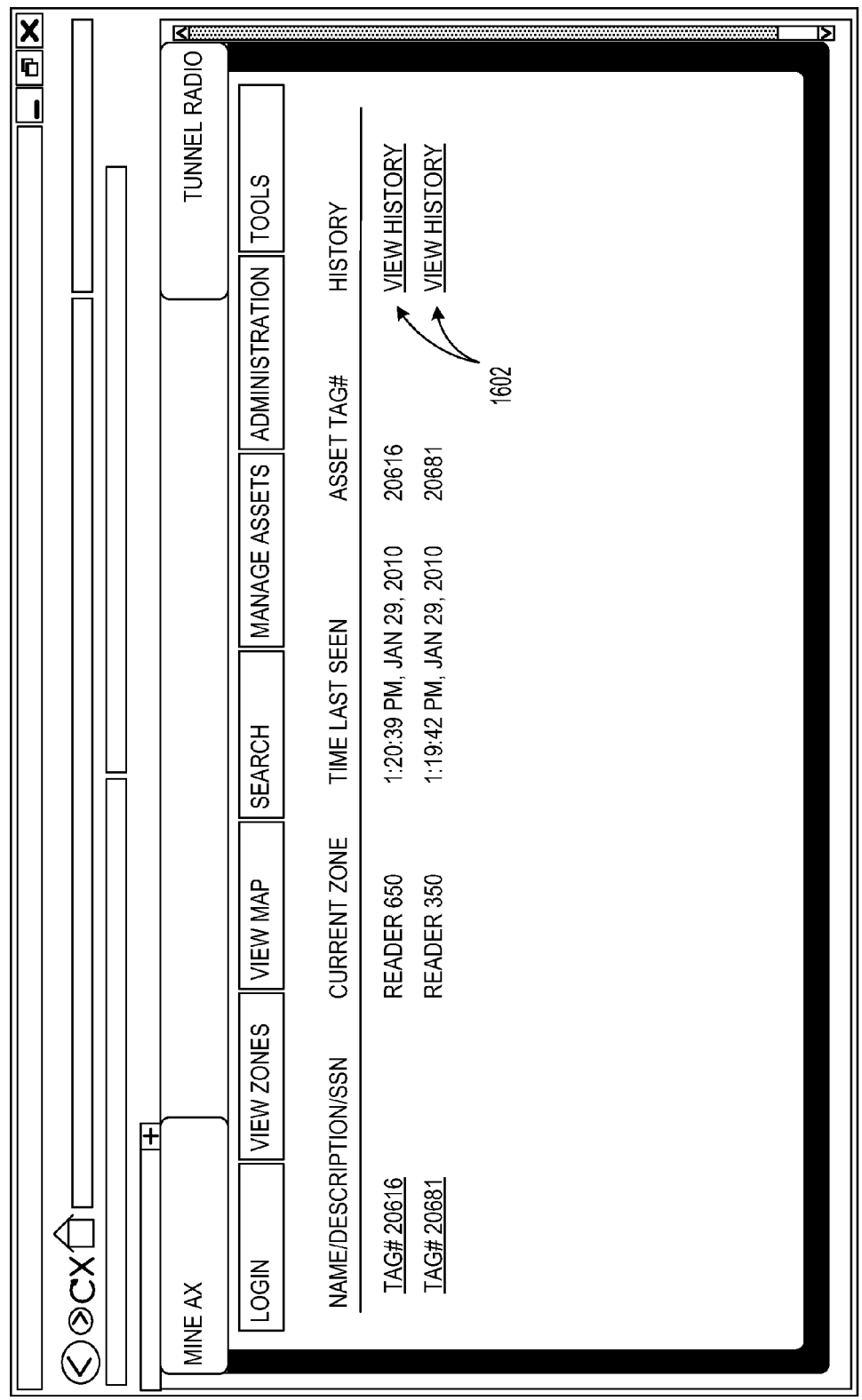
FIG. 16 shows an example search results display in accordance with an embodiment of the present disclosure.

In some embodiments, user interface module 322 may include a search module 328, as shown in FIG. 3. Search module 328 may provide a search utility allowing a user to search for information about a person bearing an RFID tag 114. For example, FIG. 15 shows an example search utility graphical user interface 1500. In the example shown in FIG. 15, a search for "Kenny" is being executed. FIG. 16 shows an example search results display 1600 indicating where RFID tags associated with Kenny are currently located with respect to an RFID reader, when the RFID tags were last detected, and what the RFID tag asset numbers are.

Figure 17:
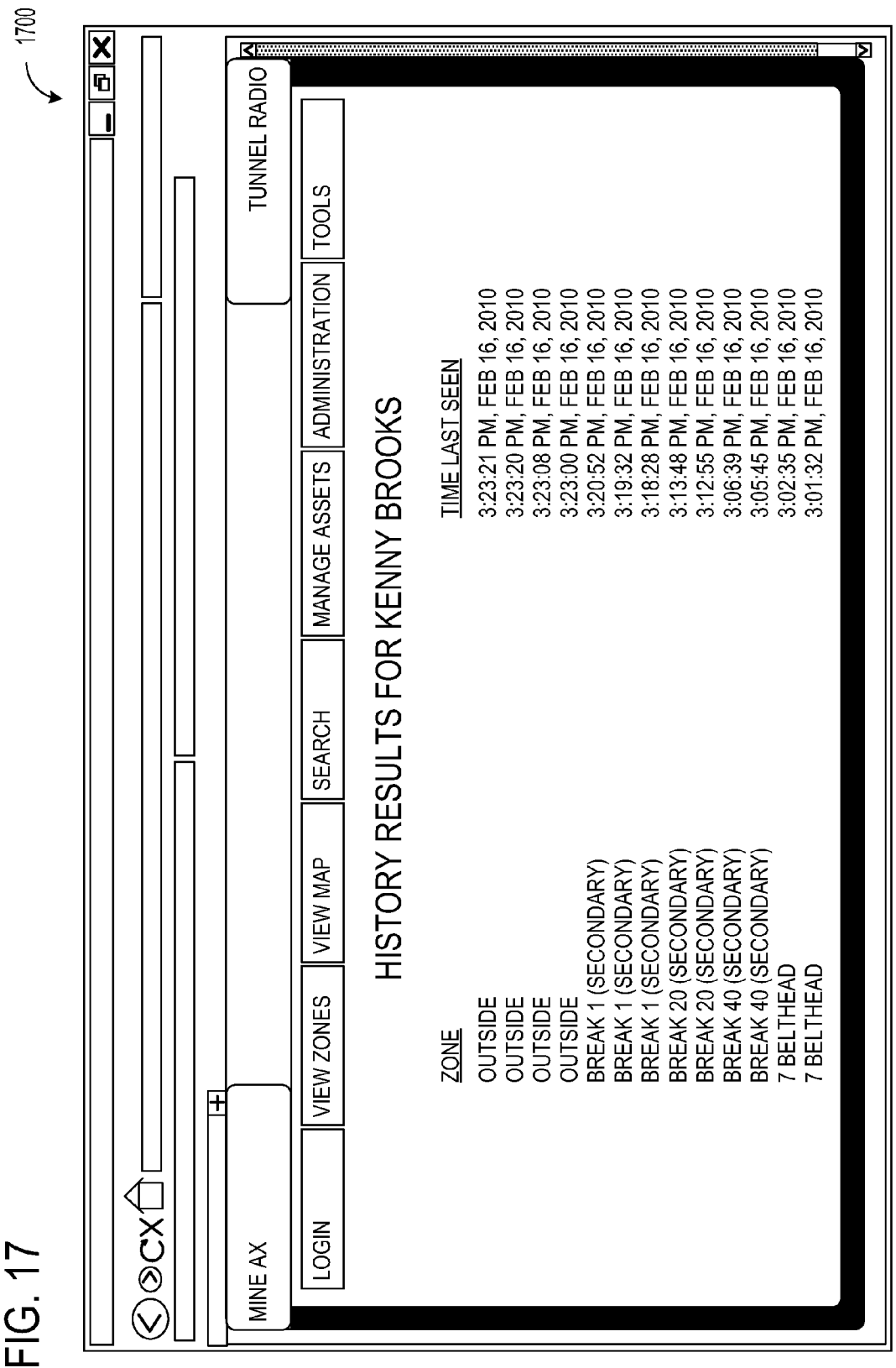
FIG. 17 shows an example history display in accordance with an embodiment of the present disclosure.

In some embodiments, historical information may also be retrieved via search module 328. In the example shown in FIG. 16, hyperlinks 1602 to a zone history of the displayed tags are displayed in response to the search for "Kenny." FIG. 17 shows an example history display 1700 for a tag associated with Kenny.

Figure 18:
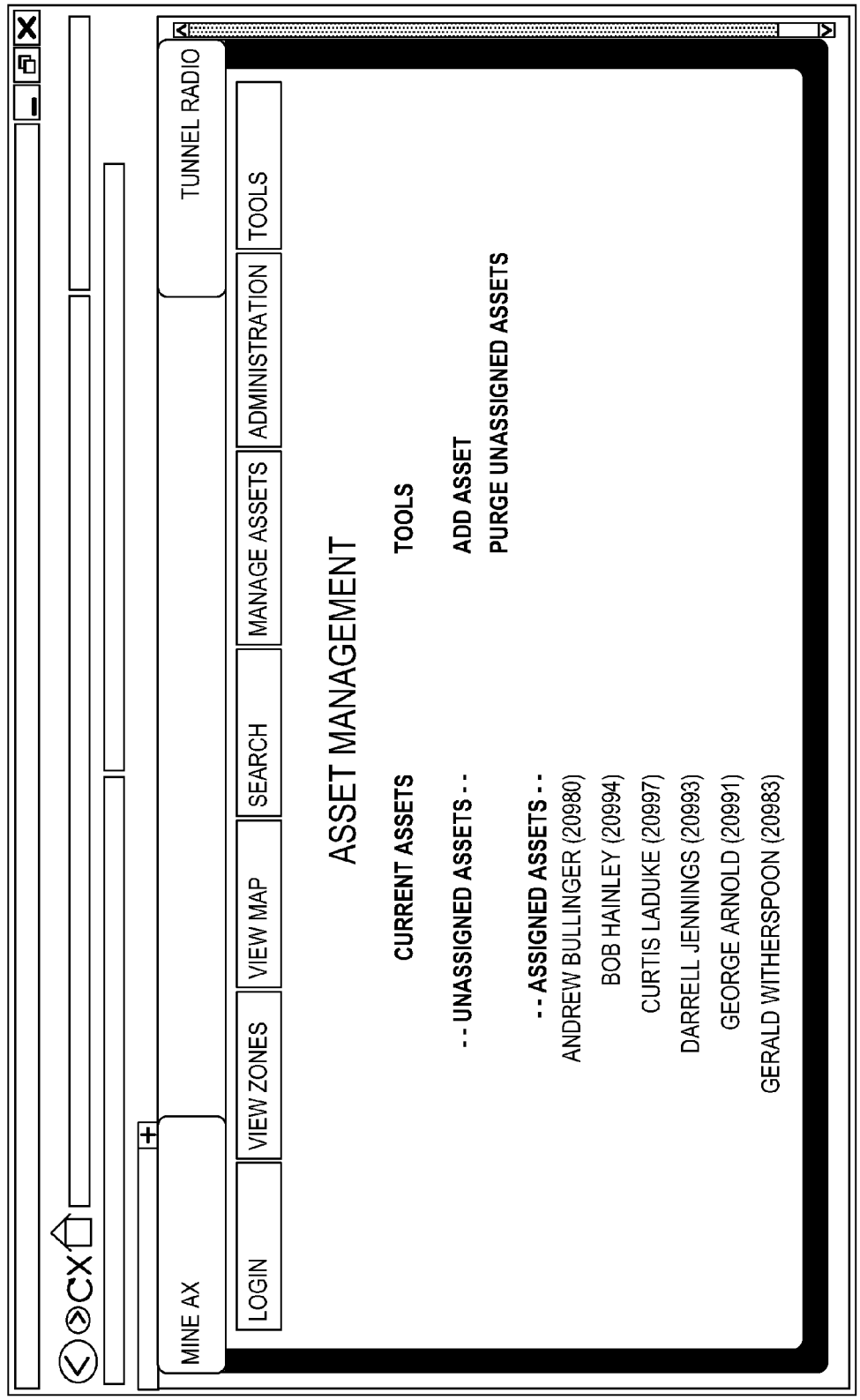
FIG. 18 shows an example asset tag management graphical user interface in accordance with an embodiment of the present disclosure.

In some embodiments, user interface module 322 may include an RFID tag management module 330, as shown in FIG. 3. RFID tag management module 330 may provide one or more user interfaces for configuring various RFID tags 114. For example, RFID tag management module 330 may allow a user to assign and/or delete employee information for a new and/or existing RFID tag 114, may allow a user to update maintenance records for various RFID tags 114, etc. Further, tools may be provided that allow a user to issue RFID tags 114 to users, enter RFID tags 114 into a tag tracking database, configure tag information 204 for an RFID tag 114, etc. For example, FIG. 18 shows an example asset tag management graphical user interface 1800 configured to permit a user to view management information for various RFID tag assets. In some embodiments, RFID tags may be classified as "assigned" or "unassigned." In the example shown in FIG. 18, lists of currently assigned and unassigned assets are displayed, and tools for adding assets and purging assets are provided.

Figure 19:
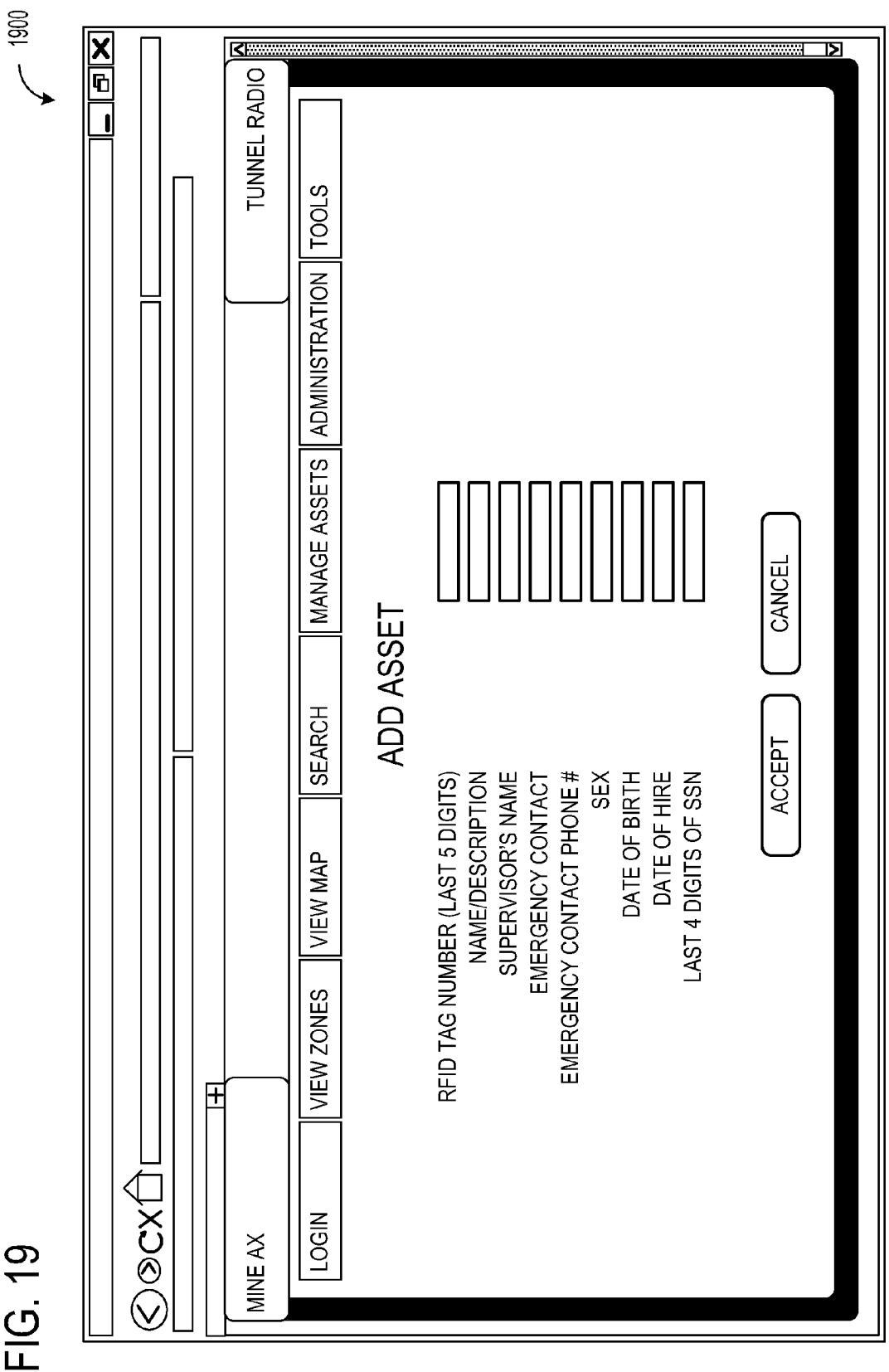
FIG. 19 shows an example asset addition graphical user interface in accordance with an embodiment of the present disclosure.
Figure 20:
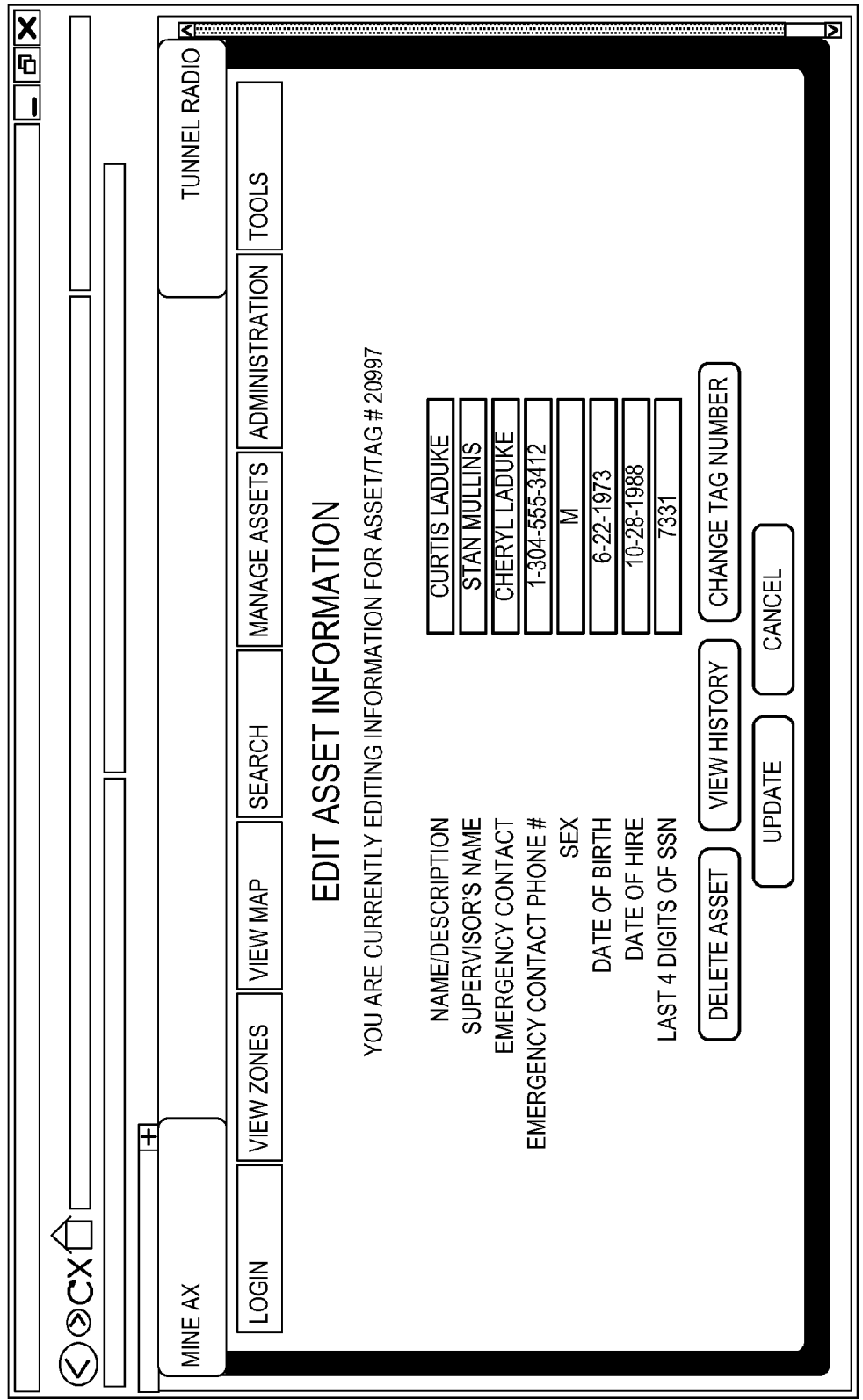
FIG. 20 shows an example asset editor graphical user interface in accordance with an embodiment of the present disclosure.

In some embodiments, wirelessly-linked RFID tracking system 100 may automatically discover recently added RFID tags 114, which may initially be classified as "unassigned." Further, subsequent assignment of an unassigned RFID tag 114 to a user may result in the RFID tag 114 being reclassified as "assigned." Additionally or alternatively, in some embodiments, RFID tag management module 330 may provide tools to add one or more RFID tags 114 to a database before they are automatically discovered by a wirelessly-linked RFID reader 112. For example, FIG. 19 shows an example asset addition graphical user interface 1900 configured to permit user addition of one or more RFID tags 114 to an RFID tag asset pool. Further, FIG. 20 shows an example asset editor graphical user interface 2000 configured to permit user edits to tag information 204 of RFID tag 114.

Again referring back to FIG. 3, in some embodiments, user interface module 322 may include a reader management module 332 configured to manage various wirelessly-linked RFID readers 112 deployed throughout wirelessly-linked RFID tracking system 100. In some embodiments, a user may be able to add and/or delete reader "zones" corresponding to detection zones associated with each wirelessly-linked RFID reader 112. For example, a reader identifier may be configured for a wirelessly-linked RFID reader using reader management module 332. In one scenario, a wirelessly-linked RFID reader having a reader identifier "7106" may be assigned an alias associated with a location in a mine of the wirelessly-linked RFID reader, such as "SECTION 6 LEFT."

Figure 21:
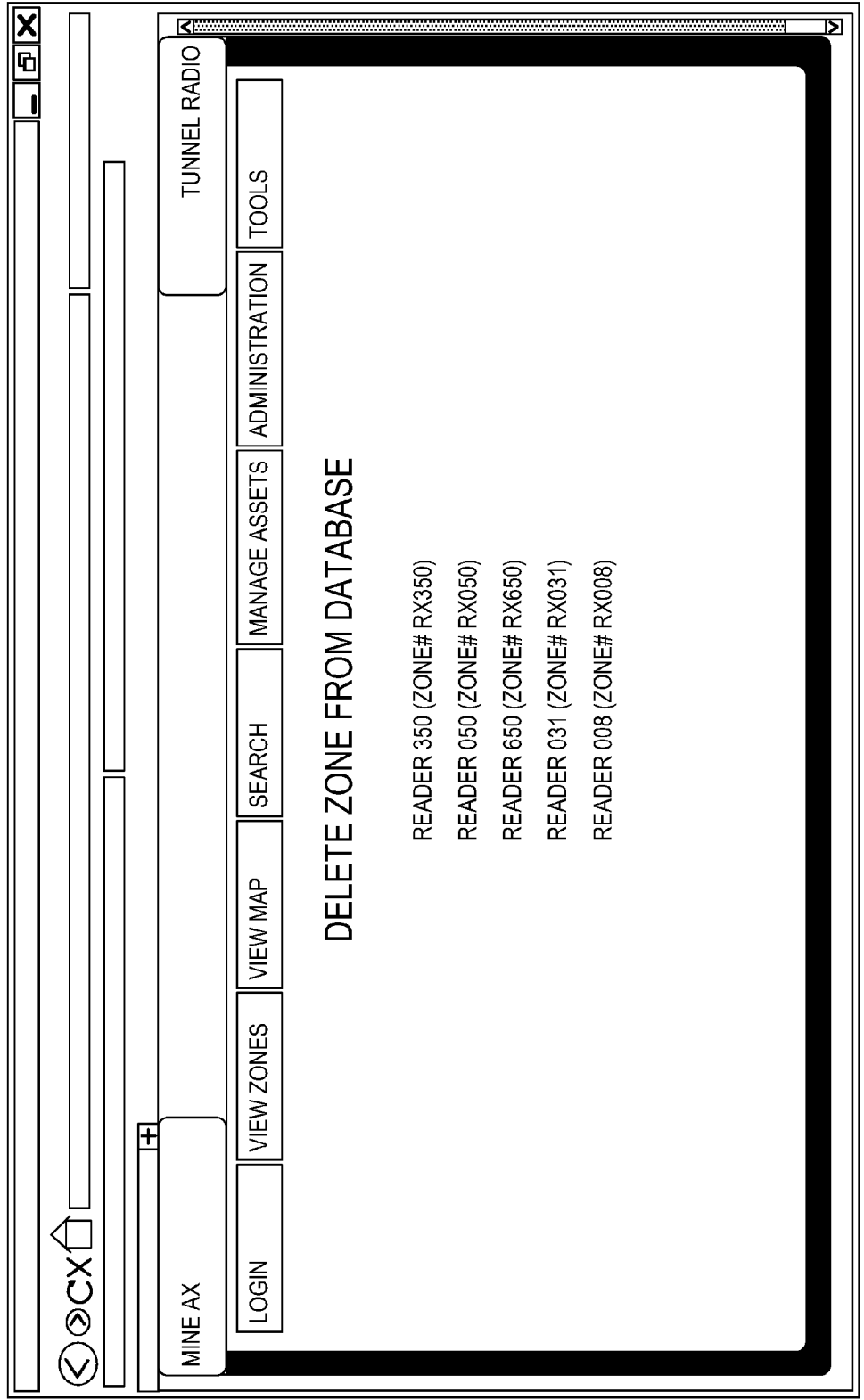
FIG. 21 shows an example reader management graphical user interface in accordance with an embodiment of the present disclosure.

FIG. 21 shows an example reader management graphical user interface 2100, which may be used to delete a reader "zone" that is not in use. It will be appreciated that similar graphical user interfaces may be provided to permit addition of new reader zones, etc. Additionally or alternatively, in some embodiments, wirelessly-linked RFID tracking system 100 may programmatically add a reader zone and/or update a status of a reader zone to "online" upon detection of an RFID tag by the corresponding wirelessly-linked RFID reader 112. In some embodiments, reader management graphical user interface 2100 may present a screen view providing, in one example, dual tables displaying "In Mine" and "Out of Mine" summaries to facilitate personnel location in an emergency situation and/or for a quick overview and/or location confirmation of personnel and/or equipment.

Figure 22:
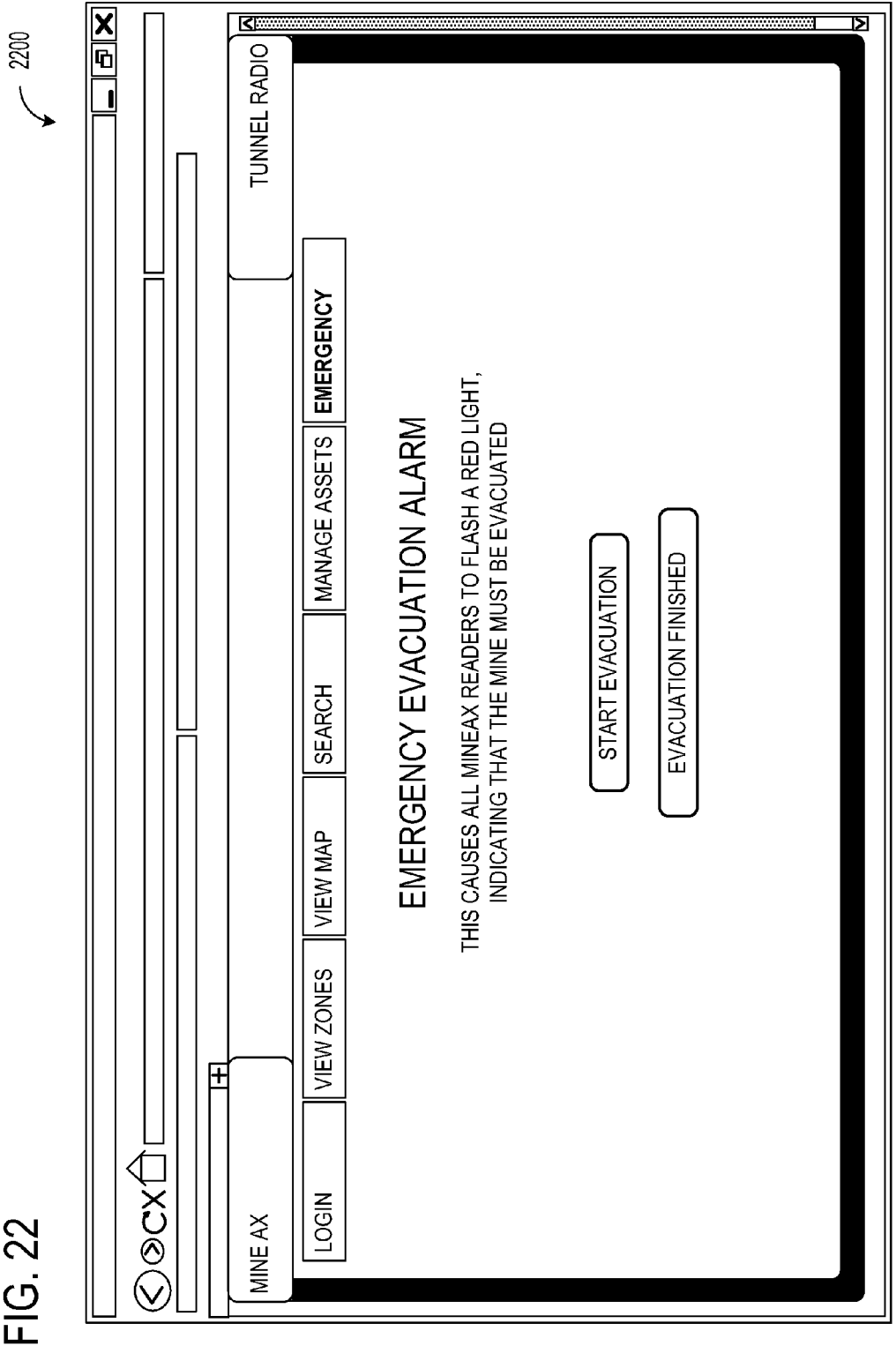
FIG. 22 shows an example emergency evacuation alarm graphical user interface in accordance with an embodiment of the present disclosure.
Figure 23:
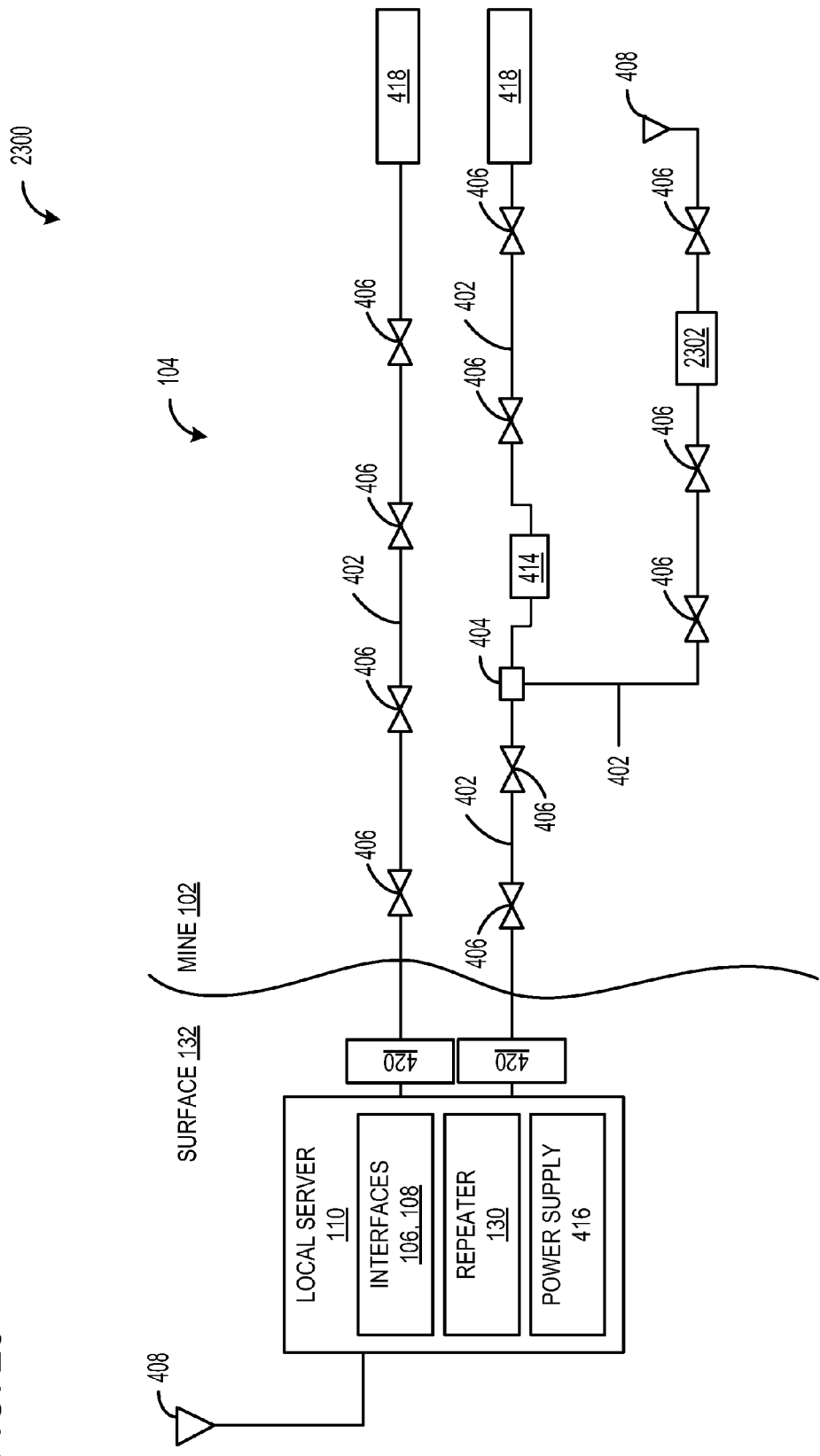
FIG. 23 schematically shows an example mine radio network that may be used with a wirelessly-linked RFID system in accordance with an embodiment of the present disclosure.

As another example, FIG. 22 shows an example emergency evacuation alarm graphical user interface 2200. An emergency evacuation alarm graphical user interface may be used, in some embodiments, to activate and/or flash an indicator light on one or more wirelessly-linked RFID readers.

Turning back to FIG. 3, in some embodiments, user interface module 322 may include a configuration module 334 for configuring various aspects of user interface module 322, tracking headend interface unit 108, etc. In some embodiments, configuration module 334 is only available to users possessing adequate access permissions. For example, configuration module 334 may only be accessible by technical support personnel and/or factory service technicians.

As illustrated, local server 110 may be linked to one or more remote servers 122 via network 120 which may access local server 110 concurrently. Remote servers 122 may facilitate remote control and configuration of wirelessly-linked RFID tracking system 100. In a first example, remote server 122 may be used by a factory service technician to remotely troubleshoot one or more wirelessly-linked RFID readers 112 via network 120. In a second example, remote server 122 may provide software and/or firmware updates to wirelessly-linked RFID tracking system 100.

In some embodiments, remote server 122 may access user interface module 322 via network 120, which may be presented as a web interface. Additionally or alternatively, remote server 122 may have a separate remote server user interface module (not shown) providing some or all of the functionality described above with respect to user interface module 322 of local server 110. Remote servers 122 may be any suitable server computing device, such as a networked cloud environment and/or a networked standalone server. The example of FIG. 3 shows a mine headquarters remote server 122A, which may provide access to the user interface module 322 and/or tag information 204 to authorized users remote from mine 102. The example of FIG. 3 also shows a manufacturers' remote server 122B, which may provide access to aspects of wirelessly-linked RFID tracking system 100 to authorized users at a system manufacturing location, such as authorized factory service representatives.

Figure 30:
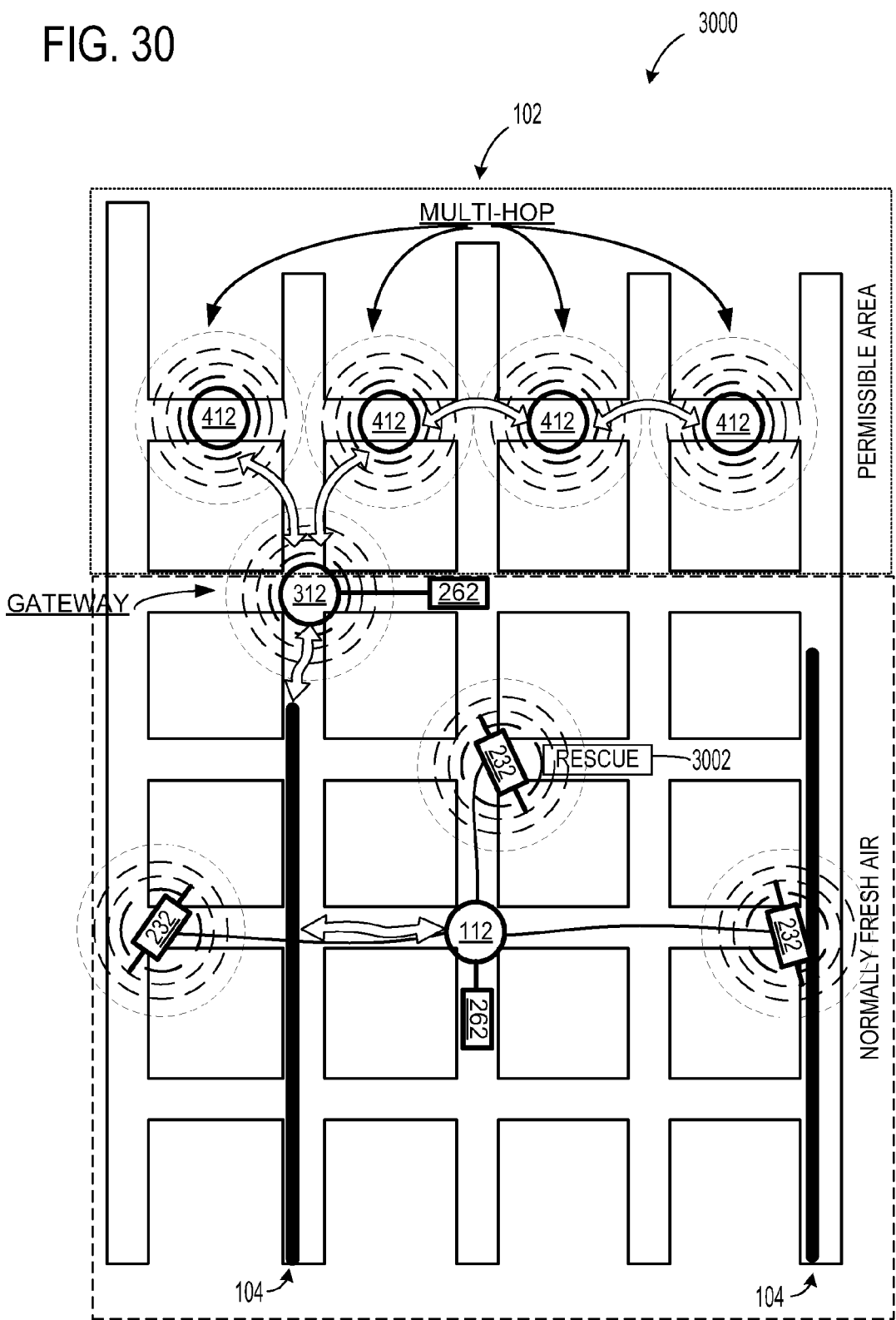
FIG. 30 shows a non-limiting example inby operating environment for a wirelessly-linked RFID system in accordance with an embodiment of the present disclosure.

As described above, the RFID tracking system may be configured in a multi-hop mode. FIG. 30 schematically shows another example operating multi-hop environment for a wirelessly-linked RFID tracking system 3000. It is noted that multi-hop systems may also be deployed in any type of facility, mine or shielded or non-shielded area where all-wireless link operation is convenient and useful. In this non-limiting example, an inby system is shown. However, the system may be employed in an outby or fresh air zone, or anywhere in a hardrock, non-coal mine. Further such system may be deployed to relay and wirelessly link out of an open pit mine. For example, and not as a limitation, the system may be used where the mine entry portal is in the lower part of an open pit, and connectivity is required out and to facilities out and over the upper edge of such and open pit mine operation.

As described below, the RFID tracking system incorporates a plurality of RFID readers which can communicate to the surface and provide internal communications and tracking. In some systems, the multi-hop may include a cascading multi-hop RFID reader system. Such systems may be considered a hybrid system, such that communications can travel along the multi-hop RFID readers and then along the backbone radio channels. Battery power may be used with the multi-hop RFID readers.

It should be appreciated that the system may use a combination of a spoken wheel topology and a cascade topology. For example, as discussed in more detail below, a spoken wheel topology may be used in the backbone, with a cascade topology used for the multi-hop RFID readers. This combination may take advantage of the efficiency of the spoken wheel topology while also allowing extension of the system.

In one example system, the low-power wirelessly-linked RFID system may include a combination of a leaky feeder system, a standard RFID reader, a gateway RFID reader and a plurality of multi-hop RFID readers. For example, and not as a limitation, the leaker feeder system may have a reader transmitting at approximately 468-470 MHz and a reader receiving at 451-453 MHz. This channel may also be the 2-way communication channel. The gateway RFID reader may then further communicate with the multi-hop RFID readers, which may be over a 460.0 MHz channel using simplex. As the multi-hop RFID readers use a channel between the range of the gateway RFID reader transmission and the leaky feeder system, there may be minimized data crossover and interference with other operating channels. The multi-hop RFID readers can then send reader, tag, and sensor card information to the gateway RFID reader, which when polled, provides its own files and tags for transmission along the leaky feeder backbone channel for surface communication. As discussed herein, the combination of the multi-hops with the over 400 foot range and minimal current draw (less than 10 milliwatts maximum power) enables a low power wireless-linked RFID tracking system and environmental sensing system.

Specifically, FIG. 30 shows a wirelessly-linked RFID reader 112, a wirelessly-linked gateway RFID reader 312, and wirelessly-linked multi-hop RFID readers 412. One or more of the readers may be linked with a power supply 262 and/or power cable. Other readers may be battery powered. For example, in on example, wirelessly-linked gateway RFID reader 312 and wirelessly-linked multi-hop RFID reader 412 include a battery internal to the RFID reader.

As shown, each RFID reader may have an RFID tag range as indicated by the concentric circles around the readers. Further, a remote reader antennae 232 may be linked with one or more of the RFID readers, such as RFID reader 112. The remote reader antennae may be posited in various selected positions with the working section, such as along a rescue chamber 3002, a fresh air channel or other outlet. As one example, in some embodiments, it may be desired to position a RFID reader with an integrated environmental sensor, such as a methane sensor, along an air curtain. The use of a reader with a methane sensor along an air curtain may provide data regarding air flow conditions such that mine conditions can be rapidly evaluated from the working site and from the surface. Thus, in some embodiments, conditions and location may dictate the use of the integrated environmental sensor, such as a methane sensor.

A leaky feeder system 104 may further be disposed in the work section. One or more RFID readers, such as gateway RFID reader 312 may be communicatively coupled to the leaky feeder to provide communications through the backbone communications systems.

RFID readers 112, 312, 412 may be arranged in virtually any configuration in order to facilitate transmission. It will be appreciated that wirelessly-linked RFID readers 112, 312, and 412 may have similar configurations, and may be regarded as different RFID readers when operating in different modes and/or when in communication with different devices. For example, RFID reader 112 may include one or more ports configured to communicate with a plurality of different devices such as one or more of another RFID reader, a network, a remote antenna and/or a sensor which are provided as non-limiting examples.

It will be appreciated that the example wirelessly-linked RFID tracking system 3000 shown in FIG. 30 shares common features with the wirelessly-linked RFID tracking system 100 of FIG. 1, and such features are indicated by common reference numbers. Additionally, it will be appreciated that system 3000 may include additional features not shown in FIG. 30, but described with respect to FIG. 1. In other words, system 3000 illustrated in FIG. 30 shows features compatible with an example non-surface environment (e.g., mine 102), which may be configured to communicate with features compatible with another example environment (e.g., surface 132 of FIG. 1).

As discussed above, an RFID reader with a communication port enabled to communicate with other RFID readers may be a wirelessly-linked multi-hop reader 412. Such a multi-hop reader 412 may thus be configured as a relay device, to relay RFID tag information to another RFID reader. As another example, a RFID reader may include software enabled to communicate with another RFID reader, such as a wirelessly-linked gateway RFID reader 312, and a network, such as mine radio network 104. As another example, an RFID reader may be enabled to communicate with a network and a remote antenna as a wirelessly-linked RFID reader 112. It will be appreciated that the aforementioned RFID reader examples are non-limiting and that other combinations and/or configurations are possible. Wirelessly-linked RFID readers 112, 312, and 412 may be configured as a stand-alone interlinked network from all points within a mine or other facility, and as such, require no additional radio network for wireless data interconnection one to another multi-hopping out to the RFID head unit on the surface, or where interconnection may take place to the control server.

In some embodiments, as discussed in more detail below, environmental sensors, such as, but not limited to methane sensors, may be integrated or added to one or more RFID readers. Thus, environmentally-selected conditions, such as methane or other gas conditions, may be wirelessly detected across the entire working section or location in any facility so equipped, such as in a petroleum drill platform. Both workers at the working section and at the surface may obtain data about the environmental conditions using the wireless communication network (and/or the hybrid communication network) provided by the wirelessly linked readers. Additional discussion regarding example environmental sensors is provided in more detail in regards to FIGS. 33-36B.

Figure 31:
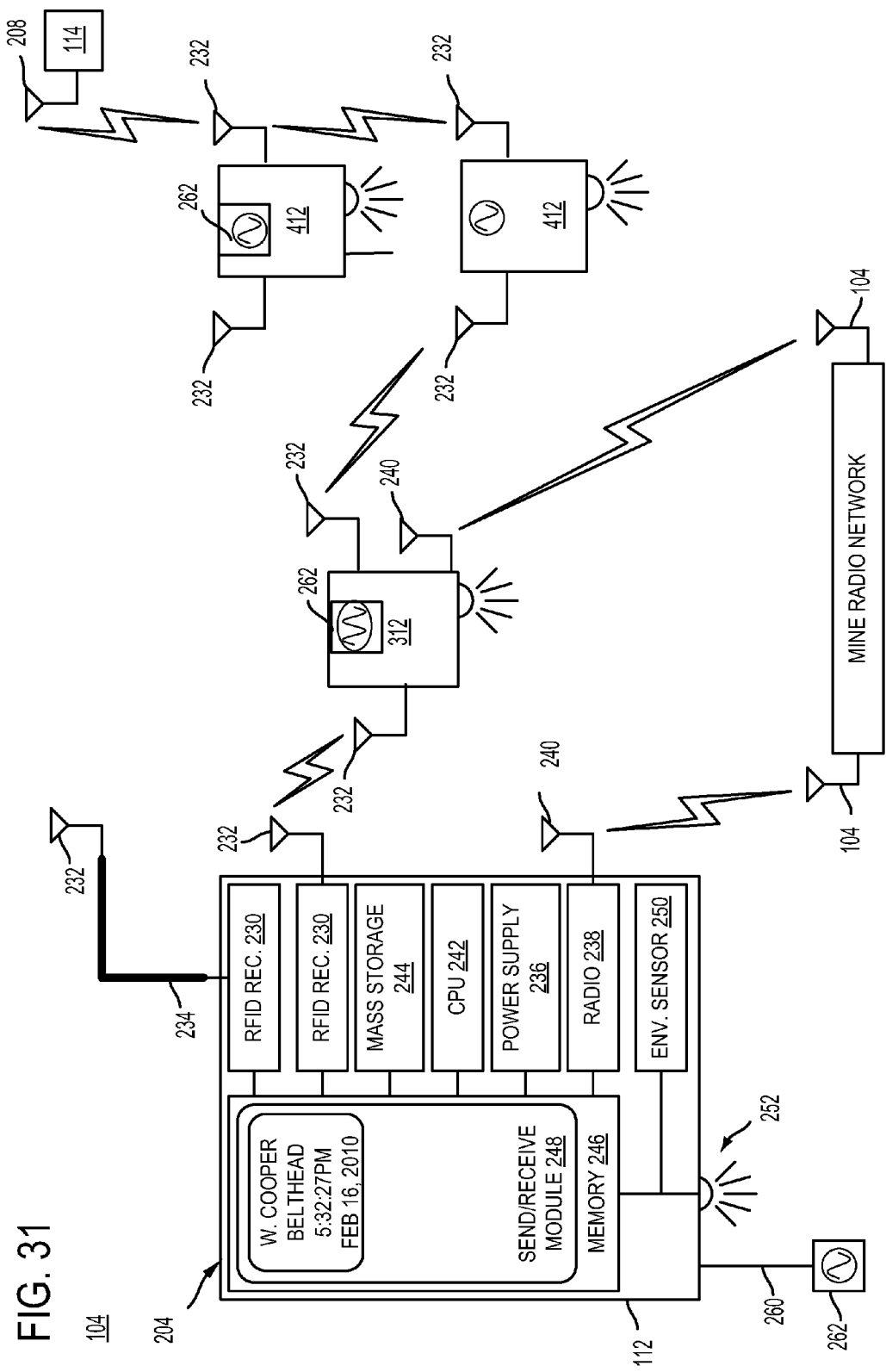
FIG. 31 schematically shows an example wireless RFID reader and example RFID transmitters in accordance with an embodiment of the present disclosure.

As another illustration of a multi-hop system, FIG. 31 schematically shows example wirelessly-linked RFID reader 112, wirelessly-linked gateway RFID reader 312, and wirelessly-linked multi-hop RFID readers 412 in communication with an example RFID tag 114. The system may be at least partially battery operated. For example, wirelessly-linked gateway and multi-hop RFID readers 312 and 412 may include batteries 3102. However, as described above, it will be appreciated that the aforementioned readers may additionally include a backup power supply. As shown, information pertaining to RFID tag 114 may be transmitted to one or more multi-hop RFID readers 412, passed to RFID reader 312, and further passed to RFID reader 112 and/or mine radio network 104. It will be appreciated that FIG. 31 shows RFID readers 312, 412 and RFID tag 114 in simplified form by way of example. It will also be appreciated that the illustration in FIG. 31 is similar to that of FIG. 2 and therefore shares features that are indicated by common reference numbers, as described above.

Figure 32:
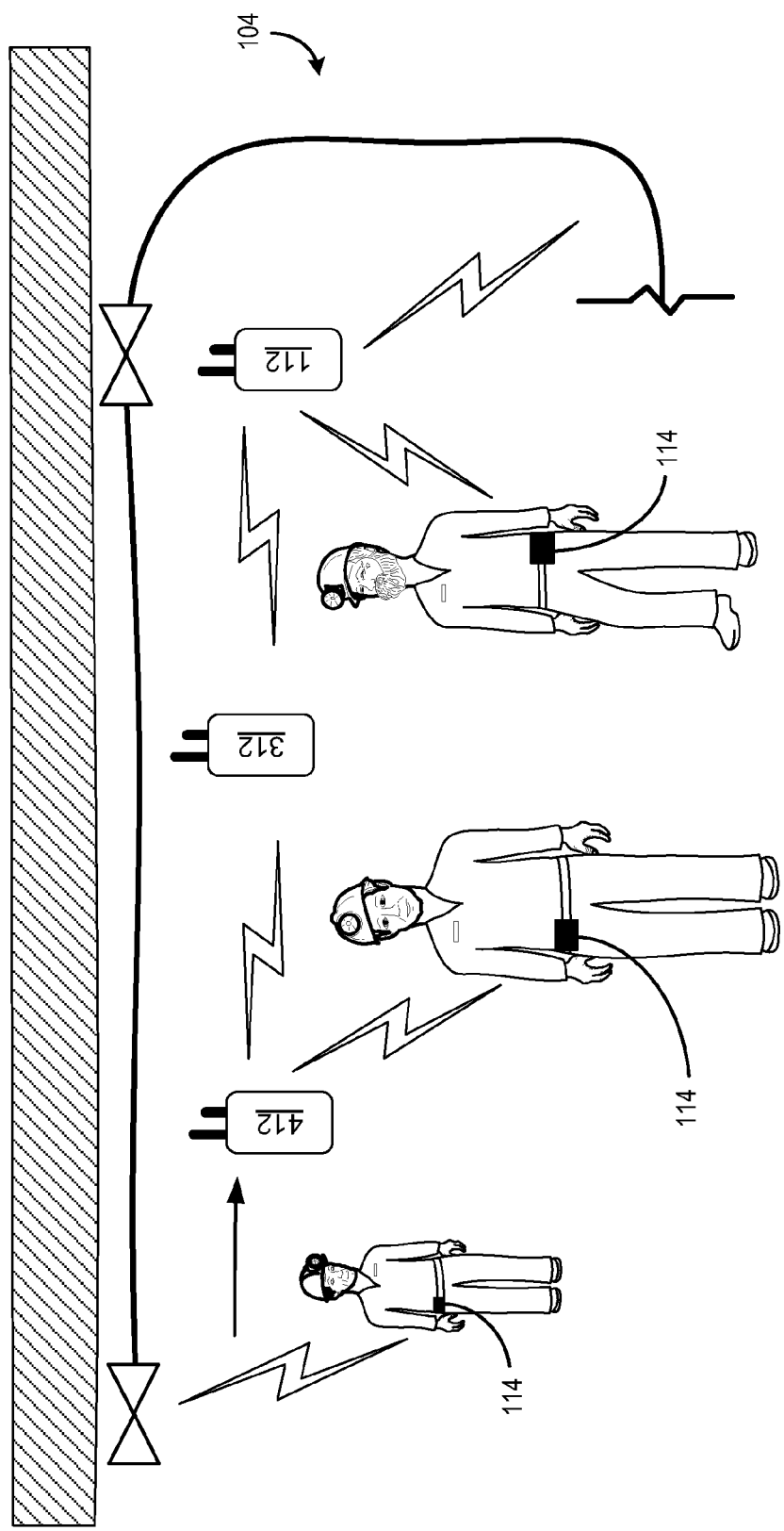
FIG. 32 schematically shows another example of a wireless RFID reader and example RFID transmitters in accordance with an embodiment of the present disclosure.

FIG. 32 shows an example multi-hop mode where RFID readers 112, 312, 412 receive transmissions from personnel-mounted embodiments of RFID tags 114. It will be appreciated that the illustration in FIG. 32 is similar to that of FIG. 6 and therefore shares features that are indicated by common reference numbers, as described above. As shown, RFID tag 114 may transmit a signal to RFID reader 412, which may be relayed to RFID reader 312. RFID reader 312 may directly transmit the signal to a network 104 and/or may transmit the signal to RFID reader 112. RFID reader 112 may then transmit the signal to network 104. It will be appreciated that other arrangements are possible and the scenario illustrated in FIG. 32 is provided as one example and additional and/or alternative RFID readers, remotes antennas, networks and/or sensor may be included without departing from the scope of this disclosure.

Further, it will be appreciated that the basic multi-hop operation shown in FIG. 32 may provide the potential advantage of reducing the prevalence of hard-wired readers in a working mine face area. For example, hard-wired readers may create a nuisance of inter-cabling which may be subject to breakage from moving machinery, personnel and equipment. Many coal mines have seams that can exceed 48 inches and the issue may be even more pronounced as the seam gets lower. Thus, the multi-hop reader units advantageously interconnect wirelessly out of a critical zone and the last reader or "gateway" reader repeats the information over to the mine radio network for connection to the surface, or via a chain of other multi-hop units. In this way, information may be transmitted without hard-wired readers.

Figure 33A:
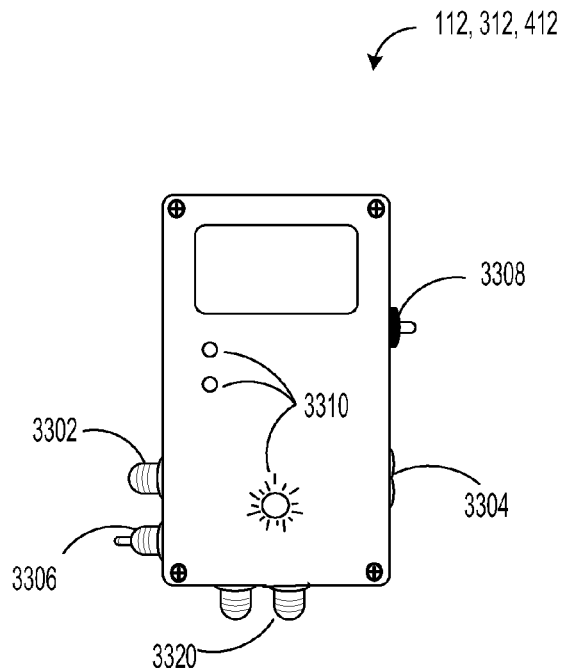
FIG. 33A shows another example of a wireless RFID reader in accordance with an embodiment of the present disclosure.
Figure 33B:
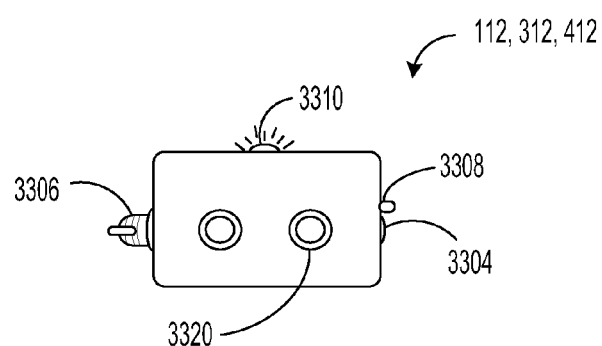
FIG. 33B shows a bottom view of the example wireless RFID reader of FIG. 33A.
Figure 33C:
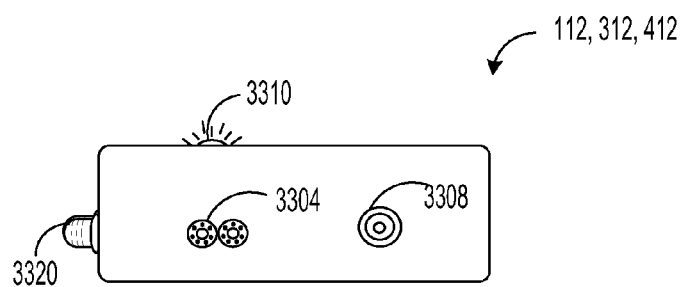
FIG. 33C shows another side view of the example wireless RFID reader of FIG. 33A.
Figure 33D:
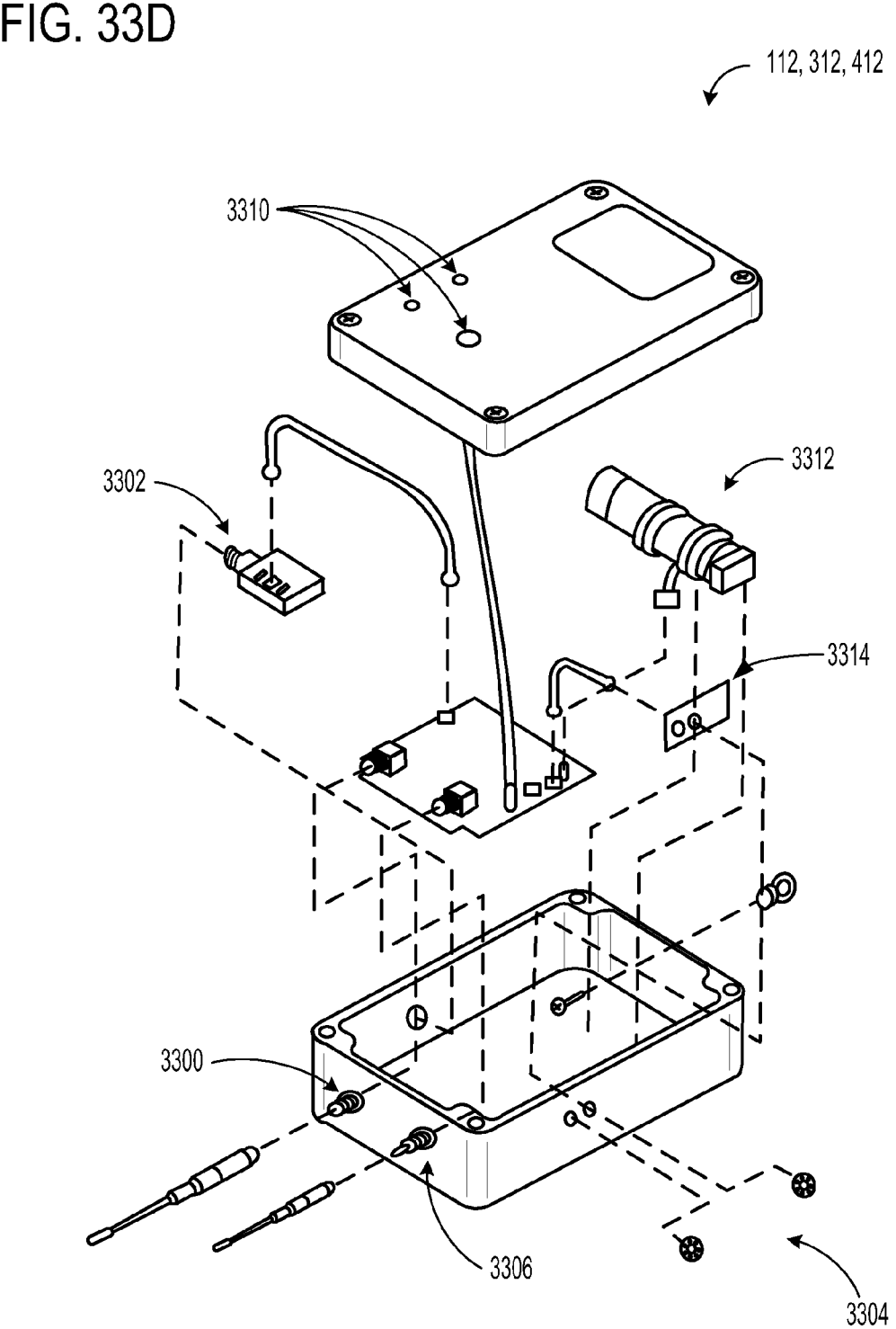
FIG. 33D illustrates an exploded view of another example wireless RFID reader.

FIGS. 33A-33D and 34 show example RFID readers 112, 312, 412. FIG. 33A shows a perspective view of the example RFID reader. FIG. 33B shows a bottom view of said RFID reader, and 33C shows another side view of said RFID reader. FIG. 33D shows an exploded view of another example RFID reader, and FIG. 34 further shows a further example configuration of an RFID reader.

Figure 34:
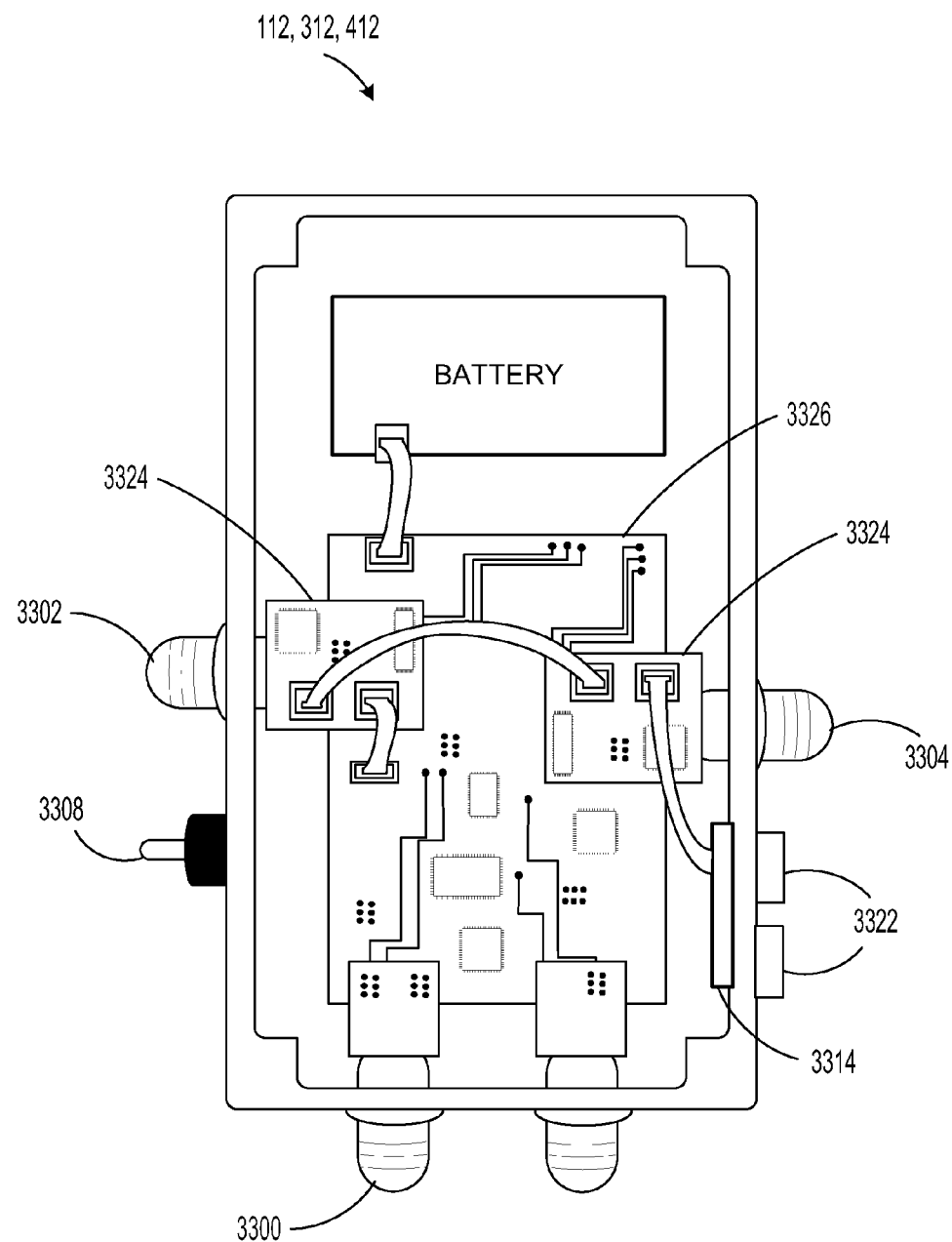
FIG. 34 shows a perspective view of an example wireless RFID reader in accordance with an embodiment of the present disclosure.

Looking briefly at FIG. 34, the primary components of the RFID reader, include the main reader board 3326, expansion boards 3324 and gas sensor board or card 3314. The main reader board is operatively linked with the expansion boards. The gas sensor board is further operatively linked through the expansion board to the main reader board, however other configurations and linkages are possible without departing from the scope of the disclosure.

As described above with respect to FIG. 30-32, RFID readers 112, 312, 412 may be configured to communicate with one or more of another RFID reader, a network, a remote antenna and/or an internally mounted sensor. As shown in the example, the RFID reader may include a plurality of ports. As shown, first port 3300 may be an RFID #1 port. A second port 3302 may be provided as an expansion RFID port and may therefore be an RFID #2 port. In this way, first port 3300 and second port 3302 may be coupled to an antenna, for example, and configured to create independent zones and reduce the number of complete RFID readers needed to provide the coverage required in a given facility or mine.

Further, third port 3304 may be coupled with expansion board 3324. Expansion board 3324 may be operatively coupled with a gas card or gas sensor board, usch as gas card 3314. Environmental sensors 3320 may be operatively linked to the gas card. In some examples, the environmental sensors may protrude or extend through an opening in the housing of the reader. As an example, the environmental sensors, may be a gas sensor, such as a methane, CO, $O_2$, $NO_2$, $SO_2$, or other gas. Further, the environmental sensor may include sensors for pressure, temperature humidity or other environmental status conditions.

As indicated in FIG. 34 and as mentioned above, a gas card 3314, such as a TR-MCO (TUNNEL RADIO-METHANE CO) card, may be operatively coupled to environmental sensors 3322. In some embodiments, the position of the environmental sensors (and the port) may be configured such that the sensor may be more directly exposed to selected environmental conditions. For example, in some RFID readers, a methane sensor may be positioned on the top of a RFID reader, while in other RFID readers, a CO sensor may be positioned towards the bottom of the RFID reader.

It should be appreciated that RFID readers 112, 312, 412 may differ according to the devices that they are enabled to communicate. As one example, RFID readers 112, 312, 412 may have the same configuration and operate in different modes as described above. As another example, RFID readers 112, 312, 412 may have different configurations and thus operate in the particular mode that their particular configuration enables. For example, some RFID readers may have one or a plurality of gas sensor(s) and/or a CO sensor.

It is further noted that FIGS. 33A-33D and 34 illustrate that the RFID reader may include a port 3320, a communications port 3306, a power source port 3308, and one or more indicator devices 3310, such as LEDs. In this example, port 3320, may be a pair of ports for a gas monitor sensor. Further, it will be appreciated that some readers, such as a gateway or multi-hope RFID reader may include a battery 3316 as a primary power source and power source port 3308 may be included as an option to connect to alternative power sources. In some embodiments, an RFID reader may include battery 3316 as a secondary power source, wherein a DC power source may be configured as the primary power source.

As described above, communications port 3306 may be configured to communicate with an existing mine radio network, for example. Further, power source port 3308 may be coupled to a DC power source. Alternatively, the RFID reader may be powered by a battery 3312 contained with an interior of the RFID reader, as shown in FIG. 33D and as described above. Further, the one or more indicator devices 3310 may be a Tag LED, a COMM LED, and/or an emergency LED, for example. Although shown as LEDs, other visual indicators may be used. Alternatively, audio indicators may also be present on the readers. In some examples, the LEDs may provide information regarding the communication and status to the worker in the working section. For example, the emergency LED may provide immediate feedback to a worker of an environmental condition, such as methane, CO or other gas detection at a threshold above a desired level.

As described above, the RFID reader may have gas monitoring capabilities. For example, a gas monitor card 3314 may be included in the RFID reader. The gas monitor card may be configured to enable identification and sensing of certain environmental conditions, such as gas level conditions. For example, the gas monitor card may enable monitoring of gas conditions, such as carbon monoxide, methane, oxygen, $SO_2$, $NO_2$ or other gas. Further, conditions, such as humidity, temperature and pressure may be monitored.

Further, in addition to providing immediate emergency feedback to the worker in the working section, communication may be driven to the surface providing feedback to surface controllers. The surface controllers may thus be immediately notified of the change or identification of an environmental condition. By providing substantially simultaneous communications, workers in the working section cannot simply over-ride a warning indicator of an environmental condition. Surface controllers and data from the surface can be used to identify dangerous or sensitive environmental conditions. It should be appreciated, that in addition to warning indications, data may also be collected by the surface controllers regarding the state or reading from the various environmental sensors. Such data can be compiled and tracked by surface administrators.

It will be appreciated that the illustrations of RFID readers 112, 312, 412 provided in FIGS. 33A-33D and 34 are shown in simplified form, and as such are not meant to be technically precise, but rather to illustrate a general concept. Other shapes, sizes, and configurations of the features shown are possible without departing from the scope of this disclosure.

Figure 35:
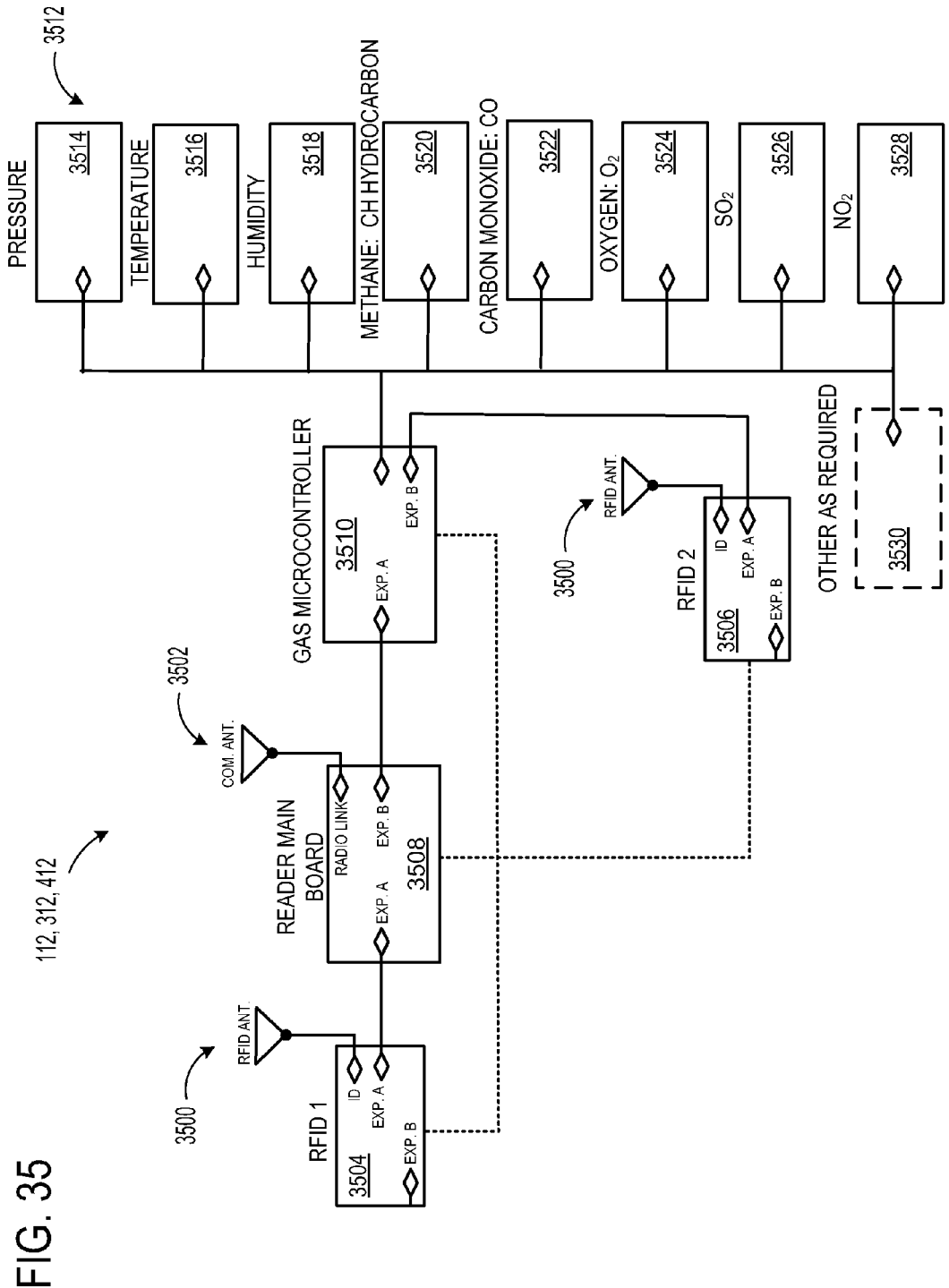
FIG. 35 schematically shows an example configuration of an example RFID reader and environmental sensors in accordance with an embodiment of the present disclosure.

FIG. 35 schematically shows an example configuration of RFID readers 112, 312, and/or 412. It will be appreciated that the configuration as shown is non-limiting and other arrangements are possible. As shown, the RFID reader may include a reader main board 3508 communicatively linked to one or more expansion boards, such as RFID 1 and RFID 2. A gas sensor card or board 3510 may be further operatively linked to the reader main board 3508. In some examples, the gas board may be linked through one of the expansion boards to the main board.

As shown, RFID reader 112, 312, 412 may have more than one antenna, such as RFID antenna 3500 and/or communications antenna 3502. For example, RFID antenna 3500 may be configured to receive RFID tag information, and communications antenna 3502 may be configured to transmit RFID tag information to a mine radio network, as described above.

As shown, an RFID antenna 3500 may be coupled to RFID expansion device 3504 and RFID expansion device 3506 to facilitate data transfer. RFID expansion devices 3504 and 3506 may be system devices and may plug into one of the expansion ports (e.g., EXP. A and/or EXP. B) on any other device to provide tag reading functions. For example, RFID expansion device 3504 is shown communicatively coupled to a master system central processor core and communication system 3508 through an expansion port EXP. A of each device. As another example, RFID expansion device 3506 is shown communicatively coupled to a gas microcontroller 3510 through expansion port EXP. A and EXP. B, respectively. Further, RFID expansion devices 3504 and 3506 may each include an expansion port EXP. B that may be used to support another RFID expansion module or any other compatible device, for example.

As illustrated, communications antenna 3502 may be coupled to master system central processor core and communication system 3508. For example, system 3508 may be a DataBuffer REVC4, a DataBuffer REVC5, or a TMS card, or any other suitable device for radio communication. System 3508 may be configured to receive data from one or more RFID expansion devices and/or data packaged from gas microcontroller 3510. Further, system 3508 may be configured to send the received data over a radio communications link. It will be appreciated that system 3508 may be a stand-alone system without communication capabilities, and may therefore be coupled to another system capable of communicating with a mine radio network, for example.

Figure 36A:
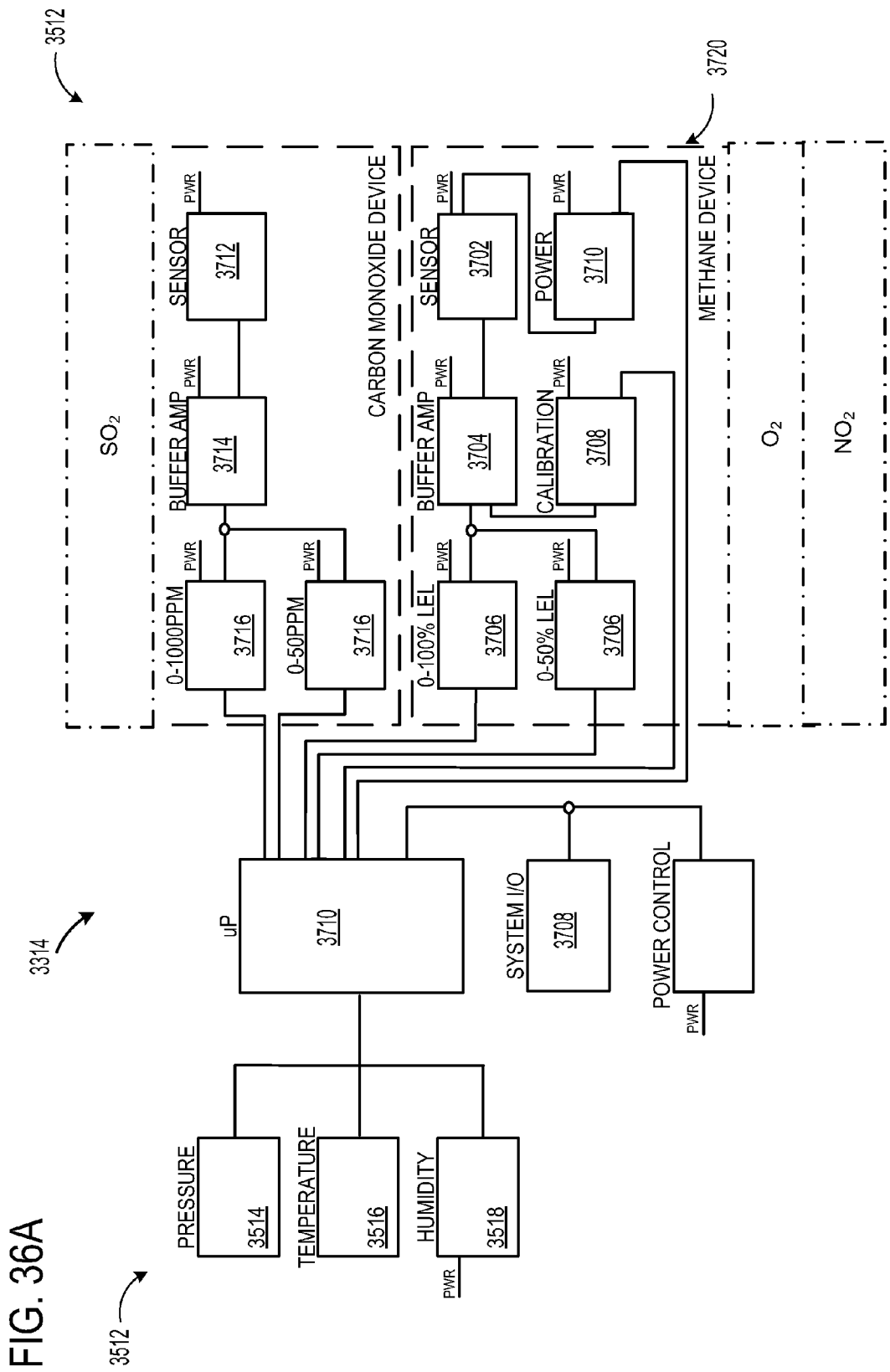
FIG. 36A schematically shows another example configuration of an example gas card/board for the RFID reader in accordance with an embodiment of the present disclosure.

Gas microcontroller 3510 may be configured to read sensor data from one or more environmental sensor devices 3512. FIG. 36A further illustrates the gas sensor board 3314 and related sensors.

Specifically, in FIG. 35, example sensors include pressure sensor 3514, temperature sensor 3516, humidity sensor 3518, methane sensor 3520, carbon monoxide sensor 3522, oxygen sensor 3524, $SO_2$ sensor 3526, $NO_2$ sensor 3528 and other gas or condition sensor 3530. It should be appreciated that the sensors may be integrated on the gas board 3510 or may be cards that may be operatively coupled to the gas sensor board. For example, in some systems, pressure, temperature and humidity may be integrated on the gas sensor board, while methane and other gas sensors may be communicatively linked though a gas specific sensor card to the gas sensor board. The example sensors may be digital or analog sensors, for example.

Gas microcontroller 3510 may be configured to provide power and control to sensors 3512. For example, gas microcontroller 3510 may be configured to include variables for pressure, temperature, humidity, and other factors that may be used to further interpret a gas reading obtained by methane sensor 3520 and/or carbon monoxide sensor 3522. In this way, gas microcontroller 3510 configures, packages, and sends the sensor data to system 3508 in digital format. The sensor data may be further transmitted to a mine radio network via communications antenna 3502, for example. As shown, data may also be communicated between gas microcontroller 3510 and RFID expansion devices 3504 and/or 3506 if the devices are connected via an expansion port, or otherwise in communication with each other.

As indicated above, each of the environmental sensors may be configured to sense and report environmental conditions within a mine, for example. Pressure sensor 3514 may provide information on barometric pressure. Temperature sensor 3516 may provide information on air temperature. Humidity sensor 3518 may provide information on relative air humidity. In this way, one or more of the pressure sensor 3514, temperature sensor 3516, and humidity sensor 3518 sense environmental conditions that may be used to further interpret sensor data sensed by methane sensor 3520 and/or carbon monoxide sensor 3522.

For example, methane sensor 3520 may be a methane pellistor gas sensor and may be configured to provide analog data on methane concentration. FIG. 36A shows an example methane sensor device 3720 in communication with various other devices. As shown, methane sensor device 3720 may be coupled to gas microcontroller 3710, similar to the description above for FIG. 35. In the example provided in FIG. 36A, methane sensor device 3720 may include a sensor module 3702, a buffer module 3704, lower explosive limit (LEL) detection modules 3706, a calibration module 3708, and a power module 3710, for example. Sensing modules, such as sensor module 3702 will be discussed in greater detail below.

Buffer module 3704 may be configured to sample the environment for background conditions, for example. In this way, methane sensor device 3720 may be sensitive to methane concentrations above normal conditions. Likewise, buffer module 3704 may be configured such that methane sensor device 3720 is not prone to false alarms due background methane conditions, for example.

Detection modules 3706 may be configured to trigger an alarm if the sensor module detects a concentration of methane above a threshold value. It will be appreciated that there may be more than one threshold value corresponding to one or more levels of severity associated with methane. Therefore, there may be a detection module for each threshold value. In the example provided, detection modules 3706 measure methane in terms of percent LEL, although it will be appreciated that virtually any unit may be used to measure methane concentration without departing from the scope of this disclosure.

Calibration module 3708 may be configured to calibrate sensor module 3702, buffer module 3704 and/or detection modules 3706. In this way, methane sensor device 3720 may maintain its integrity for accurately detecting methane concentrations in the environment. As one example, calibration module 3708 may be a digitally controlled calibration device such as a digital potentiometer (digital pot). By using a digital pot to calibrate methane sensor device 3720, the sensor may be remotely tested by sending remote commands from a surface environment to a mine environment where the sensor is located, for example.

Further, methane sensor device 3720 may be a catalytic sensor and may act on a bridge circuit such as a Wheatstone bridge. In this example, methane sensor device 3720 may operate according to the catalytic principle. In other words, an electric signal measured by the bridge circuit is directly proportional to combustible gas concentration, such as methane. Therefore, when a sensor is remotely calibrated via the digital pot if there is a mismatch between the adjusted sensor and the bridge circuit signal, then the mismatch is an indication that the sensor is not functioning properly. In this way, a digital pot calibration device allows for remote detection of a malfunctioning sensor.

It will be appreciated that methane sensor device 3720 may be configured as any suitable sensor to detect methane concentration without departing from the scope of this disclosure. As one non-limiting example, the methane sensor may be a catalytic sensor configured to sense a combustible gas such as methane. Further, it is to be understood that any Wheatstone bridge compatible sensor may be used additionally or alternatively to detect other gas concentrations.

Turning back briefly to FIG. 35, carbon monoxide sensor 3522 may be an amperometric gas sensor and may provide analog data on the concentration level of carbon monoxide. FIG. 36A shows an example carbon monoxide sensor device in communication with various other devices. As shown, carbon monoxide sensor device may be coupled to gas microcontroller 3710, similar to the description above for FIG. 35. In the example provided in FIG. 36A, carbon monoxide sensor device may include sensor module 3712, buffer module 3714, and one or more parts per million (PPM) detection modules 3716, similar to the components of methane sensor device 3720, as described above. While not shown in FIG. 36A, it will be appreciated that carbon monoxide sensor device may further include a calibration module and/or a power module similar to methane sensor device 3720.

It will be appreciated that carbon monoxide sensor device may be configured as any suitable sensor to detect carbon monoxide concentration without departing from the scope of this disclosure. Further, it is to be understood that any amperometric gas sensor may be used additionally or alternatively to detect other gas concentrations.

As introduced above, one or more environmental sensors such as methane sensor device 3720 and carbon monoxide device may be configured for a low-powered wirelessly-linked RFID reader.

It is noted that FIG. 36A further illustrates that other sensors may be included. For example, and not as a limitation, sensors for $SO_2$, $O_2$, $NO_2$ or an alternate gas or condition may be provided in combination or as an alternate option. The sensors may be operatively linked in a similar manner as described in regards to the carbon monoxide device and/or the methane device.

Figure 36B:
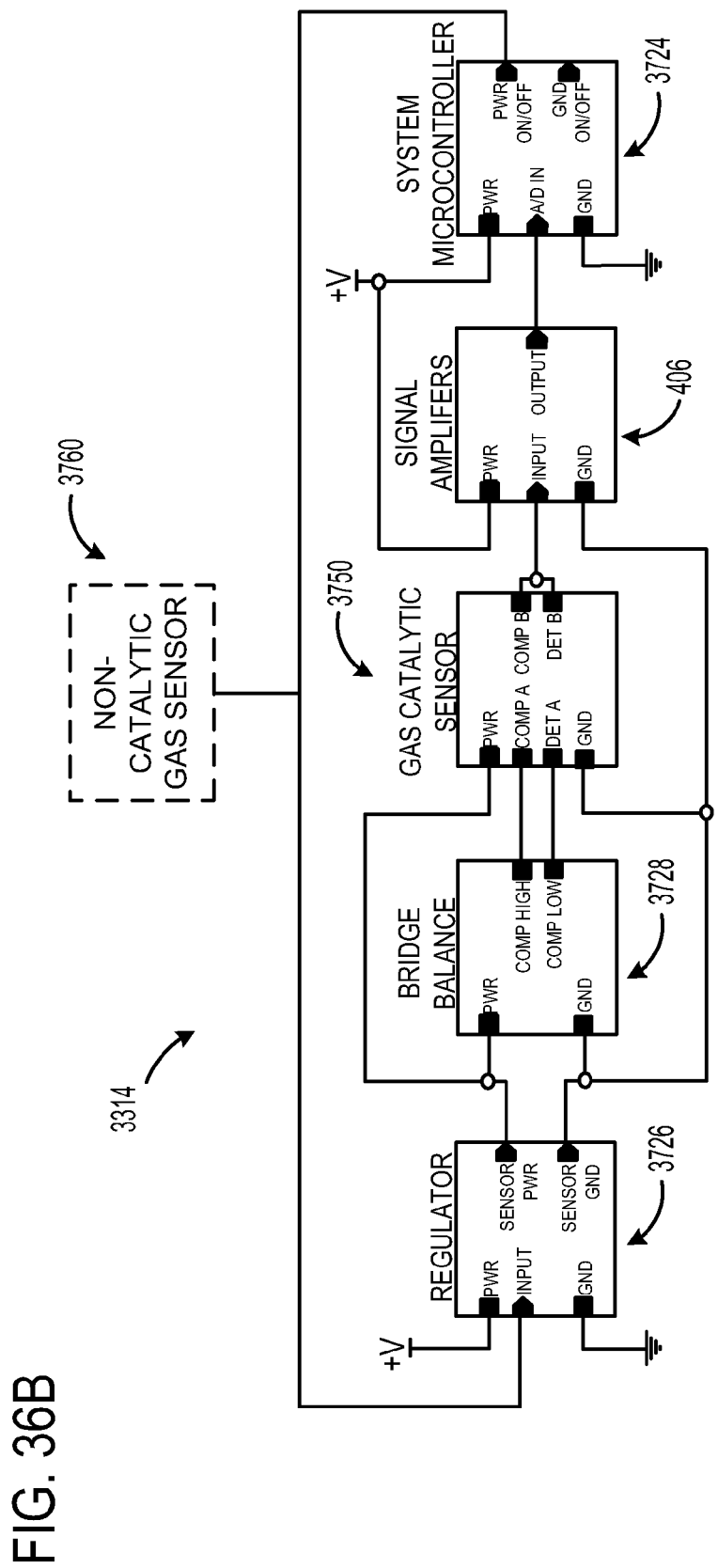
FIG. 36B schematically shows another example gas card/board for the RFID reader of FIG. 36A in a reduced power configuration in accordance with an embodiment of the present disclosure.

FIG. 36B shows an example configuration of a gas sensor board 3314. Specifically, FIG. 36B illustrates gas catalytic sensors at 3750, such as methane device 3720, and carbon monoxide device from FIG. 36A, as well as non-catalytic gas sensors, such as $O_2$, $NO_2$, and $SO_2$ generally indicated at 3760.

As shown, low-powered wirelessly-linked RFID reader 112, 312, 412 may include components similar to those already described above, such as amplifier 406, and sensor (s) (such as the example sensor 3720) and/or non-catalytic gas sensors 3760. Accordingly, these features will not be discussed repetitively. Low-powered wirelessly-linked RFID reader 112, 312, 412 may further include system microcontroller 3724, regulator 3726 and bridge balance 3728.

Microcontroller 3724 applies ground (GND) to all circuits and power to bridge balance 3728 and sensors 3750, 3760 through voltage and current regulator 3726. Microcontroller 3724 may be an on-board processor configured to control power to sensors 3750, 3760. Batteries or another power source may be used to power the board. It will be appreciated that methods for extending battery life may be applied. Further, the schematic shown in FIG. 36B is provided as an example and other configurations are possible without departing from the scope of this disclosure. For example, bridge balance 3728 may be a Wheatstone bridge but it will be appreciated that other bridge circuits are possible.

In one example, environmental sensor device 3512 may include an integrated sensor, such as methane sensing module 3602 or environmental sensor 250. As a further example, environmental sensor device 3512 may include a carbon monoxide sensing module 3604, a temperature sensor, a barometric sensor or combination thereof, all of which are provided as non-limiting examples. In some embodiments, environmental sensor device 3512 may include methane sensing module 3602 and carbon monoxide sensing module 3604. It will be appreciated that one sensing module may be configured to sense more than one gas, variable, and/or condition. For example, a sensing module may be a dual sensing module and may sense both temperature and pressure. However, a dual sensing module is a non-limiting example and a sensing module may be configured to sense virtually any number of gases, variables, and/or conditions. It will be appreciated that environmental sensor device 3512 may be configured to sense additional and/or alternative substances, variables, and/or conditions.

In one example, the carbon monoxide sensor may be configured to be triggered by changes as low as 5 ppm. The identification of change in carbon monoxide levels may enable early identification of combustion conditions. By having the carbon monoxide sensors positioned along various mine positions, it may be possible to reduce and/or identify potential harmful conditions proactively. The data can be available at both the working mine position and at surface level. In some systems, combinations of data from the sensors, including temperature and barometric pressure readings can further provide analysis of mine conditions. Such analysis may occur at a base level at the working mine position or on a surface position.

Likewise, the methane sensors may be positioned to provide both internal working mine position information as well as surface information As discussed above, wirelessly-linked RFID readers 112, 312, 412 may include one or more environmental sensor devices 3512 with one or more sensing modules. For example, environmental sensor device 3512 may include one or more sensing modules to sense any combination or subcombination of methane, carbon monoxide, carbon dioxide, temperature, humidity and pressure, etc. Further, it will be appreciated that one or more environmental sensors may be located externally from RFID readers 112, 312, 412. As another non-limiting example, one or more environmental sensor devices 3512 may be coupled to an RFID tag 114. Environmental sensor devices 3512 may be configured to wirelessly transmit metadata to virtually any receiver in communication with virtually any network, with or without a RFID reader 112, 312, 412, and/or radio repeater 130, to relay a transmission. For example, environmental sensor devices 3512 may be configured to communicate directly with a network located in the same environment (e.g., mine 102) or another environment (e.g., surface 132).

Figure 36C:
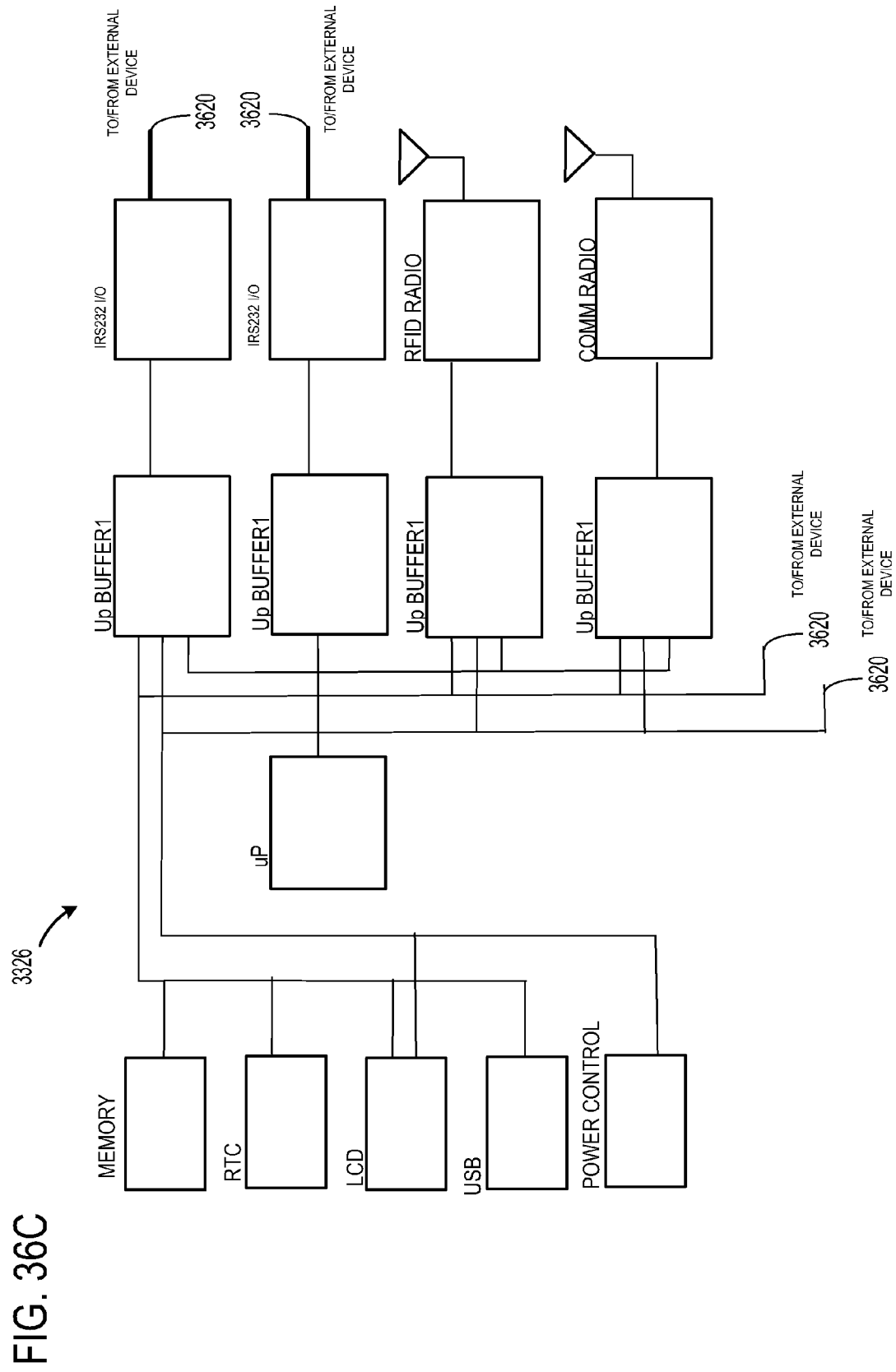
FIG. 36C schematically shows an example main reader board that may be included with an example RFID reader in accordance with an embodiment of the present disclosure.

Turning now to FIG. 36C, an example confirmation of a main reader board 3326 is provided. Details regarding the operation of the main reader board are described above. Further, as shown, main reader board 3326 may include one or more connections, indicated at 3620, for operatively coupling another device such as an expansion board and/or a gas board, for example. It should be appreciated that the board layout is provided as a non-limiting example and other configurations are possible without departing from the scope fo the disclosure.

Figure 36D:
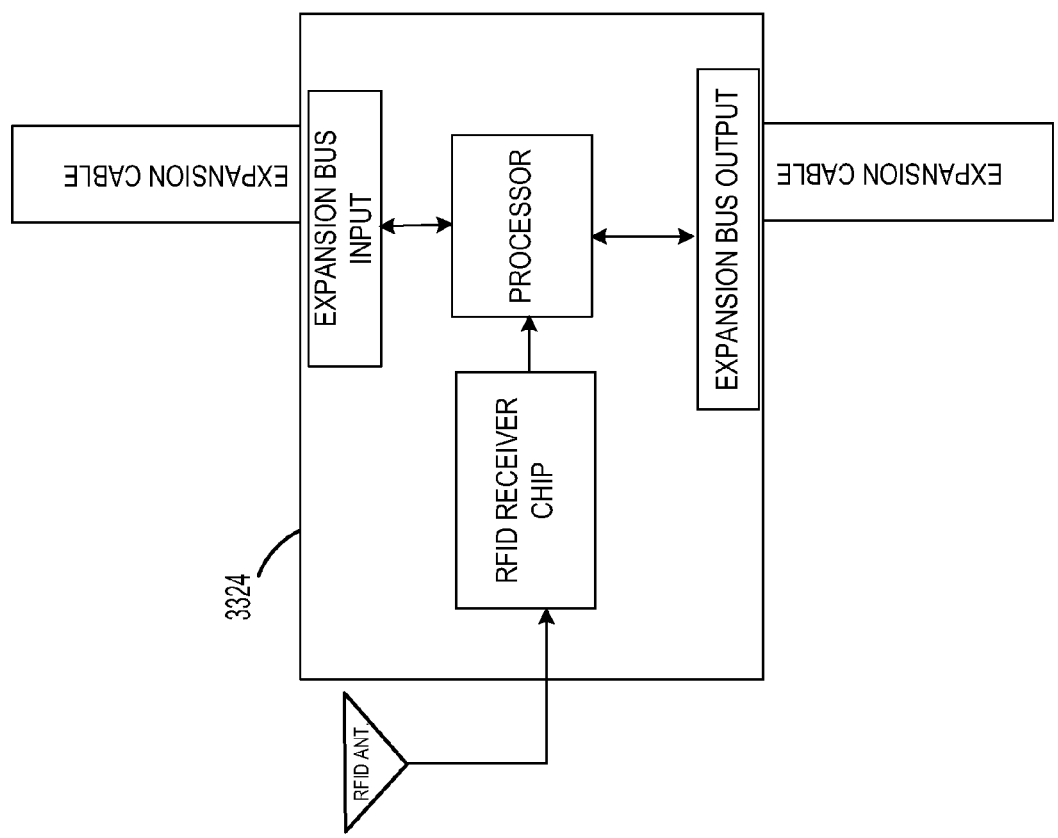
FIG. 36D schematically shows an example expansion board that may be included with an example RFID reader in accordance with an embodiment of the present disclosure.

As described in detail above, FIG. 36D, provides an example confirmation of an expansion board 3324. It should be appreciated that the board layout is provided as a non-limiting example and other configurations are possible without departing from the scope fo the disclosure.

It should be appreciated that the above wirelessly-linked RFID tracking system may enable significant advantages over prior systems. Specifically, ranges of over 400 feet may be obtained using the multi-hop and wirelessly-linked RFID tracking system described herein. This range of over 400 feet may further be accomplished using 10 milliwatts maximum power enabling the system to avoid the cumbersome use of power cables, etc It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. An RFID tracking system wirelessly interfaced with a two-way leaky feeder radio communication network configured to provide radio communications in a shielded environment for tracking at least one self-contained RFID tag in the shielded environment, comprising:
   the at least one self-contained RFID tag; and
   at least one wirelessly-linked RFID reader wirelessly linked to the RFID tag, the wirelessly-linked RFID reader including:
      an RFID receiver and a radio providing two-way voice communication to a user, the RFID receiver electrically transmitting tag information for the RFID tag to a leaky feeder cable through the radio and the radio electrically transmitting voice communication to the leaky feeder cable, the leaky feeder cable included in the two-way leaky feeder radio communication network providing two-way radio communications to system users in the shielded environment via a plurality of devices, said two-way leaky feeder radio communication network configured as a stand-alone interlinked radio network;
   a plurality of ports for communicating with one or more devices configured to sense environmental data, and configured to trigger an emergency indicator based on the environmental data; and
   a server computing device configured to receive transmissions from the radio of the wirelessly-linked RFID reader through the leaky feeder cable in the two-way leaky feeder radio communication network including a radio network headend in electronic communication with the server computing device, the transmissions comprising said tag information for the RFID tag and the environmental data and emergency feedback, wherein the wirelessly-linked RFID reader is communicatively linked to create a data path from the RFID tag through the two-way leaky feeder radio communication network configured to relay two-way voice communications in the shielded environment to a surface environment through the radio network headend.

2. The system of claim 1, wherein the tag information includes a time and a location of a user associated with the self-contained RFID tag.

3. The system of claim 1, wherein the two-way leaky feeder radio communication network configured to provide radio communications in the shielded environment includes a radio repeater, the leaky feeder cable, a coaxial cable, an amplifier, a splitter, a splice box, a termination unit, an antenna, and a power source.

4. The system of claim 1, wherein the self-contained RFID tag is coupled to an asset and tag information associated with the asset includes a date, a time, and a location of the asset.

5. The system of claim 1, wherein the one or more devices includes a power source, one or more other wirelessly-linked RFID readers, and one or more environmental sensors, the one or more environmental sensors selected from the group consisting of a pressure sensor, a temperature sensor, a humidity sensor, a methane sensor, and a carbon monoxide sensor.

6. The system of claim 1, wherein the reader is wirelessly linked to a second reader in a multi-hop configuration.

7. The system of claim 5, wherein the wirelessly-linked RFID reader is configured to further transmit environmental data measured by the one or more environmental sensors.

8. The system of claim 1, wherein the server computing device includes a user interface module configured to provide a graphical user interface for a user to view and control aspects of the RFID tracking system, the user interface module comprising:
   a notification module configured to notify the user of a status of the RFID tag by displaying the associated tag information;
   a map module configured to present one or more graphical map views of an underground environment and/or the surface environment, the map views including a location marker for the wirelessly-linked RFID reader and the RFID tag located within the associated map view;
   a search module configured to allow the user to search for information about a person or an asset bearing the self-contained RFID tag;
   a tag management module configured to provide an interface for managing data associated with the self-contained RFID tag;

a reader management module configured to manage the wirelessly-linked RFID reader deployed throughout the underground environment and the surface environment; and a configuration module configured to provide an interface for controlling aspects of the user interface module.

9. A wirelessly-linked RFID computing device, comprising:
an emergency indicator;
a power source;
a processor;
an RFID receiver electrically communicating with a reader antenna, the reader antenna wirelessly linked to a self-contained RFID tag;
a radio electrically communicating with a leaky feeder cable in a two-way leaky feeder radio communication network to provide two-way voice communication to a user, the two-way leaky feeder radio communication network configured as a stand-alone interlinked radio network in a shielded environment;
a memory holding instructions executable by the processor to:
wirelessly receive tag information from the self-contained RFID tag by way of the reader antenna and RFID receiver;
transmit both the tag information from the RFID tag and voice communication to a server computing device through each of the radio, radio antenna, and the leaky feeder cable in the existing two-way leaky feeder radio communication network;
trigger the emergency indicator based on environmental sensor data received from one or more devices; and
transmit emergency feedback to the server computing device; and
a gas sensor card configured to send environmental sensor data through the existing two-way leaky feeder radio communication network providing radio communications in the shielded environment.

10. The device of claim 9, wherein the gas sensor card is operatively linked to a methane sensor.

11. The device of claim 9, wherein the gas sensor card includes integrated sensors for one or more of pressure, humidity and temperature.

12. The device of claim 9, wherein the gas sensor card is configured to identify a change in an environmental condition within an immediate environment associated with one or more environmental sensors and transmit environmental data to a second wirelessly-linked RFID computing device and/or the server computing device.

13. The device of claim 9, wherein the RFID computing device is configured to indicate a status of an environmental condition.

14. The device of claim 9, wherein the RFID computing device is communicatively linked via the existing two-way leaky feeder radio communication network configured to provide radio communications in the shielded environment to a server located in a surface environment that is configured to display the tag information.

15. The device of claim 9, further comprising one or more indicators that indicate a status of the wirelessly-linked RFID computing device.

16. The device of claim 9, wherein the processor is configured to transmit the tag information to a second wirelessly-linked RFID computing device in a multi-hop mode.

17. A method of tracking RFID tags using a two-way leaky feeder radio communication network extending into a shielded environment, the method comprising:
deploying a plurality of self-contained RFID tags, each self-contained RFID tag configured to transmit tag information identifying the self-contained RFID tag;
deploying a plurality of wirelessly-linked RFID readers, each wirelessly-linked RFID reader comprising an RFID receiver and a radio configured to provide two-way voice communication to a user, the RFID receiver electrically communicating with a reader antenna wirelessly linked to a self-contained RFID tag, and the radio electrically communicating with a leaky feeder cable in the two-way leaky feeder radio communication network providing two-way radio communications to system users in the shielded environment via a plurality of devices, each wirelessly-linked RFID reader interfaced to the two-way leaky feeder radio communication network extending into the shielded environment via the radio and the radio antenna and said two-way leaky feeder radio communication network configured as a stand-alone interlinked radio network; and
at the wirelessly-linked RFID reader:
receiving a tag information transmission from one of the plurality of self-contained RFID tags;
receiving an environmental information transmission from one or more environmental sensors;
triggering an emergency indicator based on the environmental information;
sending a message to a server computing device through the leaky feeder cable and a radio network headend, the server computing device located in a surface environment via the two-way leaky feeder radio communication network extending into the shielded environment, the message including the tag information, the environmental information, and identifying information for the wirelessly-linked RFID reader; and
receiving a voice alert from the server computing device broadcast over the two-way leaky feeder radio communication network, the server computing device generating the voice alert when environmental information received by the server computing device surpasses a threshold value.

18. The method of claim 17, further comprising at the server computing device located in the surface environment:
receiving the message from the wirelessly-linked RFID reader;
comparing the tag information to a manifest; and
displaying a user interface including a location of each of the self-contained RFID tags.

19. The method of claim 17, wherein the tag information includes a time and a location associated with the self-contained RFID tag.

20. The method of claim 17, wherein the environmental information includes one or more of pressure data, temperature data, humidity data, methane data, and carbon monoxide data.

21. The method of claim 17, wherein the identifying information includes a location and a status of the wirelessly-linked RFID reader.

22. The system of claim 1, where the two-way leaky feeder radio communication network has a frequency range of 144-950 MHz.

* * * * *